United States Patent
Chu et al.

(10) Patent No.: US 6,395,710 B1
(45) Date of Patent: May 28, 2002

(54) MACROLIDE ANTIINFECTIVE AGENTS

(75) Inventors: Daniel T. W. Chu, Santa Clara; Gary Ashley, Alameda, both of CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/550,045

(22) Filed: Apr. 14, 2000

Related U.S. Application Data

(60) Provisional application No. 60/129,729, filed on Apr. 16, 1999, provisional application No. 60/172,154, filed on Dec. 17, 1999, provisional application No. 60/140,175, filed on Jun. 18, 1999, provisional application No. 60/172,159, filed on Dec. 17, 1999, provisional application No. 60/173,805, filed on Dec. 30, 1999, and provisional application No. 60/173,804, filed on Dec. 30, 1999.

(51) Int. Cl.⁷ .......................... A61K 31/70; C07H 17/08
(52) U.S. Cl. .............................. 514/29; 536/7.2; 536/7.4
(58) Field of Search .............................. 536/7.2, 7.4, 29

(56) References Cited

U.S. PATENT DOCUMENTS

| | | | |
|---|---|---|---|
| 5,141,926 A | 8/1992 | Weber et al. | ................... 514/29 |
| 5,635,485 A | 6/1997 | Agouridas et al. | ............ 514/29 |
| 5,672,491 A | 9/1997 | Khosla et al. | |

(List continued on next page.)

FOREIGN PATENT DOCUMENTS

| | | |
|---|---|---|
| FR | 2754821 | 4/1998 |
| WO | 97/02358 | 1/1997 |
| WO | 97/42206 | 11/1997 |

(List continued on next page.)

OTHER PUBLICATIONS

Weber J.M. et al. (1991). *Science* 252:114–117.

Primary Examiner—Elli Peselev
(74) Attorney, Agent, or Firm—Carolyn A. Favorito; Kevin Kaster; Christine Ring

(57) ABSTRACT

Compounds of the formula

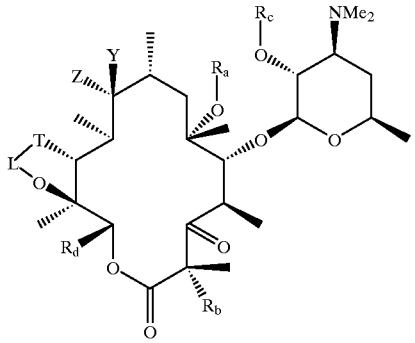

(1)

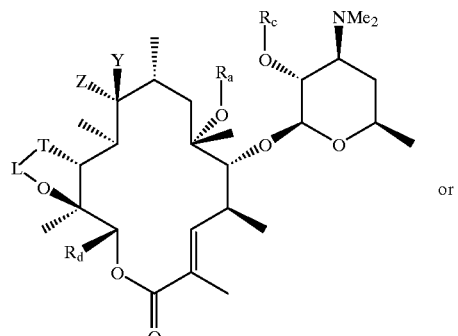

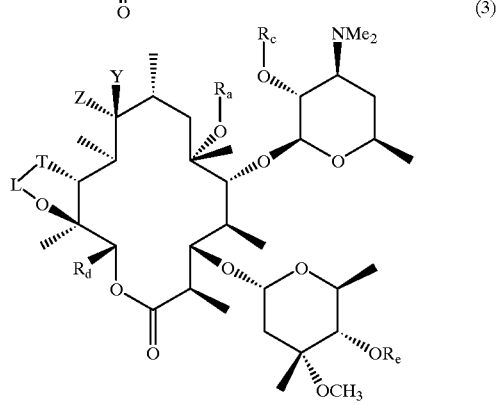

wherein $R_a$ is H; substituted or unsubstituted alkyl (1–10C); substituted or unsubstituted alkenyl (2–10C); substituted or unsubstituted alkynyl (2–10C); substituted or unsubstituted aryl (4–14C); substituted or unsubstituted arylalkyl (5–20); or $OR_a$ is replaced by H;

$R_b$ is H or halogen;

$R_c$ is H or a protecting group;

$R_d$ is methyl, unsubstituted alkyl (3–10C); substituted alkyl (1–10C); substituted or unsubstituted alkynyl (2–10C); substituted or unsubstituted aryl (4–14C); substituted or unsubstituted arylalkyl (5–20C); substituted or unsubstituted arylalkenyl (5–20C); substituted or unsubstituted arylalkynyl (5–20C); substituted or unsubstituted amidoarylalkyl (5–20C); substituted or unsubstituted amidoarylalkenyl (5–20C); or substituted or unsubstituted amidoarylalkynyl (5–20C);

$R_e$ is H or a protecting group;

L is methylene or carbonyl;

T is —O—, —N(R)—, —N(OR)—, —N(NHCOR)—, —N(N=CHR)—, or —N(NHR)— wherein R is H or $R_a$ as defined above, with the proviso that when L is methylene, T is —O—;

one of Z and Y is H and the other is OH, protected OH, or amino, mono- or dialkylamino, protected amino, or an amino heterocycle or Z and Y together are =O, =NOH or a derivatized oxime; including any pharmaceutically acceptable salts thereof and any stereoisomeric forms and mixtures of stereoisomeric forms thereof, are antimicrobial agents.

35 Claims, 19 Drawing Sheets

| U.S. PATENT DOCUMENTS | | | | FOREIGN PATENT DOCUMENTS | | |
|---|---|---|---|---|---|---|
| 5,747,467 A | 5/1998 | Agouridas et al. ............ 514/29 | | WO | 98/01546 | 1/1998 |
| 5,750,510 A | 5/1998 | Elliott et al. | | WO | 98/01571 | 1/1998 |
| 5,770,579 A | 6/1998 | Agouridas et al. ............ 514/29 | | WO | 98/09978 | 3/1998 |
| 5,866,549 A | 2/1999 | Or et al. ....................... 514/29 | | WO | 99/03986 | 1/1999 |
| 6,066,721 A | 5/2000 | Khosla et al. | | WO | 99/21871 | 5/1999 |
| 6,080,555 A | 6/2000 | Khosla et al. | | WO | 99/35157 | 7/1999 |
| 6,121,432 A | 9/2000 | Bonnet et al. ................ 536/7.2 | | WO | 00/26224 | 5/2000 |
| 6,124,269 A | 9/2000 | Phan et al. .................... 514/29 | | WO | 00/26349 | 5/2000 |
| 6,271,255 B1 | 8/2001 | Leadlay et al. ............. 514/450 | | WO | 00/34297 | 6/2000 |
| 6,274,560 B1 | 8/2001 | Khosla et al. ................ 514/29 | | WO | 00/44761 | 8/2000 |
| 6,274,715 B1 | 8/2001 | Or et al. ...................... 536/7.4 | | WO | 00/71557 | 11/2000 |

Illustrative Scheme 7

Formula (6)

Formula (6) anhydro form

Conversion of 15-azidoerythromycin A to 15-amidoerythromycins

*15-amidoerythromycin A conversion to ketolides*

Preffered 15-amido ketolides (X = H,F)

15-ethenylerythromycin A conversion to ketolides

Conversion of 15-ethenyl ketolides to 15-arylethenyl ketolides (X = H,F)

Preffered 15-amido ketolides (X = H,F)

X = H,F

MACROLIDE ANTIINFECTIVE AGENTS

This application claims priority under 35 U.S.C. §119 from U.S. provisional patent application Serial Nos. 60/129,729 filed Apr. 16, 1999, 60/172,154 filed Dec. 17, 1999, 60/140,175 filed Jun. 18, 1999, 60/172,159 filed Dec. 17, 1999, 60/173,805 filed Dec. 30, 1999, and 60/173,804 filed Dec. 30, 1999, and U.S. utility patent application Ser. No. 09/551,162 filed on Apr. 14, 2000 entitled "Macrolide Anti-infectives". The contents of these applications are relied on and incorporated herein in their entirety by reference.

TECHNICAL FIELD

The invention is directed to antibacterial compounds that expand the repertoire of erythromycin-like antibiotics. More particularly, the invention concerns macrolide antibiotics containing an erythronolide nucleus modified at least at the substituent at C-13.

BACKGROUND ART

The increasing number of microbial strains that have acquired resistance to the currently available known antibiotic compounds is recognized as a dangerous threat to public health. As the use of such compounds has proliferated, so too has the need for expanding the options available to treat a wide variety of microbial-based conditions. The need for a larger choice of antimicrobial compounds extends beyond treatment of human infection and to a need to preserve food and other perishable commodities. New antibiotics can also be essential for resistant plants and animals as well as to provide resistance to materials that otherwise are subject to microbially caused corrosion.

Thus, there is a clear need for an expanded armament of compounds which can provide a multifaceted defense against unwanted microbial activity.

WO 98/09978 published Mar. 12, 1998 and incorporated herein by reference discloses modified forms of erythromycin which lack a cladinose residue at the 3-position and which are derivatized in various ways in positions 9–12 of the macrolide ring. Similarly, U.S. Pat. No. 5,750,510, issued May 12, 1998 and incorporated herein by reference, discloses modified erythromycin derivatives.

The naturally occurring erythromycins have the structure

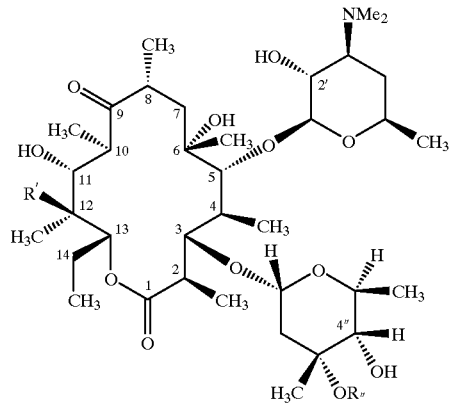

| Erythromycin | R' | R" |
|---|---|---|
| A | —OH | —CH₃ |
| B | —H | —CH₃ |
| C | —OH | —H |
| D | —H | —H | wherein R' can be H or OH and R" can be H or $CH_3$.

All of the compounds disclosed in the above-referenced patent documents contain an ethyl group at position 13 of the macrolide ring. The present inventors have found that alterations in the substituent at position 13 results in a large number of compounds with excellent antibacterial activity.

DISCLOSURE OF THE INVENTION

The invention is directed to erythronolide derivatives that contain modifications from the native structure. All of the compounds of the invention are modified at least at position 13 and have a ring at the 11,12 position.

Thus, in one aspect, the invention is directed to compounds of the formula

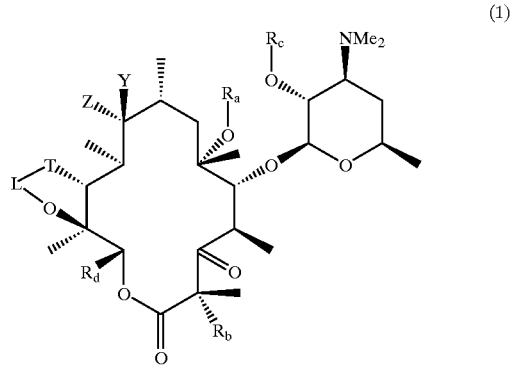

(1)

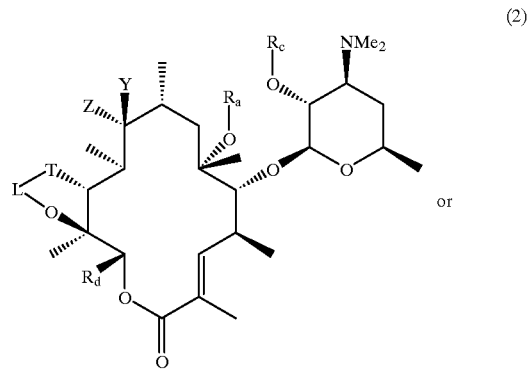

(2)

or

-continued

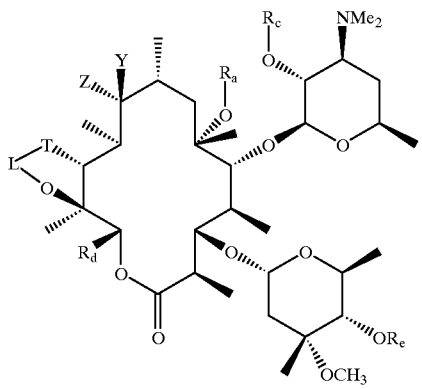

(3)

wherein $R_a$ is H; substituted or unsubstituted alkyl (1–10C); substituted or unsubstituted alkenyl (2–10C); substituted or unsubstituted alkynyl (2–10C); substituted or unsubstituted aryl (4–14C); substituted or unsubstituted arylalkyl (5–20C); or $OR_a$ may be replaced by H;

$R_b$ is H or halogen;

$R_c$ is H or a protecting group;

$R_d$ is methyl, unsubstituted alkyl (3–10C); substituted alkyl (1–10C); substituted or unsubstituted alkenyl (2–10C); substituted or unsubstituted alkynyl; substituted or unsubstituted aryl (4–14C); substituted or unsubstituted arylalkyl (5–20C); substituted or unsubstituted arylalkenyl (5–20C); substituted or unsubstituted arylalkynyl (5–20C); substituted or unsubstituted amidoarylalkyl (5–20C); substituted or unsubstituted amidoarylalkenyl (5–20C); or substituted or unsubstituted amidoarylalkynyl (5–20C);

$R_e$ is H or a protecting group;

L is methylene or carbonyl;

T is —O—, —N(R)—, —N(OR)—, —N(NHCOR)—, —N(N=CHR)—, or —N(NBR)— wherein R is H or $R_a$ as defined above, with the proviso that when L is methylene, T is —O—;

one of Z and Y is H and the other is OH, protected OH, or amino, mono- or dialkylamino, protected amino, or an amino heterocycle or Z and Y together are =O, =NOH or a derivatized oxime;

including any pharmaceutically acceptable salts thereof and any stereoisomeric forms and mixtures of stereoisomeric forms thereof.

In another aspect, the invention is directed to pharmaceutical or preservative compositions containing the compounds of formulas (1)–(3) and to methods to treat infectious diseases by administering these compounds or to preserve materials by providing them.

A BRIEF DESCRIPTION OF THE DRAWINGS

Figure 15:
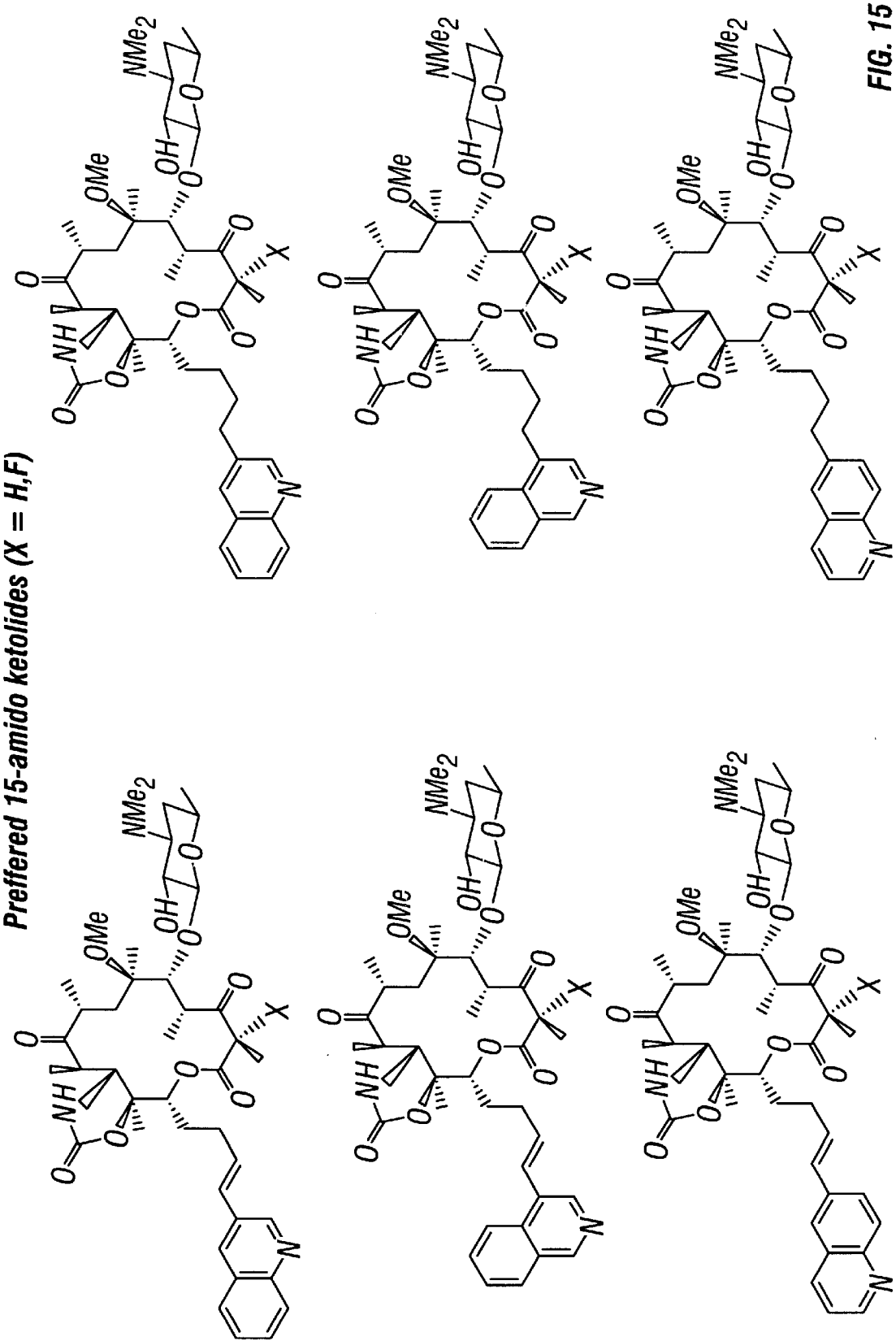

FIG. 15 shows structures of particularly preferred examples of 15-(2-arylethenyl)-6-O-methyl-ketolide 11,12-cyclic carbamates and 15-(2-arylethyl)-6-O-methyl-ketolide 11,12-cyclic carbamates. In each case, X may be either H or F.

Figure 16:
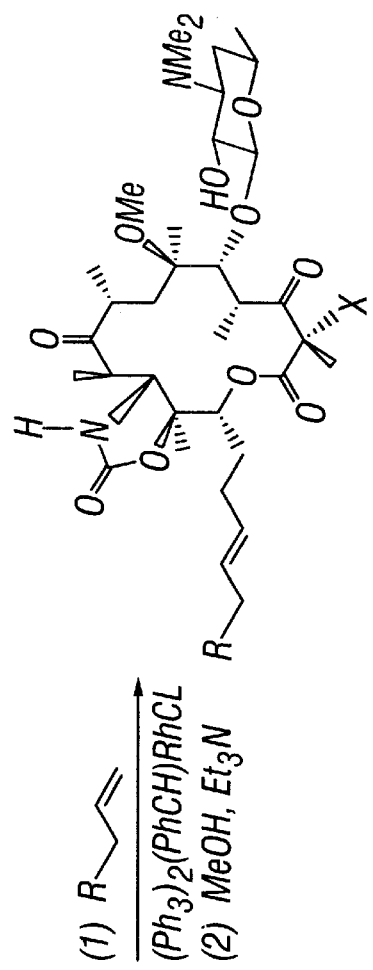
Figure 16:
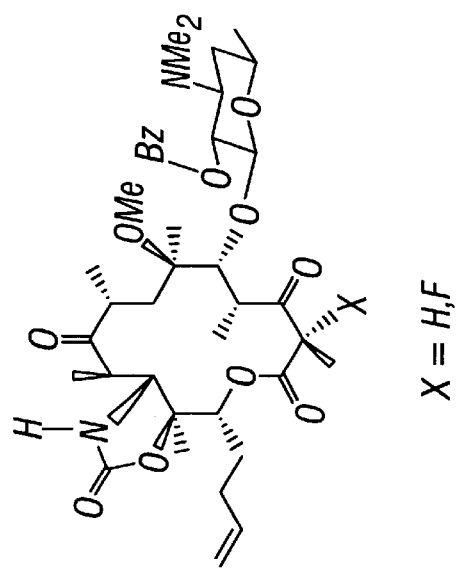

FIG. 16 shows the synthesis of 15-ethenyl ketolides via olefin metathesis.

MODES OF CARRYING OUT THE INVENTION

The compounds of the invention are conveniently synthesized by combining synthetic chemical techniques with microbiological processes involving genetically engineered microorganisms. Briefly, in a preferred mode of carrying out the invention, a microbial host, preferably a host which does not itself produce a macrolide antibiotic, is provided with a recombinant expression system for the production of modified 6-deoxyerythronolide B (6-dEB), which expression system in some instances will have been altered by a disruption in the catalytic domain of the ketosynthase moiety in the first module. For substituents in which $R_d$ is methyl, host cells are used which do not have a disrupted domain of the ketosynthase moiety. This alteration in the 6-dEB polyketide synthase (PKS) results in the inability of this PKS to utilize its native starter unit, and thus permits inclusion of a synthetic diketide thioester for its initial condensation product in the sequence of reactions leading to modified 6-dEB without competition from the diketide that would otherwise, natively, have been produced. Thus, the recombinant host can be provided a synthetic diketide thioester for incorporation into the resulting polyketide. The incorporation of this diketide into the resulting polyketide results in a polyketide with a substituent at position 13 that may be selected as desired. Preferred methods for preparing the synthetic polyketide thioesters are set forth in copending application U.S. Ser. No. 60/117,384 filed Jan. 27, 1999 and 09/492,733 filed on Jan. 27, 2000, which are incorporated herein by reference.

Recombinant forms of the 6-dEB PKS containing inactivated ketosynthase (KS) domains in the first module (KS1)

and appropriate organisms modified to contain an expression system for this PKS are described in PCT applications WO 97/02358, published Jan. 28, 1997 and WO 99/03986, published Jan. 28, 1999, incorporated herein by reference.

The polyketide resulting from expression of the modified PKS is then isolated and purified, if desired, from the recombinantly modified organism and fed to *Saccharopolyspora erythraea*, which contains the functionality for postpolyketide modifications, including glycosylation. Other modifications include hydroxylation at positions 6 and 12. The resulting modified erythromycin is then isolated and chemically modified to obtain the compounds of the invention. Synthetic methods for providing these modifications are described in WO 98/09978 and U.S. Pat. No. 5,750,510, referenced hereinabove.

Figure 1:
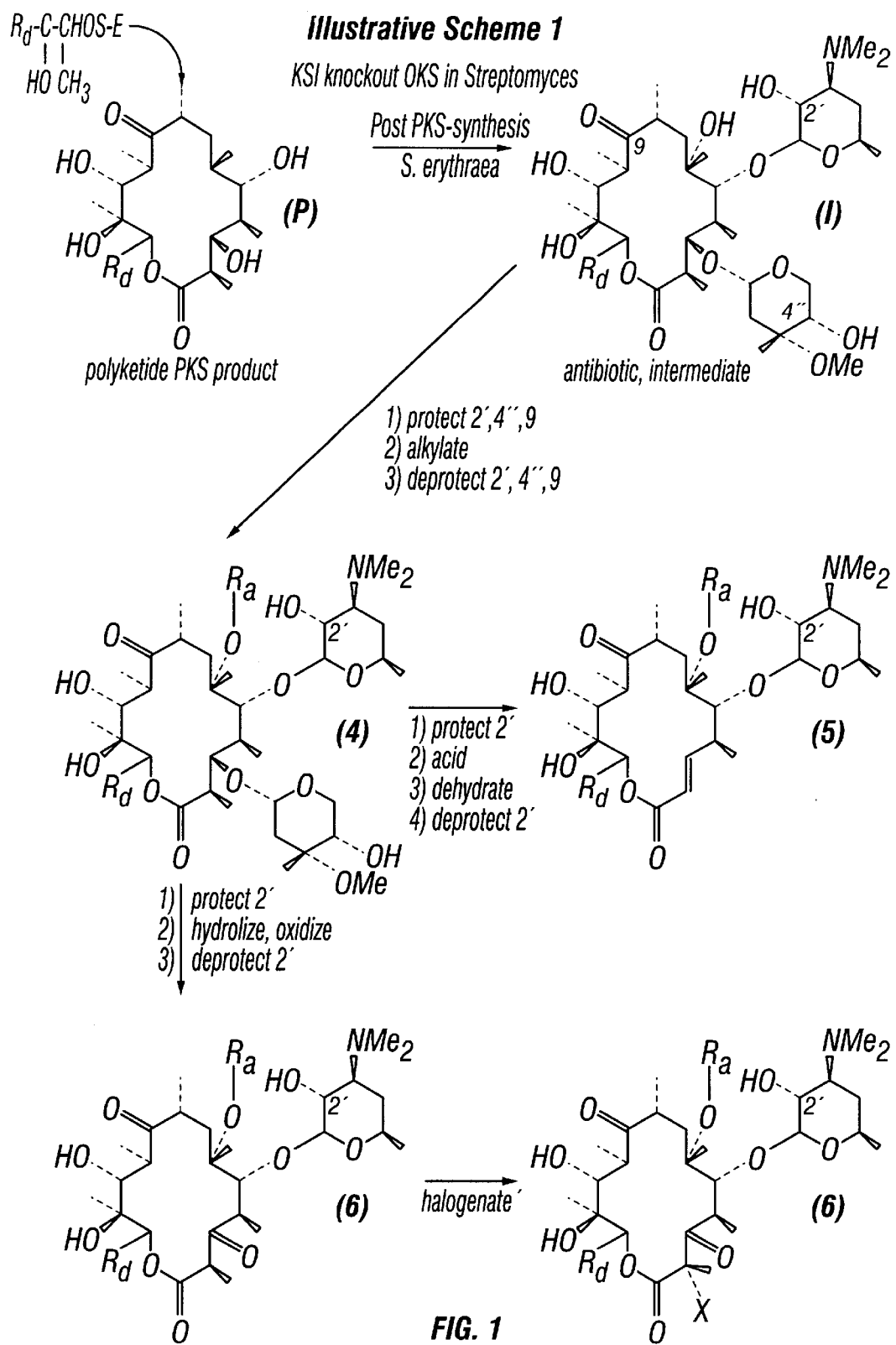
FIG. 1 shows a schematic of the synthesis of intermediates for the compounds of the invention.

The general method for synthesizing intermediates to compounds of the invention is shown in FIG. 1.

Figure 2:
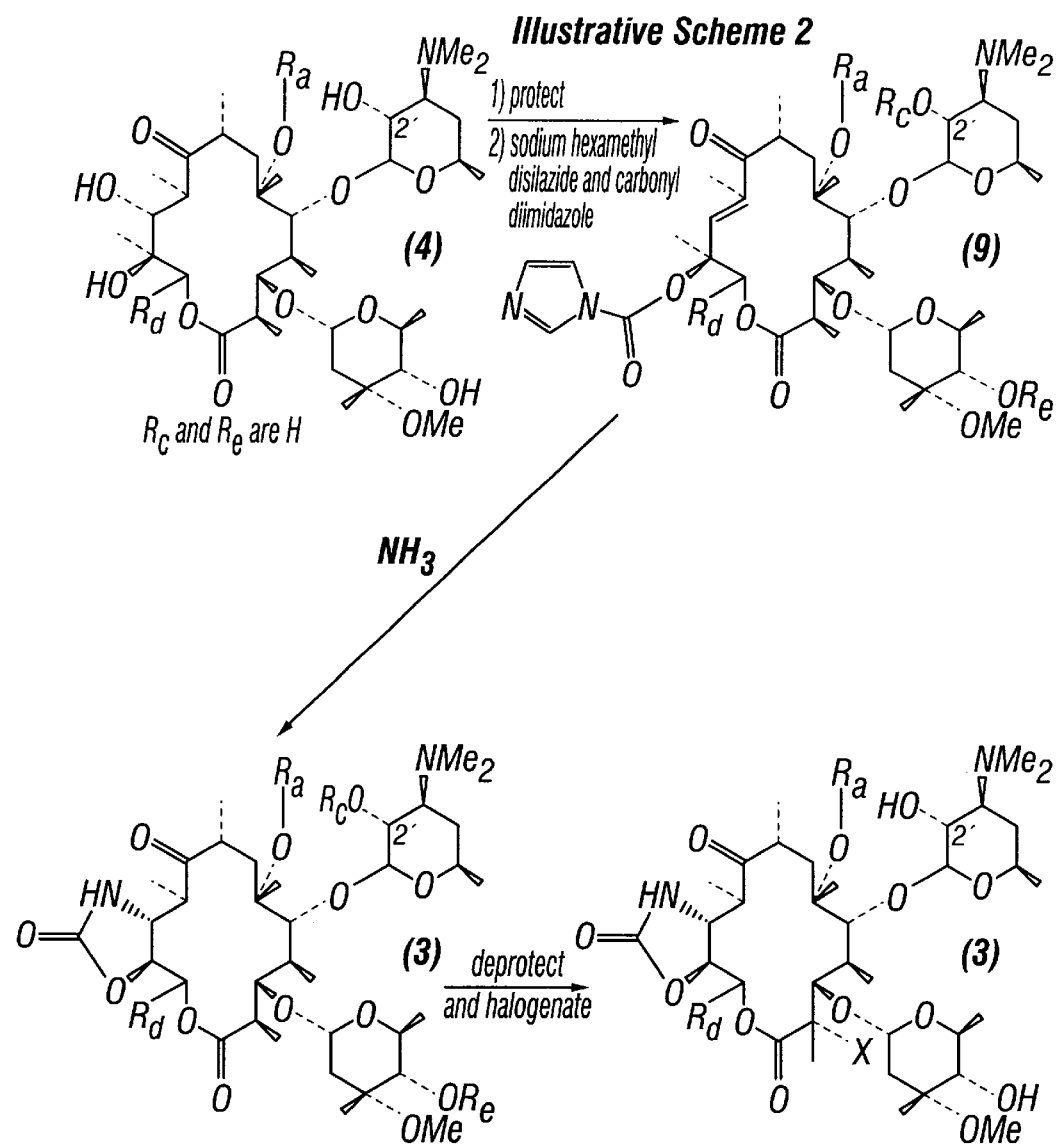
FIG. 2 shows a schematic of the synthesis of the compounds of the invention from these intermediates.

The method for synthesizing compounds from intermediates of the invention is shown in FIG. 2.

The resulting antiinfective compound is active in vitro and in vivo for activity against a panel of representative microorganisms. The compounds of the invention thus exhibit a sufficient diversity in specificity to cover the spectrum of antibiotic activities desired.

For use in treating infectious disease, the compounds of the invention are formulated into suitable compositions which will include typical excipients, pharmaceutically acceptable counterions if the compound is a salt, further additives as desired, such as antioxidants, buffers, and the like, and administered to animals or humans. The types of formulations that are appropriate for these compounds are similar to those for the macrolide antibiotics in general. Formulations may be found, for example, in *Remington's Pharmaceutical Sciences*, Mack Publishing Co., latest edition. The compounds can be administered by any desired route, including injection, oral administration, transdermal administration, transmucosal administration, or any combination. The compounds of the invention can also be administered with additional active ingredients if desired.

The compounds of the invention are of formulas (1)–(3) as set forth above, as well as any stereoisomeric forms of these compounds as shown. The particular stereoisomers depicted are those resulting from the preferred method of synthesis set forth above and exemplified herein; however, by modifying the expression system for the PKS, or by altering the chirality of the diketide, or by synthetic chemical conversion, other stereoisomers may also be prepared. Additional chiral centers may be present in the substituents, such as $R_a$ and $R_d$. The stereoisomers may be administered as mixtures, or individual stereoisomers may be separated and utilized as is known in the art.

The properties of the compounds of formulas (1)–(3) are defined by the substituents $R_a$–$R_e$, L, T, Y and Z. Preferred embodiments of these substituents are set forth hereinbelow. They contain moieties which are defined as follows:

"Halogen" includes fluoro, chloro, bromo and iodo, and most preferably fluoro.

"Alkyl" refers to a saturated straight-chain, branched chain or cyclic hydrocarbyl moiety containing a specified number of carbons and that may contain one or more suitable heteroatoms; similarly, alkenyl and alkynyl refer to straight or branched chain or cyclic hydrocarbon substituents containing one or more double bonds or one or more triple bonds, respectively and that may contain one or more suitable heteroatoms.

"Aryl" refers to an aromatic substituent that may contain one or more suitable heteroatoms such as phenyl, naphthyl, quinolyl, or phenanthryl.

"Arylalkyl," "arylalkenyl," or "arylalkynyl" refer to substituents wherein an aryl group is linked to the substituted moiety through an alkyl, alkenyl or alkynyl linkage, respectively. Again, the number of carbons in the arylalkyl, arylalkenyl or arylalkynyl groups will be specified.

"Amidoarylalkyl," "amidoarylalkenyl," or "amidoarylalkynyl" refer to substituents wherein an aryl group is linked to the substituted moiety through an amido and an alkyl, alkenyl or alkynyl linkage, respectively. Again, the number of carbons in the amidoarylalkyl, amidoarylalkenyl or amidoarylalkynyl groups will be specified.

Thus, included among the defined substituents herein are "heteroalkyl," "heteroalkenyl," "heteroalkynyl," "heteroaryl," "heteroarylalkyl," and the like. Suitable heteroatoms include N, O, and S.

All of the foregoing substituents may be unsubstituted or may be further substituted. Typical substituents include R, —OR, —SR, —NR$_2$, —COR, —COOR, —CONR$_2$, —OOCR, —NRCOR, —OCONR$_2$, —CN, —CF$_3$, —NO$_2$, —SOR, —SO$_2$R, halogen wherein each R is independently H or is alkyl, alkenyl, alkynyl, aryl, arylalkyl, or the hetero forms of these as defined above. In addition, alkyl, alkenyl and alkynyl may be substituted by aryl or heteroaryl, which may, themselves, be further substituted.

"A derivatized oxime" is of the formula =N—O—R, wherein R is other than H and is otherwise defined as above.

A "protecting group" for a hydroxy includes acyl groups, silyl groups, and the like. Suitable protecting groups are described by Greene, T. W., et al., in *Protecting Groups in Organic Sythesis*, $2^{nd}$ Ed., John Wiley & Sons, Inc. (1991), incorporated herein by reference.

The invention includes more preferred embodiments of the compound defined above. $R_d$ is preferably butyl, pentyl, methoxyethoxymethyl, isobutyl, methylcyclohexyl, phenyl, benzyl, ethylphenyl, 3-(benzyloxy)propyl, 2-(pyrimidin-2-ylthio)ethyl, propyl, fluoroethyl, chloroethyl, vinyl, 3-butenyl, or azidoethyl and more preferably propyl, fluoroethyl, chloroethyl, vinyl, 3-butenyl, or azidoethyl. U.S. Ser. No. 60/117,384 filed Jan. 27, 1999 and U.S. Ser. No. 09/492,733 filed Jan. 27, 2000 both of which are incorporated herein by reference describe various oligoketide thioesters, preferably diketide thioesters, that can be incorporated at the C-13 position. Such diketide thioesters as described therein are incorporated into the compounds of the invention and thus determine preferred $R_d$ groups at the C-13 position.

In another preferred embodiment, $R_a$ is H or lower C1–C3 alkyl, and more preferably methyl. $R_a$ is also preferably arylalkenyl or arylalkynyl such as 3-arylprop-2-enyl or 3-arylprop-2-ynyl. Preferably the aryl group in the preferred arylalkenyl or arylalkynyl embodiments are 3-quinolyl, 4-quinolyl, 5-quinolyl, phenyl, 4-fluorophenyl, 4-chlorophenyl, 4-methoxyphenyl, 6-quinolyl, 6-quinoxalyl, 6-amino-3-quinolyl, or 4-isoquinolyl.

When T—L—O forms a carbamate ring, a combination of substituents on the carbamate nitrogen (R), the 6-O position ($R_a$), and the 13 position ($R_d$) are especially preferred. In a first preferred combination, $R_a$ is preferably arylalkyl, arylalkenyl or arylalkynyl; R is preferably H or substituted or unsubstituted lower alkyl; and $R_d$ is preferably substituted or unsubstituted alkyl. In these compounds $R_a$ is more preferably arylpropyl, arylprop-2-enyl, or arylprop-2-ynyl; R is more preferably hydrogen or methyl; and $R_d$ is more preferably propyl, fluoroethyl, or chloroethyl.

In a second preferred combination, $R_a$ is H or substituted or unsubstituted lower alkyl; R is preferably arylalkyl, arylalkenyl or arylalkynyl; and $R_d$ is substituted or unsubstituted alkyl. In these compounds, $R_a$ is more preferably methyl; R is more preferably arylpropyl, arylprop-2-enyl, or arylprop-2-ynyl; and $R_d$ is more preferably propyl, fluoroethyl, or chloroethyl.

In a third preferred combination, when $R_a$ is an unsaturated substituent available for further derivatization such as alkenyl or alkynyl or other group such as azidoalkyl, then preferably $R_a$ is H or substituted or unsubstituted lower alkyl, and R is H or substituted or unsubstituted lower alkyl. $R_a$ is more preferably H or methyl and R is more preferably H. Illustrative unsaturated substituents, $R_d$ are more preferably vinyl, propargyl, or butenyl, and other derivatizable substituents include azidoethyl. These compounds can be readily derivatized by the methods of the invention to form from the unsaturated substituents the arylalkyl, arylalkenyl, or arylalkynyl substituents and from the azido substiuent the amidoarylalkyl, amidoarylakenyl, or amidoarylakynyl substituent.

Figure 12:
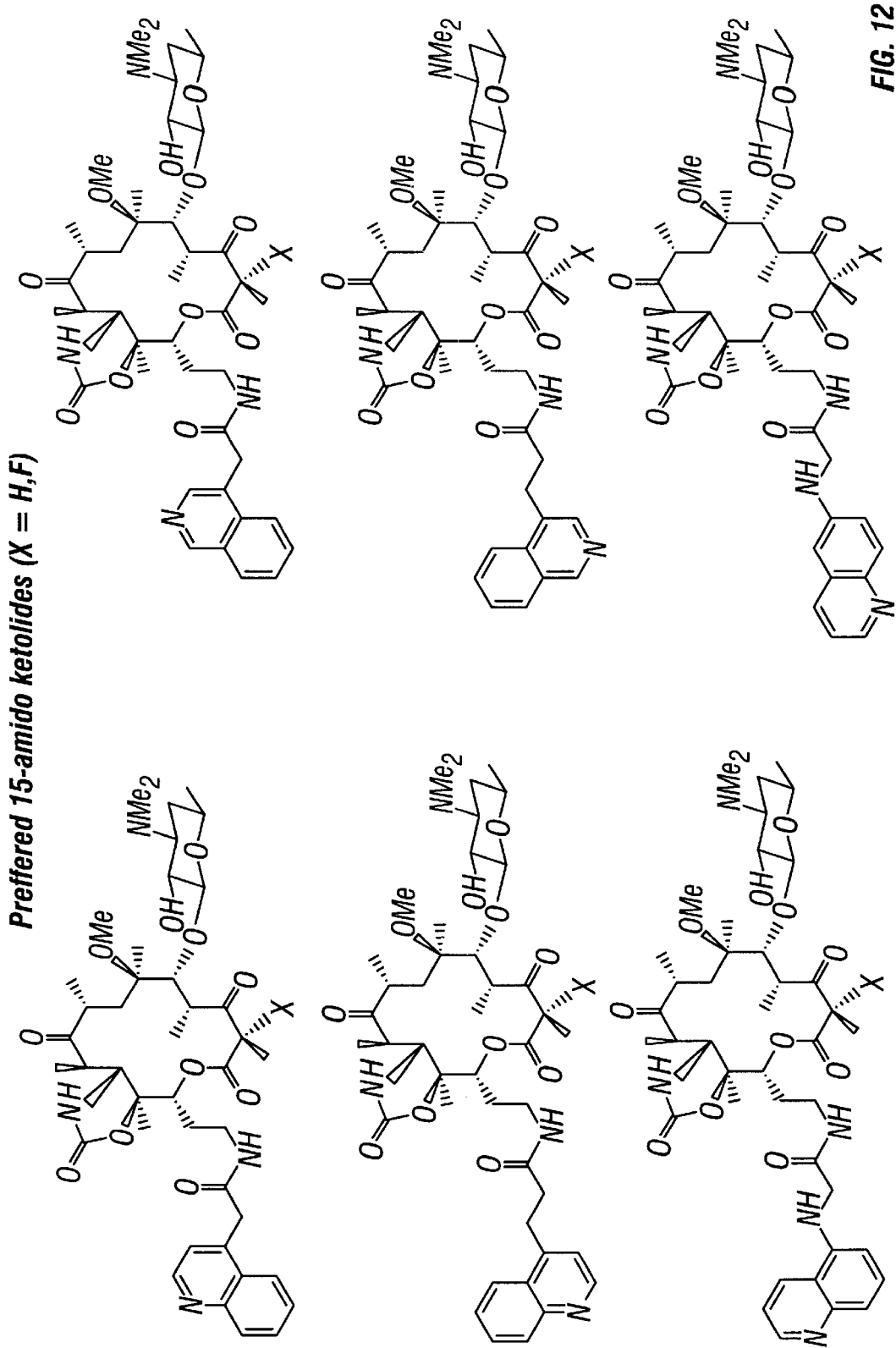
FIG. 12 shows structures of particularly preferred examples of 15-amido-6-O-alkyl-ketolide 11,12-cyclic carbamates. In each case, X may be either H or F.

Preferred 15-amido ketolides, 15-ethenyl ketolides and other preferred arylsubstituted ketolides are shown in FIGS. 12 and 15.

Further, in one embodiment of compound (1) T is not N(R). In another embodiment of compound (1) T—L—O does not form a carbamate ring.

Synthesis of the Invention Compounds

As described above, the antibiotic starting materials for any further chemical synthesis are prepared, preferably, by feeding a suitable diketide to a microorganism modified to contain an expression system for the 6-dEB PKS containing a KS1 knockout, or by a host cell that provides a methyl at the 13-position, followed by providing the resulting polyketide to a recombinant strain of *Saccharopolyspora erythraea* that has been altered to eliminate production of 6-dEB. A strain can be prepared that is able to hydroxylate both the 6- and 12-positions or the 12-position only. In the latter case, —$OR_a$ is replaced by —H. The recombinant *S. erythraes* strain, K40-67, is obtained by transforming an *S. erythraes* strain that produces high levels of erythromycin A with a plasmid comprising a mutated eryA1 sequence encoding an inactivated KS1 domain. By homologous recombination, the resulting transformants now are unable to produce 6-dEB as a competitor to the substrate polyketide and, instead, hydroxylate the 6-position and 12-position and glycosylate the 3-position and 5-position of the modified polyketide that has been made in Streptomyces or other polyketide-producing transformant. If a macrolide having only the 12-position, and not the 6-position hydroxylated is desired ($OR_a$ is replaced by H), an *S. erythraes* strain is constructed by disrupting the eryF hydroxylase gene in strain K40-67. Alternatively, the eryK gene can be disabled, wherein embodiments of compounds (1)–(3) may readily be produced.

Formation of the compounds of formulas (1)–(3) requires the production of the erythronolide having a hydroxyl at the 12-position. The starting material may include any of the compounds (4)–(6):

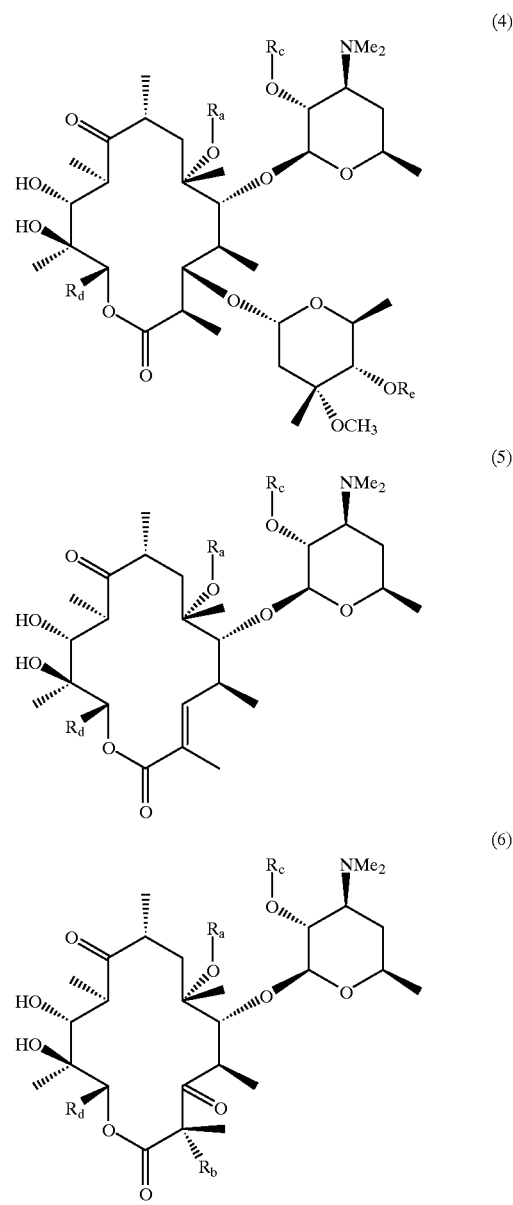

The glycosylation reactions for the production of the erythromycins result in the diglycosylated forms analogous to the compounds set forth in formula (4) herein. If the compounds of formula (4) are to be prepared from the initial product, the hydroxyl group of the cladinose ring (attached to position 3) may then need to be protected for subsequent modification of the macrolide substituents.

The modified erythromycins of the invention, in addition to modification at C-13, contain an —OH group at position 6 unless $OR_a$ is replaced by H as described above. To construct, ultimately, the compounds of formulas (1), (2) and (3) where position 6 is $OR_a$, the compound of formula (I) (see FIG. 1) is provided with protecting groups which form one embodiment of $R_c$ and $R_e$. Such protection is effected using suitable protecting reagents such as acetic anhydride, benzoic anhydride, benzochloro formate, hexamethyldisilazane, or a trialkylsilyl chloride in an aprotic solvent. Aprotic solvents include, for example, dichloromethane, chloroform, tetrahydrofuran, N-methyl pyrrolidone, dimethyl sulfoxide (DMSO), dimethyl formamide (DMF) and the like. Mixtures may also be used. Protection of both sugar hydroxyls in formula (I) may be done simultaneously or sequentially.

In addition to protecting the 2' and 4" hydroxyl groups of the two glycose residues, the keto group at position 9 of the macrolide ring must also be protected. Typically, this is effected by converting the keto group to a derivatized oxime. Particularly preferred embodiments for R in the formula =NOR include unsubstituted or substituted alkyl (1–12C), substituted or unsubstituted aryl (6–10C), alkyl (1–12C), substituted or unsubstituted heteroaryl (6–10C), alkyl (1–12C), and heteroalkyl (such as substituents of the formula $CR'_2OR$ wherein each R', in addition to being independently embodied as R as set forth above, may, together with the other, form a cycloalkyl ring (3–12C)). A preferred derivatized oxime is of the formula =NOR wherein R is isopropoxycyclohexyl.

With the 9-keto group and the 2' and 4" hydroxyls protected, it is then possible to alkylate the 6-hydroxy group in the compound of formula (I) by reaction with an alkylating agent in the presence of base. Alkylating agents include alkyl halides and sulfonates. For example, the alkylating agents may include methyl tosylate, 2-fluoroethyl bromide, cinnamyl bromide, crotonyl bromide, allyl bromide, propargyl bromide, and the like. The alkylation is conducted in the presence of base, such as potassium hydroxide, sodium hydride, potassium isopropoxide, potassium t-butoxide, and an aprotic solvent.

The choice of alkylating agent will depend on the nature of the substituents $R_a$ to be included. As set forth above, $R_a$ can be substituted or unsubstituted alkyl (1–10C), substituted or unsubstituted alkenyl (2–10C), or substituted or unsubstituted alkynyl (2–10C). Particularly preferred are unsubstituted alkyl, alkenyl, or alkynyl, or substituted forms of these wherein the substituents include one or more halogen, hydroxy, alkoxy (1–6C), oxo, $SO_2R$ (1–6C), $N_3$, CN, and $NR_2$ wherein R is H, substituted or unsubstituted alkyl (including cycloalkyl) (1–12C), substituted or unsubstituted alkenyl (including cycloalkenyl) (2–12C), alkynyl (including cycloalkynyl) (2–12C), substituted or unsubstituted aryl (6–10C), including the hetero forms of the above.

Especially preferred are methyl, allyl and ethyl.

Once the alkylation of the 6-hydroxyl is completed, the sugar residues and the macrolide ring may be deprotected. Deprotection of the glycoside moieties is conducted as described by Green, T. W., et al., in *Protective Groups in Organic Synthesis*, infra. Similar conditions result in converting the derivatized oxime to =NOH. If formation of the underivatized oxime is not concurrent with deprotection, the conversion to the oxime is conducted separately.

The oxime can then be removed and converted to a keto group by standard methods known in the art. Deoximating agents include inorganic sulfur oxide compounds such as sodium hydrogen sulfite, sodium pyrosulfate, sodium thiosulfate, and the like. In this case, protic solvents are used, such as water, methanol, ethanol, isopropanol, trimethyl silanol and mixtures of these. In general, the deoximation reaction is conducted in the presence of an organic acid.

At this point in the process, or later, after the compound of formula (4) has been converted to the compounds of formulas (5) or (6) or to any of compounds (1)–(3), as further described below, the group introduced at the 6-hydroxyl can further be manipulated. Conveniently, the initial substitution may provide a 6—O-allyl, i.e., O—$CH_2CH=CH_2$, which can further be derivatized by reduction to give the 6-O propyl compound, or be treated with osmium tetroxide to provide the 2,3-dihydroxypropyl compound, which can further be esterified at each oxygen atom. The O-allyl derivative can also be oxidized with m-chloroperoxybenzoic acid in an aprotic solvent to provide the epoxy compound which can be opened with amines or N-containing heteroaryl compounds to provide compounds with N-containing side-chains, or can be oxidized under Wacker conditions to provide the substituent O—$CH_2$—C (O)—$CH_3$, or can be ozonized to provide the aldehyde. The aldehyde can then be converted to the oxime or reacted with a suitable amine and reduced in the presence of a borohydride reducing agent to provide an amine. The oxime can also be converted to a nitrile by reaction with a dehydration agent in an aprotic solvent. The O-allyl derivative can also be reacted with an aryl halide under Heck conditions (Pd(II) or Pd(O), phosphine and amine or inorganic base) to provide a 3-aryl prop-2-enyl derivative. This derivative can then be reduced with hydrogen and palladium on carbon to provide a 3-arylpropyl derivative. If the initial substituent $R_a$ is a 2-propyne, similar reactions can be employed to provide alterations in the side-chain, including arylation.

In order to convert the compound of formula (4) into the compound of formula (6), by first removing the cladinose moiety, the compound of formula (4) is treated with mild aqueous acid or with a deglycosylating enzyme. Suitable acids include hydrochloric, sulfuric, chloroacetic, trifluoroacetic and the like, in the presence of alcohol. Reaction times are typically 0.5–24 hours at a temperature of –10–35° C. During this reaction, the 2' group of the remaining sugar is protected as set forth above and deprotected subsequent to the decladinizing reaction. The resulting hydroxyl group at the 3-position of the macrolide ring is then oxidized to the ketone using a modified Swern oxidation procedure. In this procedure, an oxidizing agent such as N-chlorosuccinimide-dimethyl sulfide or a carbodiamide-dimethylsulfoxide is used. Typically, a compound of formula (4) is added to pre-formed N-chlorosuccinimide and dimethyl sulfide complex in a chlorinated solvent such as methylene chloride at –10–25° C. After being stirred for 0.5–4 hours, a tertiary amine such as triethylamine is added to produce the corresponding ketone and the 2' protecting group is then removed.

In order to halogenate the macrolide at position 2 (converting $R_b$=H to halogen), the compound of formula (6), where $R_b$=H, is treated with a base and an electrophilic halogenating reagent such as pyridinium perbromide or N-fluorobenzenesulfonimide. Position 2 can be halogenated at any time after the 3 keto compound is prepared and preferably after the 11,12 ring is formed.

Figure 10:
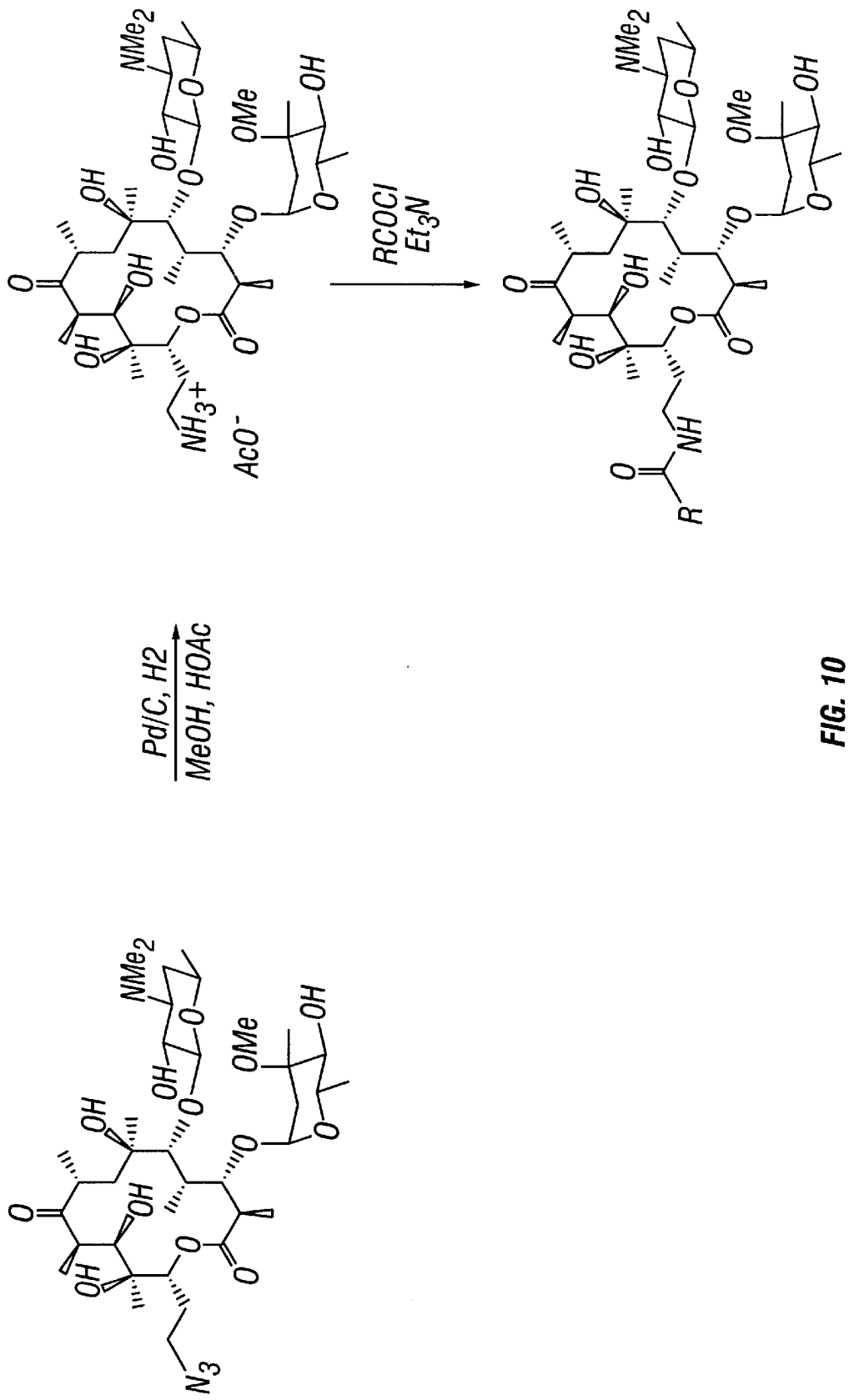
FIG. 10 illustrates the conversion of 15-azidoerythromycin A into 15-amidoerythromycins.
Figure 14:
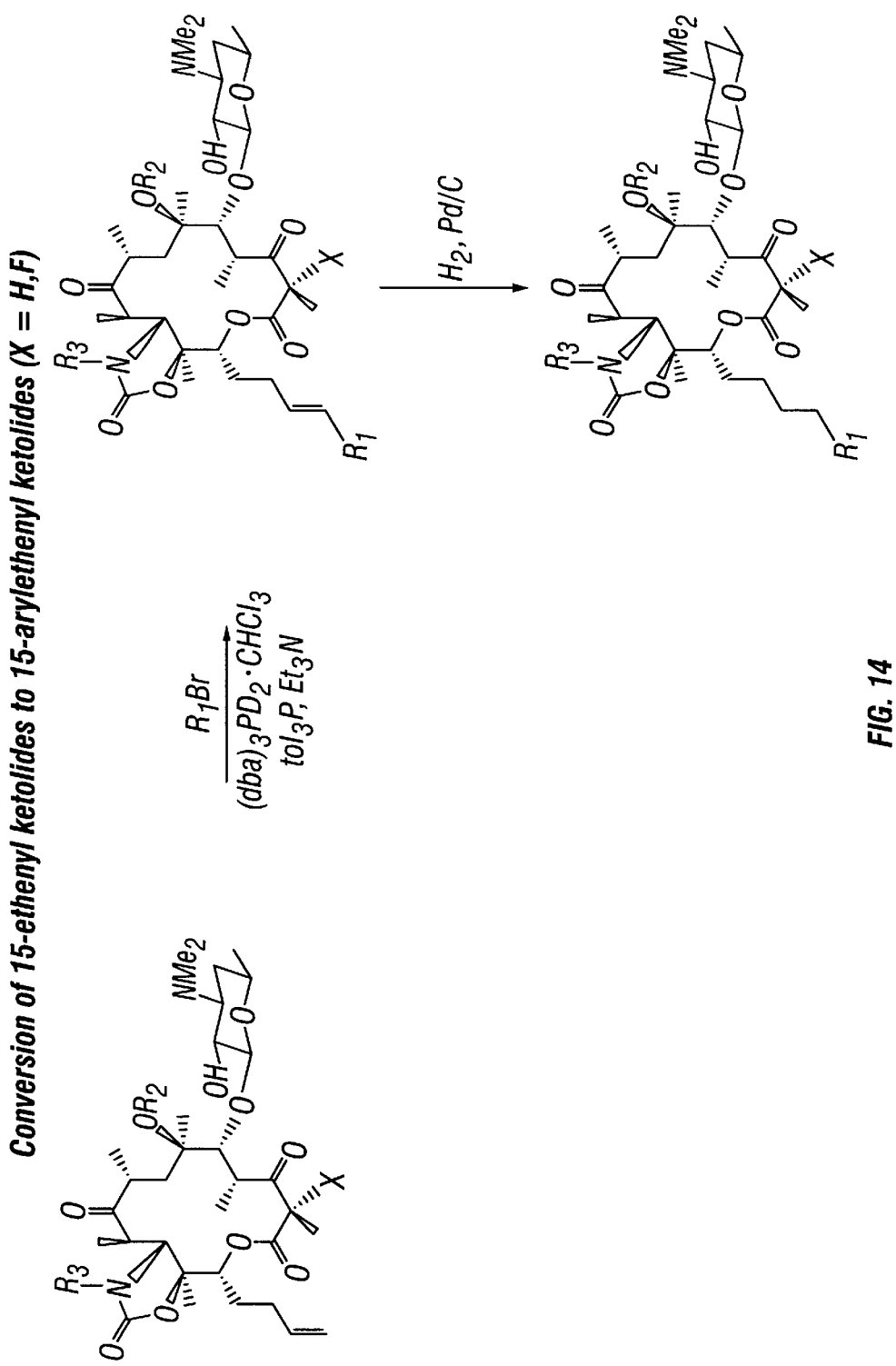
FIG. 14 illustrates the attachment of aromatic groups onto the ethenyl moiety of 15-ethenylketolides to form 15-(2-arylethenyl)ketolides, and optional hydrogenation to form the 15-(2-arylethyl)ketolides.

The appropriate substituent such as vinyl, ethenyl, butenyl or azido at the C-13 position can be further manipulated. For example, an amidoacetate salt of the compound of the invention can be derivatized using an arylacetyl chloride to yield an arylamino alkyl group on the C-13 position as illustrated in FIG. 10. Preferably the C13 derivatives of an azido group take place before the ketolide is formed. Derivations of an alkenyl group such as ethenyl can take place either before or after the ketolide is formed and preferably after the 11,12 ring is formed, as shown in FIGS. 14 and 16.

In order to obtain the compounds of formula (5), the compound resulting from the deglycosylation reaction of formula (4) is treated with a dehydrating agent such as carbonyl diimidazole and base.

Intermediates (7)–(9) can then be prepared from intermediates (4)–(6).

(7)

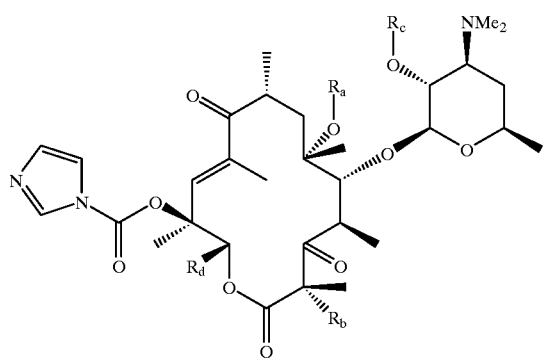

(8)

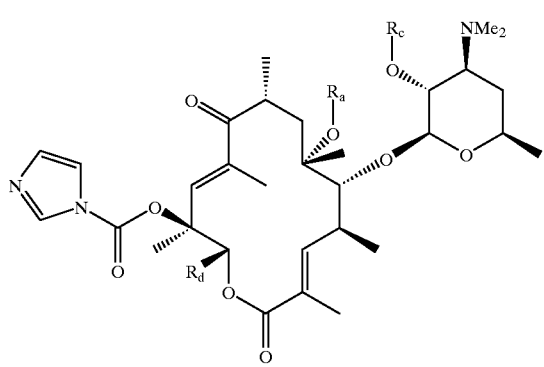

(9)

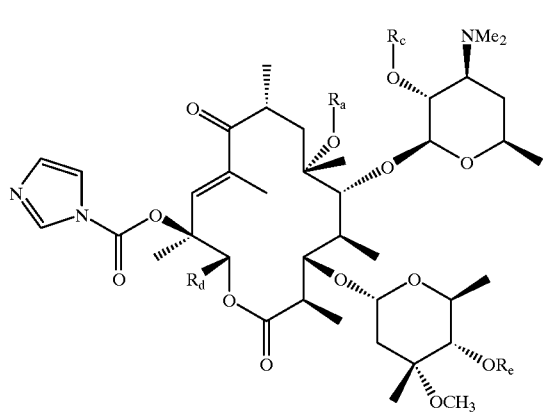

It will be noted that the presence of the 12-hydroxyl group is required. The hydroxyl groups of the sugar moieties are protected as described above and the resulting protected compounds are then reacted with sodium hexamethyldisilazide and carbonyldiimidazole which results in dehydration to obtain a π-bond at position 10-11 and derivatization of the 12-hydroxyl to provide functionality in the macrolide ring as shown in compounds (7)–(9). FIG. 2 illustrates the reaction sequence from compound (4) to compound (9) in the first step.

Reaction of compounds (7)–(9) with aqueous ammonia provides a compound of formulas (1)–(3) wherein L is carbonyl and T is NH as shown in FIG. 2 for compounds (9) and (3) in the second step.

Reaction of compounds (7)–(9) with compounds of the formulas $H_2NR$, $H_2NOR$, $H_2NNHCOR$, $H_2NN=CHR$ or $H_2NNHR$, where R is H or $R_a$, provides the corresponding compounds of formulas (1)–(3) wherein T is nitrogen derivatized as described with the $R_f$ substituents including —R, —OR, —NHCOR, —N=CHR or —NHR. In FIG. 2, $R_f$ is H because ammonia is used. These are compounds of the formulas (10)–(12):

(10)

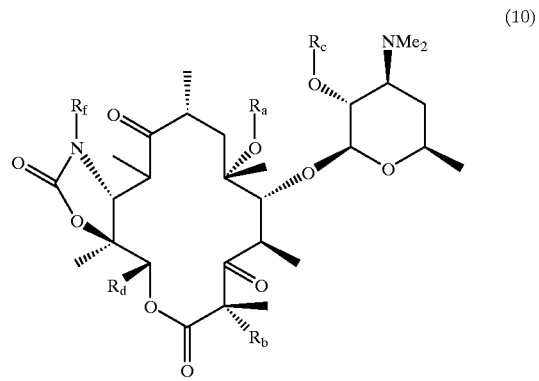

(11)

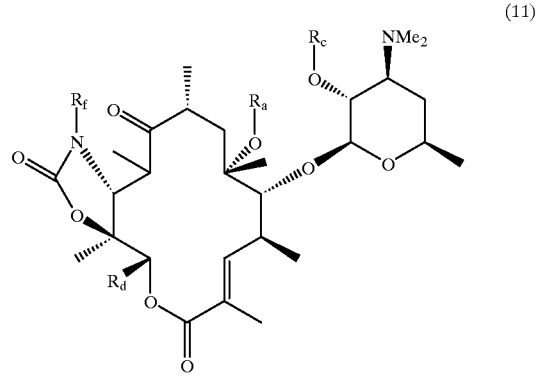

(12)

Figure 3:
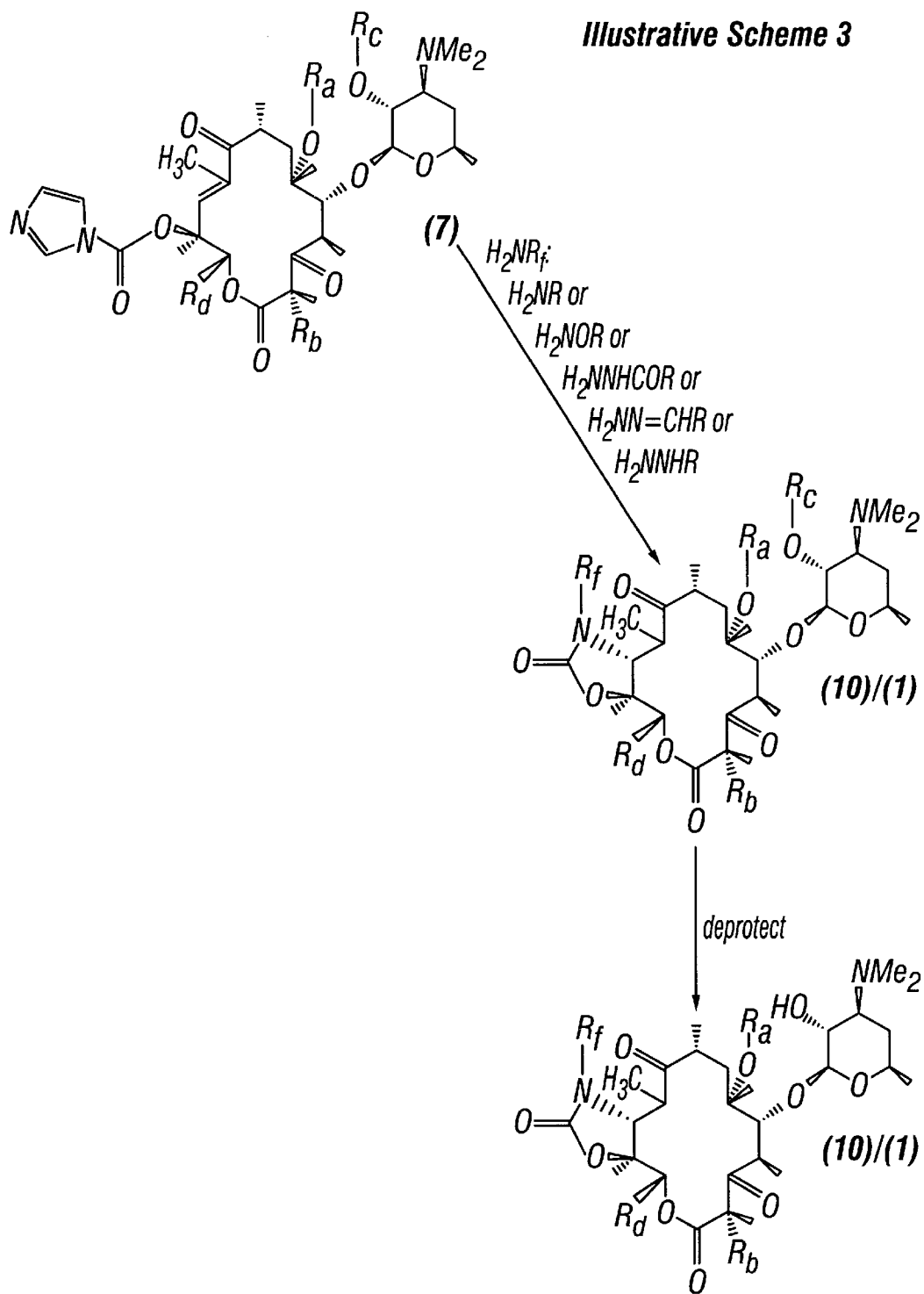
FIG. 3 shows a schematic of an alternate synthesis of the compounds of the invention from the intermediate compound (7).

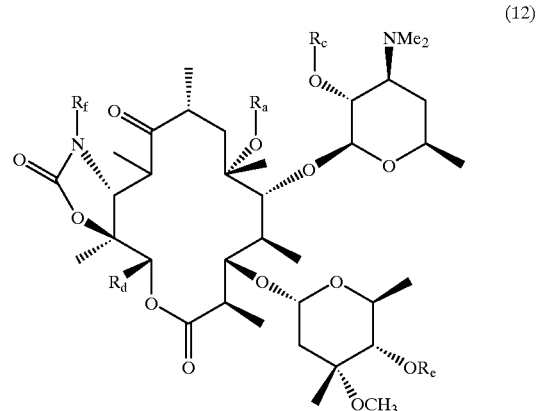

where $R_f$ represents the substituents on the nitrogen as described above. FIG. 3 analogously depicts the reaction of compound (7) with $H_2NR_f$ to form compound (10). The preparation follows the procedure described by Baker et al. J Org Chem (1988) 53:2340, which is incorporated herein by reference. In particular, treatment of compound (7) with an amino compound of the formula $H_2N-R_f$ results in formation of the cyclic carbamate in which $R_f$ is as described above. The protected 2'-hydroxy group can be deprotected as described above.

Alternate or additional procedures may be used to prepare compounds (10)–(12) where $R_f$ is not H.

For example, the compounds of formulas (10)–(12) wherein $R_f$ is H can be reacted with an alkylating agent which is of the formula R-halogen to replace the hydrogen on the ring nitrogen with an alkyl group.

Further, compounds (10)–(12) that do not contain an acyl group as a substituent on the nitrogen of T can be formed by treatment of such compounds (10)–(12) with an acylating agent selected from the group consisting of R(CO)-halogen or (RCO)$_2$O to give compounds (7)–(9) wherein T is —N— and R$_f$ is —NH—COR.

Treatment of compounds (10)–(12) where R$_f$ is —NH$_2$ with an aldehyde R—CHO, wherein R is as defined previously gives compounds (10)–(12) wherein R$_f$ is —N=CHR.

Treatment of compounds (10)–(12), where R$_f$ is —NH$_2$ with an alkylating agent having the formula R-halogen, wherein R is as defined previously, gives the compounds (10)–(12) where R$_f$ is R.

Of course, if the substrate for the ring formation is a compound of formula (4), a compound of the formula (3) results; modifications can then be conducted to convert the compound of formula (3) to compounds of formulas (1) and (2), as described above. Under these circumstances, the keto group would be protected by a derivatized oxime. Such modifications include removal of the cladinose moiety by acid hydrolysis; oxidizing the 3-hydroxyl group; and deprotecting the protected hydroxyl and keto groups.

Figure 4A:
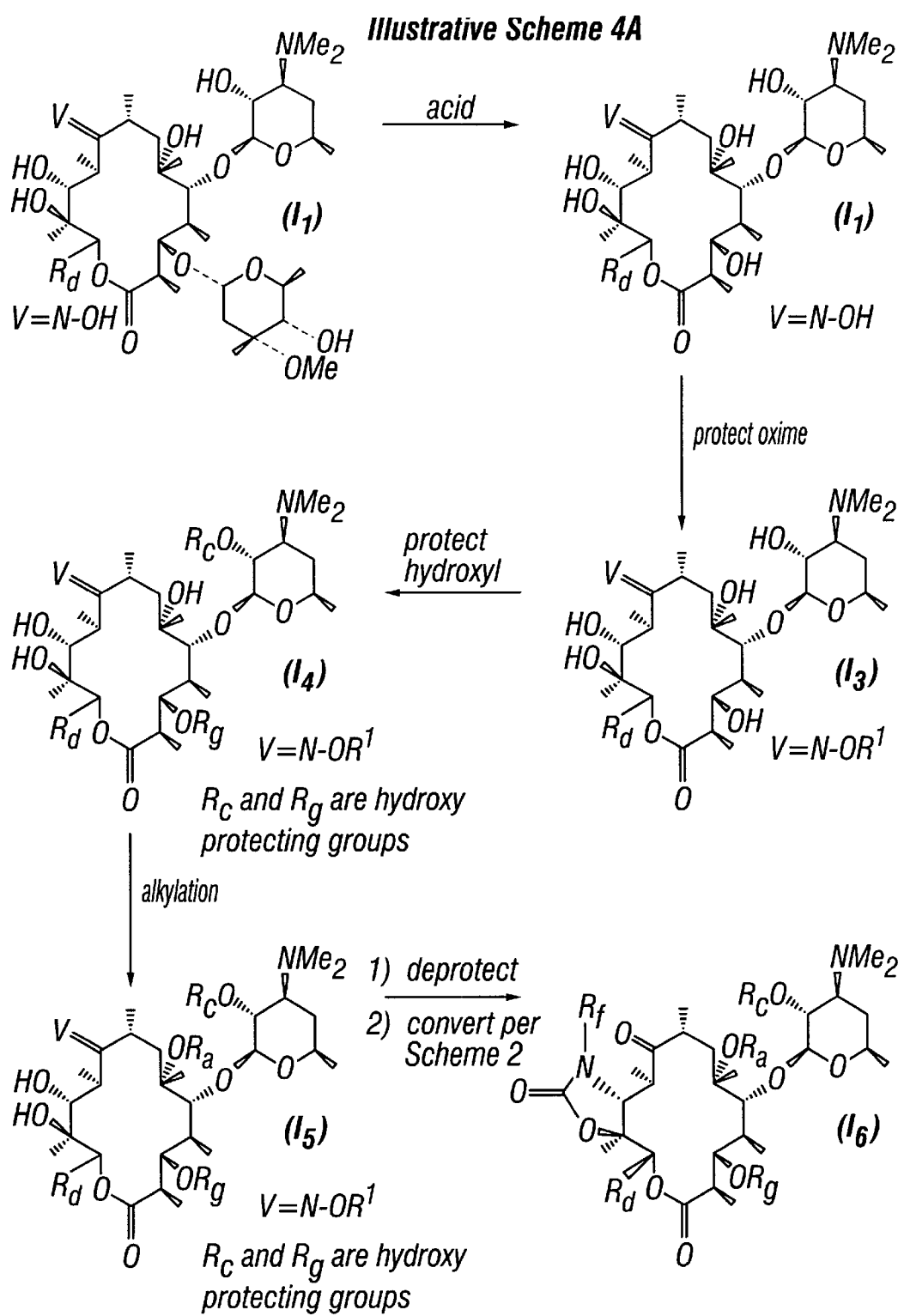
FIGS. 4a and 4b show a schematic of the synthesis of the compounds of the invention.
Figure 4B:
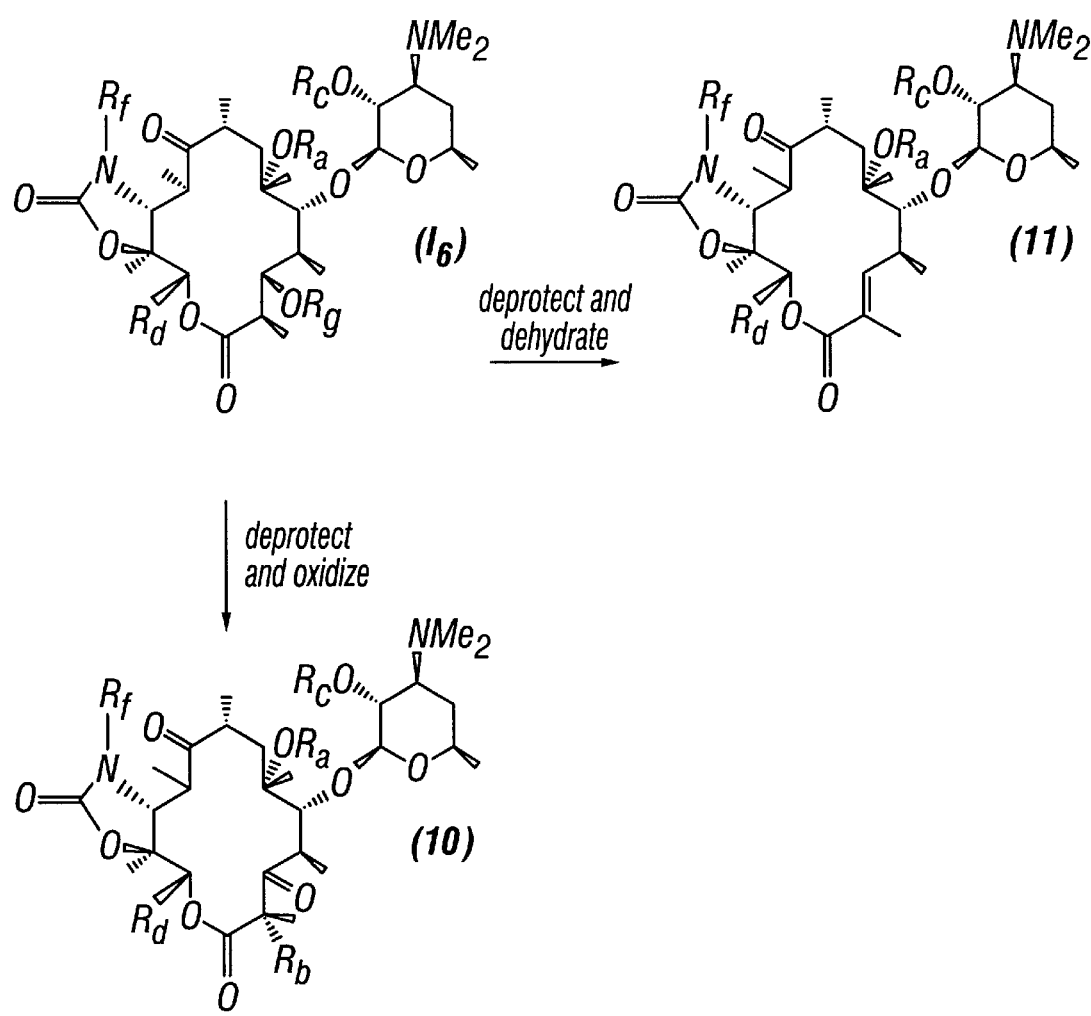

According to the alternate procedure shown in Ilustrated Scheme 4a FIG. 4a), the intermediate compound (I$_1$), which is the 9-oxime compound of erythromycin A, is subjected to acid hydrolysis with dilute mineral or organic acid as described previously to remove the cladinose moiety and give intermediate compound (I$_2$). The oxime compound (I$_2$) is then converted to the protected oxime compound (I$_3$) wherein V is =N—O—R$^1$ where R$^1$ is a protecting group, by reaction with the appropriately substituted oxime protecting reagent. The 3 and 2'-hydroxy groups of (I$_3$) are then protected, preferably with a trimethylsilyl protecting group, to give compound (I$_4$). Compound (I$_4$) is then alkylated as described previously to give compound (I$_5$), and compound (I$_5$) is first deoximated as described above then the deoximated product is converted to the compound (I$_6$) by the procedures described for preparation of compound (3) from compound (4) in Illustrated Scheme 2. FIG. 4b shows compound (I$_6$) is then deprotected and oxidized to the 3-ketolide derivative, compound (10) of the invention, wherein L is CO and T is —NR$_f$ by procedures described previously. Intermediate compound I$_6$ can also be deprotected and dehydrated to form compound (11) of the invention, also shown in FIG. 4b.

As mentioned earlier, the 6-position substituent can be manipulated after the compounds (1)–(3) are formed. For example, compound (10) can be prepared wherein R$_a$ is —CH$_2$—CH—N—OR$_h$, and R$_h$ is H or C$_1$–C$_3$-alkyl, aryl substituted C$_1$–C$_3$-alkyl, or heteroaryl substituted C$_1$–C$_3$-alkyl. In this method, compound (10), wherein R$_a$ is —CH$_2$—CH=CH$_2$, is treated with ozone to form compound (10) wherein R$_a$ is —CH$_2$—CH=O.

The compound (10) wherein R$_a$ is —CH$_2$—CH=O is further treated with a hydroxylamine compound having the formula NH$_2$—O—R$_h$, wherein R$_h$ is as previously defined; and optionally deprotecting, and isolating the desired compound. In a preferred embodiment of the process immediately above, R$_f$ is H.

In another embodiment of the invention is a process for preparing a compound (10) wherein R$_a$ is —CH$_2$—CH$_2$—NH—R$_i$ where R$_i$, with the atom to which it is attached, form a 3–10 membered substituted or unsubstituted heterocycloalkyl ring.

The method comprises reductively aminating compound (10) wherein R$_a$ is —CH$_2$—CH=O with an amine compound having the formula —NH$_2$—R$_i$, wherein R$_i$ is as previously defined; and optionally deprotecting, and isolating the desired compound.

Compounds of the formulas (1)–(3) where L is carbonyl and T is —O— or wherein L is methylene and T is —O—, are prepared from compounds (4)–(6) using the procedure described by Baker et al., *J Org Chem* (1988) 53:2340 which is incorporated herein by reference. The 2' or 2',4"-protected compounds of formulas (4)–(6) are first converted to the cyclic carbonates by reaction with carbonyldiimidazole and sodium hexamethyldisilazide.

Compounds (13)–(15) represent compounds (1)–(3) where L is methylene and T is —O—:

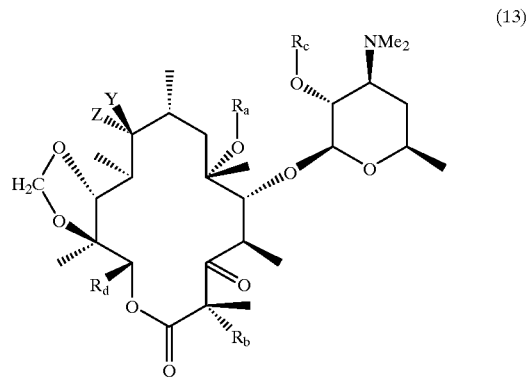

(13)

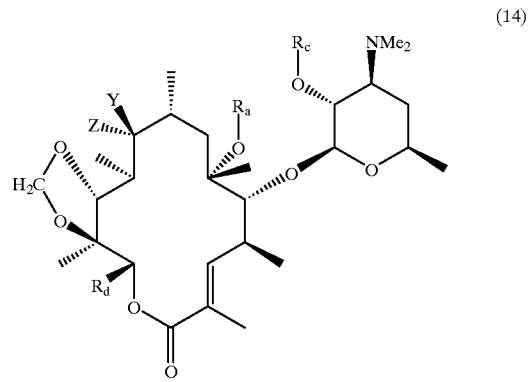

(14)

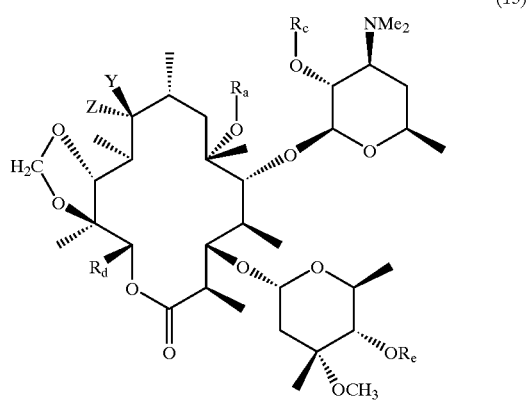

(15)

Figure 5:
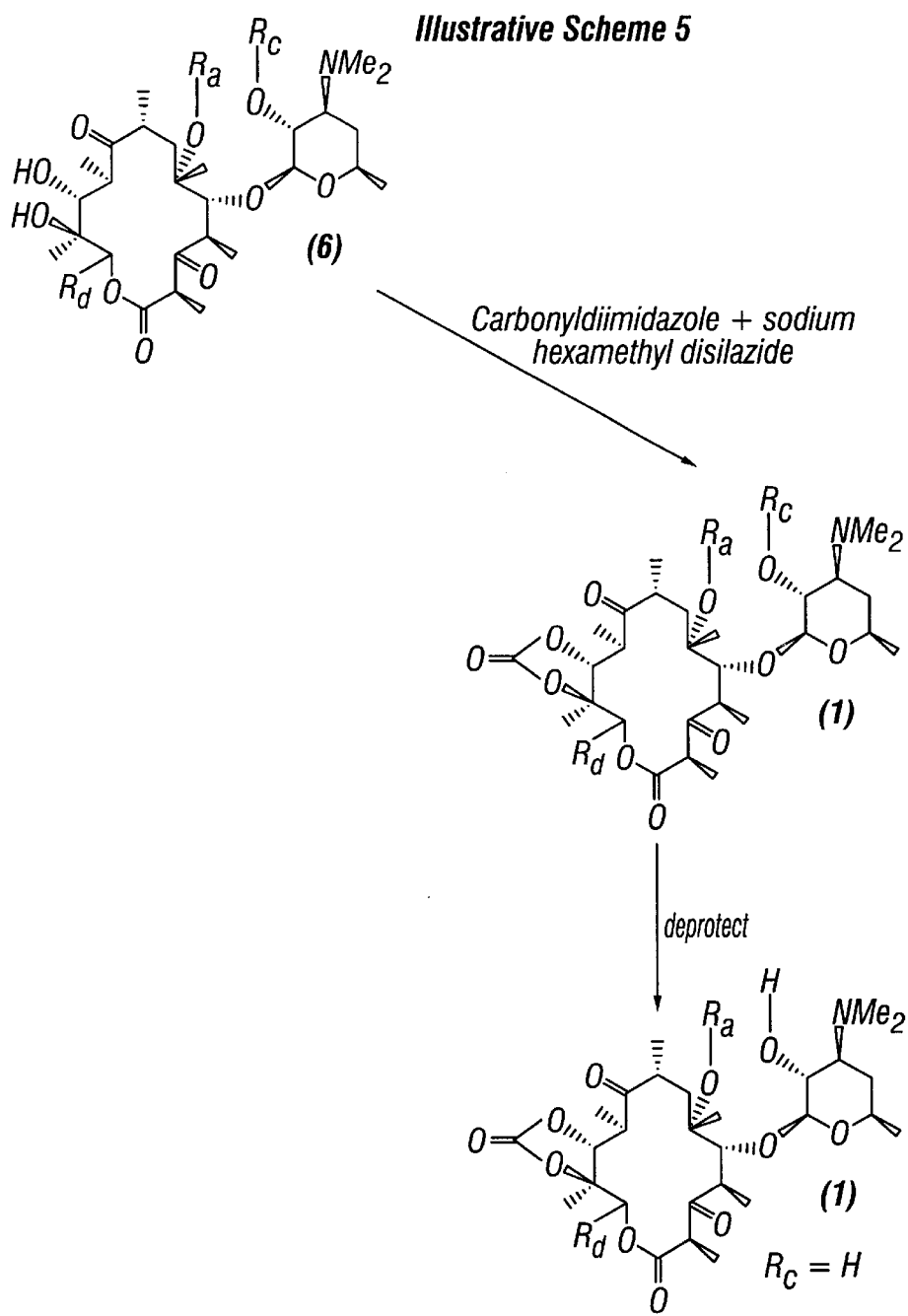
FIG. 5 shows a schematic of the synthesis of the inventive compounds wherein T is —O—.
Figure 6:
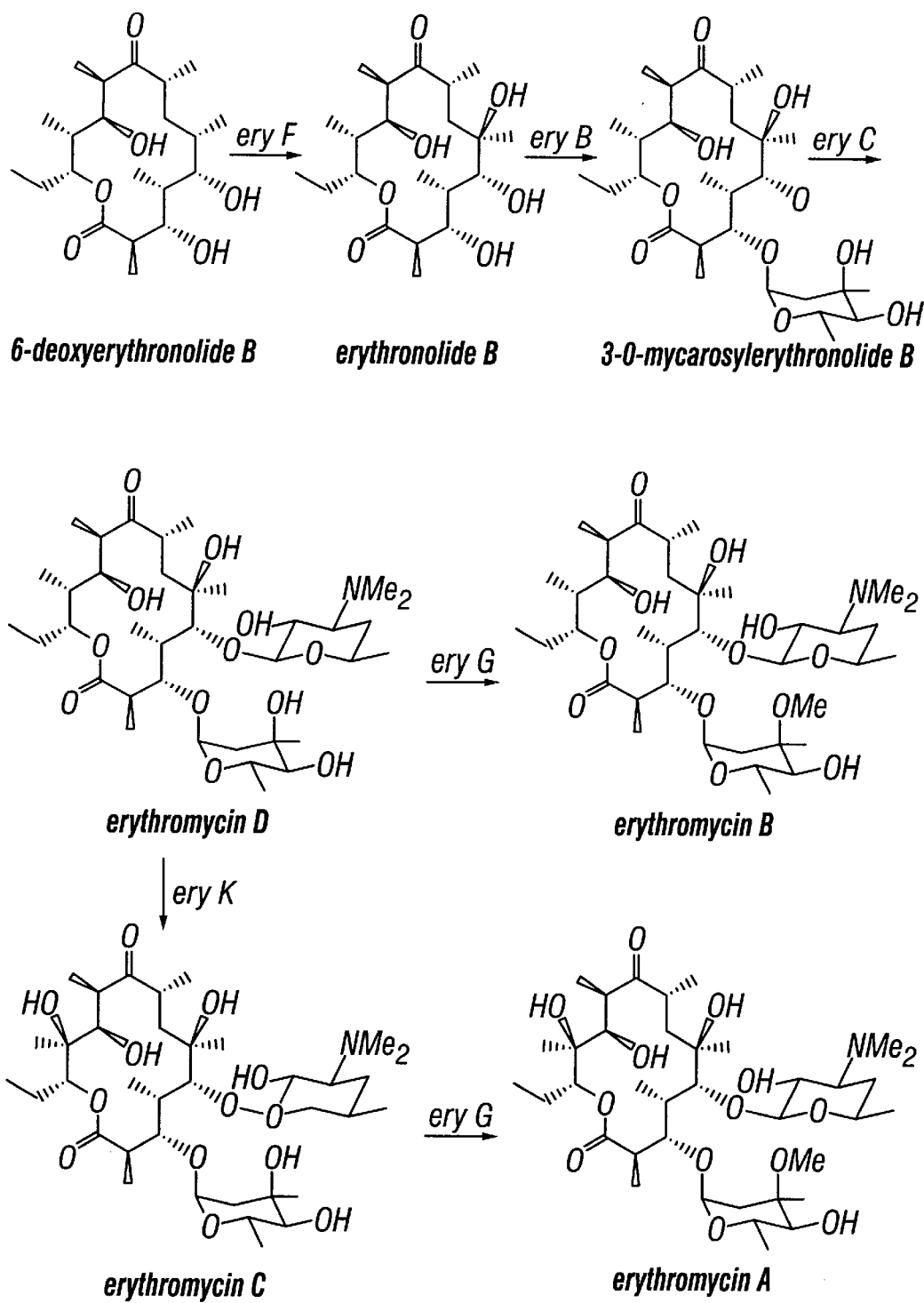
FIG. 6 shows the post-PKS biosynthesis of erythromycins. This pathway is employed in the present invention, as shown in FIG. 1.
Figure 11A:
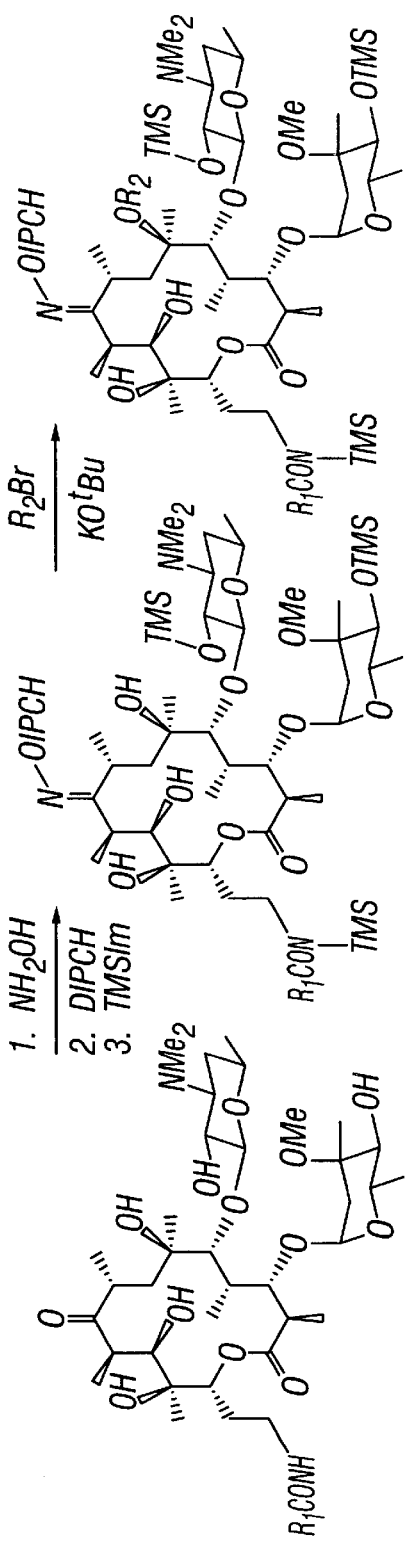
FIG. 11 illustrates the conversion of 15-amidoerythromycins into the corresponding 15-amido-6-O-alkyl-ketolide 11,12-cyclic carbamates.
Figure 11A:
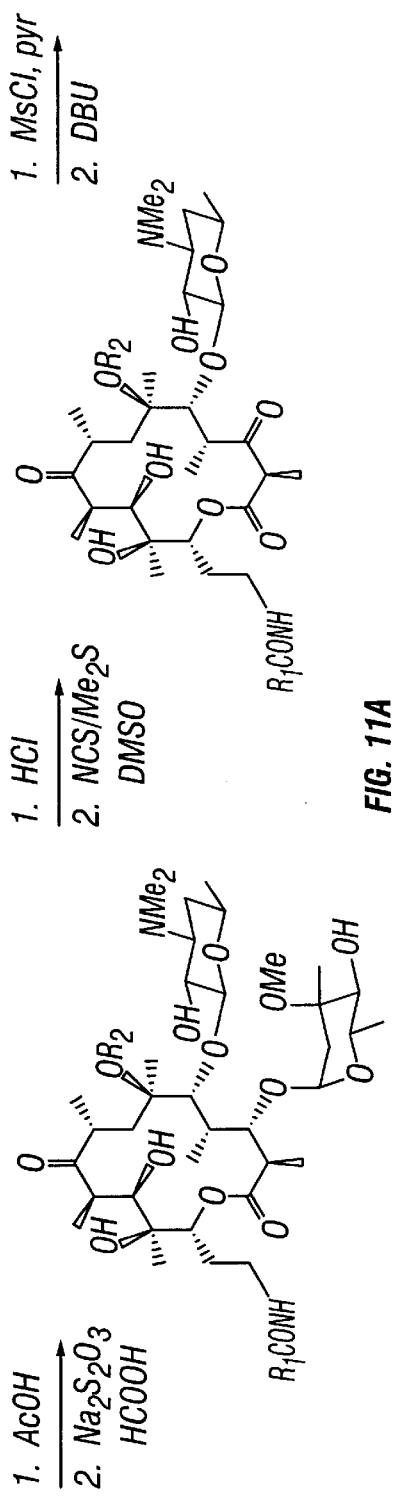
Figure 11B:
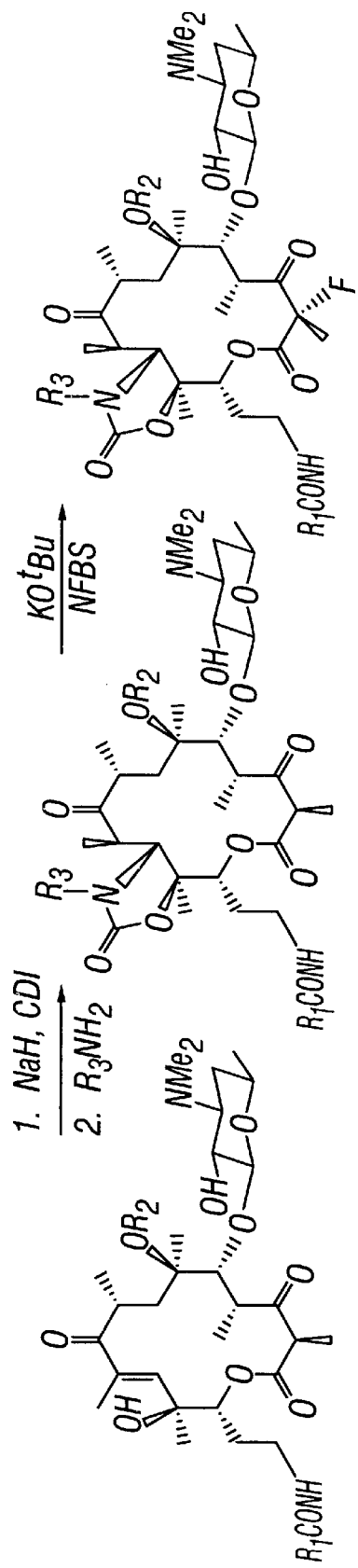
Figure 13A:
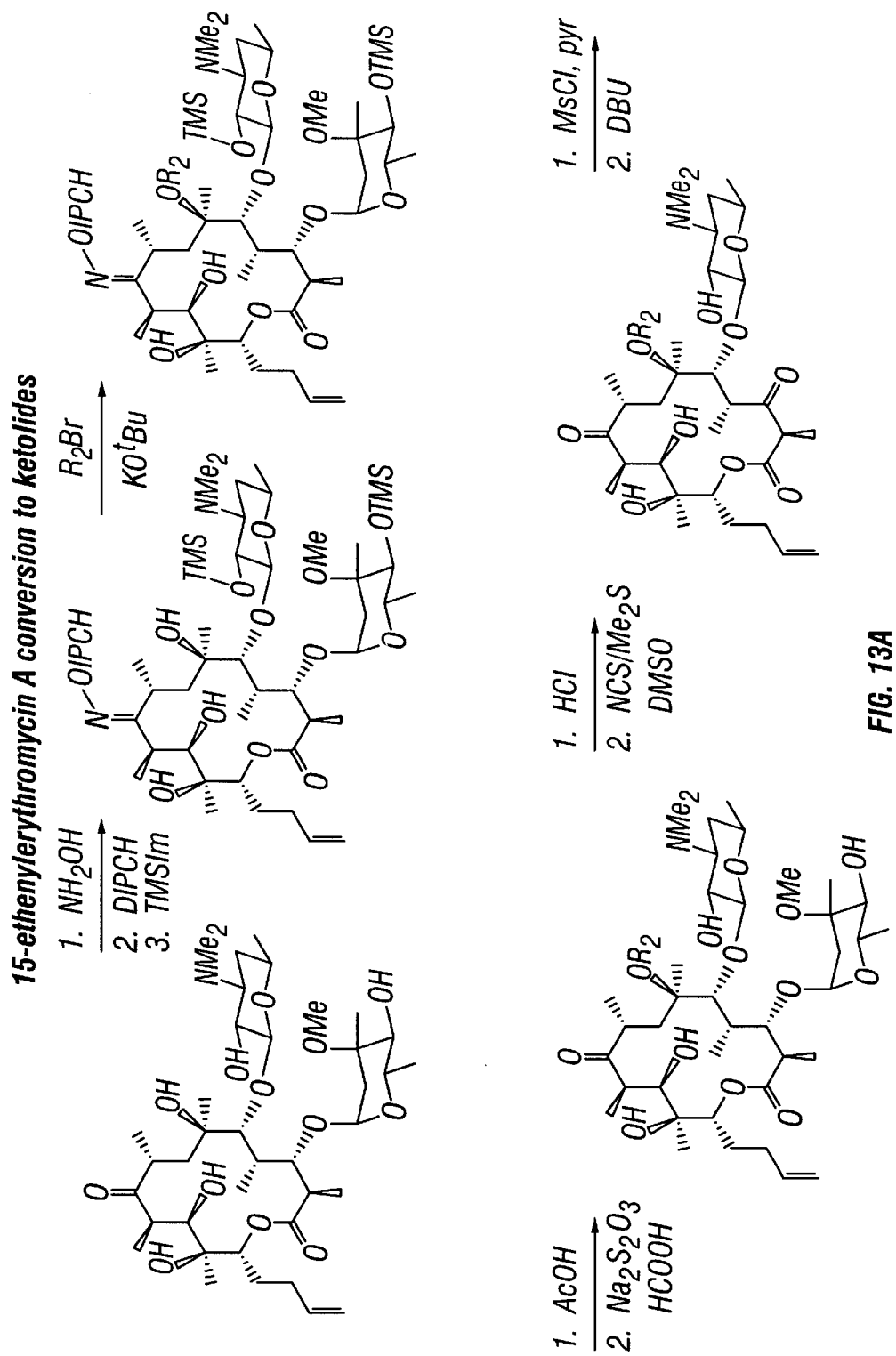
FIG. 13 illustrates the conversion of 15-ethenylerythromycin A into the 15-ethenyl-6-O-alkyl-ketolide 11,12-cyclic carbamates, as well as optional fluorination at C2.
Figure 13B:
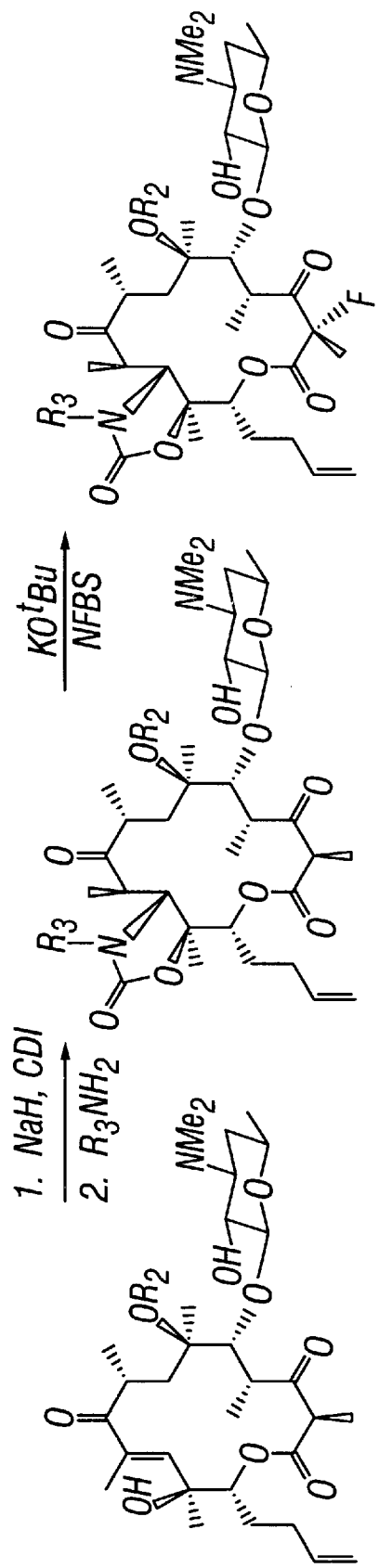

Illustrative Scheme 5 in FIG. 5 illustrates the conversion of the compound having formula (6) to the compound having the formula (1). FIGS. 11 and 13 illustrate the conversion of erythromycins to ketolides.

In order to prepare compounds of formulas (4)–(6) or (1)–(3) wherein one of Z and Y is H and the other OH or protected OH or is an amino derivative as described above, either the carbonyl or oxime or derivatized oxime is reduced using a suitable reducing agent. Substituted amines are obtained by alkylation.

Novel methods of synthesis of the compounds of the invention are also provided.

Exemplary Embodiments

The compounds of formulas (1), (2) and (3) are defined by their various substituents. Table 1 illustrates compounds within the scope of the present invention which are:
of formula (1) wherein $R_b$ is H, F, Cl, or Br, L is CO, and $R_c$ is H;
of formula (2) wherein $R_c$ is H and L is CO; and
of formula (3) wherein $R_c$ is H, L is CO, and $R_e$ is H.

TABLE 1

| $R_d$ | $R_a$ | Y | Z | T |
|---|---|---|---|---|
| —CH₃ | —CH₂CH₂—φ | =O |  | —NH— |
| —CH=CH₂ | —CH₂CH=CH-φ | =O |  | —N(CH₃)— |
| —CH₂CH₂CH₃ | —CH₂CH₂NHCH₃ | =NOH |  | —N(NHCH₃)— |
| —CH₃ | —CH₂CHOHCH₃ | =NOCH₂CH₃ |  | —N(OCH₃)— |
| —CH(CH₃)₂ | —CH₂—φ | H | OH | —N(N=CH₂)— |
| —CH₃ | —CH₂—CH=CH₂ | =O |  | —O— or —NH— |
| —CH₃ | —CH₂—CH=CH—(3-quinolyl) | =O |  | —O— or —NH— |
| —CH₃ | —CH₂—CH₂—CH₂—(3-quinolyl) | =O |  | —O— or —NH— |
| —CH₃ | —CH₂—CH=CH—(2-methyl-6-quinolyl) | =O |  | —O— or —NH— |
| —CH₃ | —CH₂—CH=CH—(5-isoquinolyl) | =O |  | —O— or —NH— |
| —CH₃ | —CH₂—CH=CH—(3-bromo-6-quinolyl) | =O |  | —O— or —NH— |
| —CH₃ | —CH₂—C=CH—(6-methoxy-2-naphthyl) | =O |  | —O— or —NH— |
| —CH₃ | —CH₂—C≡C—(2-phenylethenyl) | =O |  | —O— or —NH— |
| —CH₃ | —CH₂—C≡C—(3-quinolyl) | =O |  | —O— or —NH— |
| —CH₃ | —CH₂—C≡C—naphthyl | =O |  | —O— or —NH— |
| —CH₃ | —CH₂—C≡C—(6-methyl-2-naphthyl) | =O |  | —O— or —NH— |
| —CH₃ | —CH₂—C≡C—(3-(2-furanyl)-6-quinolyl) | =O |  | —O— or —NH— |
| —CH=CH₂ | —CH₃ | =O |  | —O— or —NH— |
| —CH₂OH | —CH₂—C=CH—(4-fluorophenyl) | =O |  | —O— or —NH— |
| —CH₂OH | —CH₂—C=CH-(3-quinolyl) | =O |  | —O— or —NH— |
| —CH₂OH | —CH₂—C=CH—(6-quinolyl) | =O |  | —O— or —NH— |
| —CH₂OCH₃ | —CH₂—C=CH—(3-pyridyl) | =O |  | —O— or —NH— |
| —CH₂CH₂CH₃ | —CH₂—C=CH—(3-quinolyl) | =O |  | —O— or —NH— |
| —CH₂CH₂CH₃ | —CH₂—C=CH—(6-chloro-3-quinolyl) | =O |  | —O— or —NH— |
| —CH₂CH₂CH₃ | —CH₂—C=CH—(4-quinolyl) | =O |  | —O— or —NH— |
| —CH₂CH₂CH₃ | —CH₂—C=CH—(6-chloro-3-quinolyl) | =O |  | —O— or —NH— |
| —CH₂CH₂CH₃ | —CH₂—C=CH—(6-hydroxy-3-quinolyl) | =O |  | —O— or —NH— |
| —CH₂CH₂CH₃ | —CH₂—C=CH—(6-methoxy-3-quinolyl) | =O |  | —O— or —NH— |
| —CH₂CH₂CH₃ | —CH₂—C=CH—(6-aminocarbonyl-3-quinolyl) | =O |  | —O— or —NH— |
| —CH₂CH₂CH₃ | —CH₂—C=CH—(3-(2-thiophenyl)-6-quinolyl) | =O |  | —O— or —NH— |
| —CH₂CH₂CH₃ | —CH₂—C=CH—(6-hydroxy-2-naphthyl) | =O |  | —O— or —NH— |
| —CH₂CH₂CH₃ | —CH₂—C≡C—(3-quinolyl) | =O |  | —O— or —NH— |
| —CH₂CH₂CH₃ | —CH₂—C≡C—(6-chloro-2-naphthyl) | =O |  | —O— or —NH— |
| —CH₂CH₂CH₃ | —CH₂—C≡C—(6-quinolyl) | =O |  | —O— or —NH— |
| —CH₂CH₂CH₃ | —CH₂CH₂NHCH₂CH₂—(2-chlorophenyl) | =O |  | —O— or —NH— |
| —CH₃ | —CH₂CH₂NH₂ | =O |  | —O— or —NH— |
| —CH₃ | OR$_a$ replaced by H | —NH₂ | H | —O— or —NH— |
| —CH₃ | —CH₃ | —NH₂ | H | —O— or —NH— |
| —CH₃ | OR$_a$ replaced by H | —N(piperazinyl) | H | —O— or —NH— |
| —CH₃ | " | —N(piperidinyl) | H | —O— or —NH— |
| —CH₃ | " | —N(morpholinyl) | H | —O— or —NH— |
| —CH₃ | —CH₂CHClCH₃ | H | —N(piperazinyl) | —O— or —NH— |
| —CH₃ | " | H | —N(piperidinyl) | —O— or —NH— |

TABLE 1-continued

| R_d | R_a | Y | Z | T |
|---|---|---|---|---|
| —CH$_3$ | " | H | morpholine (N-linked, with O) | —O— or —NH— |
| —CH$_3$ | —CH$_3$ | H | piperazine (N-linked, with NH) | —O— or —NH— |
| —CH$_2$CH$_2$CH$_3$ | OR$_a$ replaced by H | H | piperazine (N-linked, with NH) | —O— or —NH— |
| —CH$_2$CH$_2$CH$_3$ | " | —NH$_2$ | H | —O— or —NH— |
| —CH$_2$CH$_2$CH$_3$ | —CHCH(OCH$_3$)CH$_3$ | | H | —O— or —NH— |
| | | piperazine (N-linked, with NH) | | |
| —CH$_2$CH$_2$CH$_3$ | —CH$_3$ | H | piperazine (N-linked, with NH) | —O— or —NH— |
| —CH$_2$CH$_2$CH$_3$ | —CH$_2$CH$_2$CH$_3$ | piperidine (N-linked) | H | —O— or —NH— |
| —CH$_2$CH$_2$CH$_3$ | —CH$_2$CHBrCH$_3$ | H | piperidine (N-linked) | —O— or —NH— |
| —CH$_3$ | —CH$_2$CHOHCH$_3$ | =NOCHCH$_3$ | | —O— or —NH— |
| —CH$_2$CH$_2$CH$_3$ | —CH$_2$CH$_2$CH$_3$ | —NH$_2$ | H | —O— or —NH— |
| —CH$_3$ | —CH$_2$CH=CH$_2$ | =O | | —N(CH$_3$) |
| —CH$_3$ | —CH$_2$CH=CH—(3-quinolyl) | =O | | —N(CH$_3$) |
| —CH$_3$ | —CH$_2$CH=CH$_2$ | =O | | N(CH$_2$CH$_2$N(CH$_3$)$_2$) |
| —CH$_3$ | —CH$_2$CH=CH—(3-quinolyl) | =O | | N(CH$_2$CH$_2$N(CH$_3$)$_2$) |
| —CH$_3$ | —CH$_2$CH=CH$_2$ | =O | | N(CH$_2$CH=CH$_2$) |
| —CH$_3$ | —CH$_2$CH=CH—(3-quinolyl) | =O | | N(CH$_2$CH=C—(3-quinolyl)) |
| —CH$_3$ | —CH$_2$CH=CH$_2$ | =O | | N(NH$_2$) |
| —CH$_3$ | —CH$_2$CH=CH—(3-quinoiyl) | =O | | N(NH$_2$) |
| —CH$_3$ | —CH$_2$CH$_2$CH$_2$—(3-quinolyl) | =O | | N(NH$_2$) |
| —CH$_3$ | —CH$_2$CH=CH$_2$ | =O | | N(NH$_2$) |
| —CH$_3$ | —CH$_2$CH=CH—(3-quinolyl) | =O | | N(NH$_2$) |
| —CH$_3$ | —CH$_2$CH$_2$CH$_2$—(3-quinolyl) | =O | | N(NH$_2$) |

EXAMPLES

The following examples are intended to illustrate but not to limit the invention.

Compound numbers and designations are found in the Illustrative Schemes and in the prior disclosure.

In these examples, in the first general step of the method, a 6-deoxyerythronolide B (6-dEB) derivative compound is prepared by fermentation of a recombinant Streptomyces host cell.

The fermentation to produce 15-methyl-6-deoxyerythronolide B and 14,15-dehydro-6-deoxyerythronolide B requires a synthetic diketide intermediate to be fed to the fermenting cells. The preparation of these synthetic diketides is described in Example 1. These synthetic diketides are substrates for a 6-deoxyerythronolide B synthase (DEBS) that is unable to act on its natural substrate (propionyl CoA) due to a mutation in the ketosynthase domain of module 1 of DEBS. This recombinant DEBS is provided by plasmid pJRJ2 in *Streptomyces coelicolor* CH999. *S. coelicolor* CH999 is described in U.S. Pat. No. 5,672,491, incorporated herein by reference. A derivative of *S. coelicolor* CH999, *S. coelicolor* K39-02, that has been genetically modified to include a ptpA gene, is described in U.S. patent application Ser. No. 09/181,833, incorporated herein by reference can also be employed for this purpose.

Plasmid pJRJ2 encodes the eryAI, eryAII, and eryAIII genes; the eryAI gene contained in the plasmid contains the KS1 null mutation. The KS1 null mutation prevents formation of the 6-deoxyerythronolide B produced by the wild-type gene unless exogenous substrate is provided. Plasmid pJRJ2 and a process for using the plasmid to prepare novel 13-substituted erythromycins are described in PCT publication Nos. 99/03986 and 97/02358 and in U.S. patent application Ser. Nos. 08/675,817, filed Jul. 5, 1996; 08/896,323, filed Jul. 17, 1997; and 09/311,756, filed May 14, 1999, each of which is incorporated herein by reference. The exogenous substrates provided can be prepared by the methods and include the compounds described in PCT patent application No. PCT/US00/02397 and U.S. patent application Ser. No. 09/492,733, both filed Jan. 27, 2000, by inventors G. Ashley et al., and both of which claim priority to U.S. patent application Ser. No. 60/117,384, filed Jan. 27, 1999, each of which is incorporated herein by reference. PKS genes other than the ery genes can also be employed; suitable genes include the KS1 null mutation containing oleandolide and megalomicin PKS genes described in U.S. patent application Ser. Nos. 60/158,305, filed Oct. 8, 1999 and 09/428,517, filed Oct. 28, 1999, and PCT application No. US99/24478, filed Oct. 22, 1999, each of which is incorporated herein by reference.

The fermentation of *Streptomyces coelicolor* CH999/pJRJ2 and *S. coelicolor* CH999/pCK7 is described in Example 2. The isolation of the 6-deoxyerythronolide products resulting from this fermentation can be achieved by separation.

The isolated products are then added to the fermentation broth of *Saccharopolyspora erythraea* strains to make other useful intermediate compounds of the invention. The *S. erythraea* strains catalyze the biosynthesis and attachment of sugar residues to the 3 and 5 positions of the 6-dEB derivative compounds. These strains also comprise a functional eryK gene product and so hydroxylate the 6-dEB derivative compounds at the 12 position. The strains differ in regard to whether a functional eryF gene product is produced. If so, then the compounds produced are hydroxylated at the 6 position as well. If not, then a 6-deoxyerythromycin A derivative is produced. These *S. erythraea* fermentations are described in Example 3, together with the isolation of the erythromycin A derivative compounds from the fermentation broth.

Figure 7:
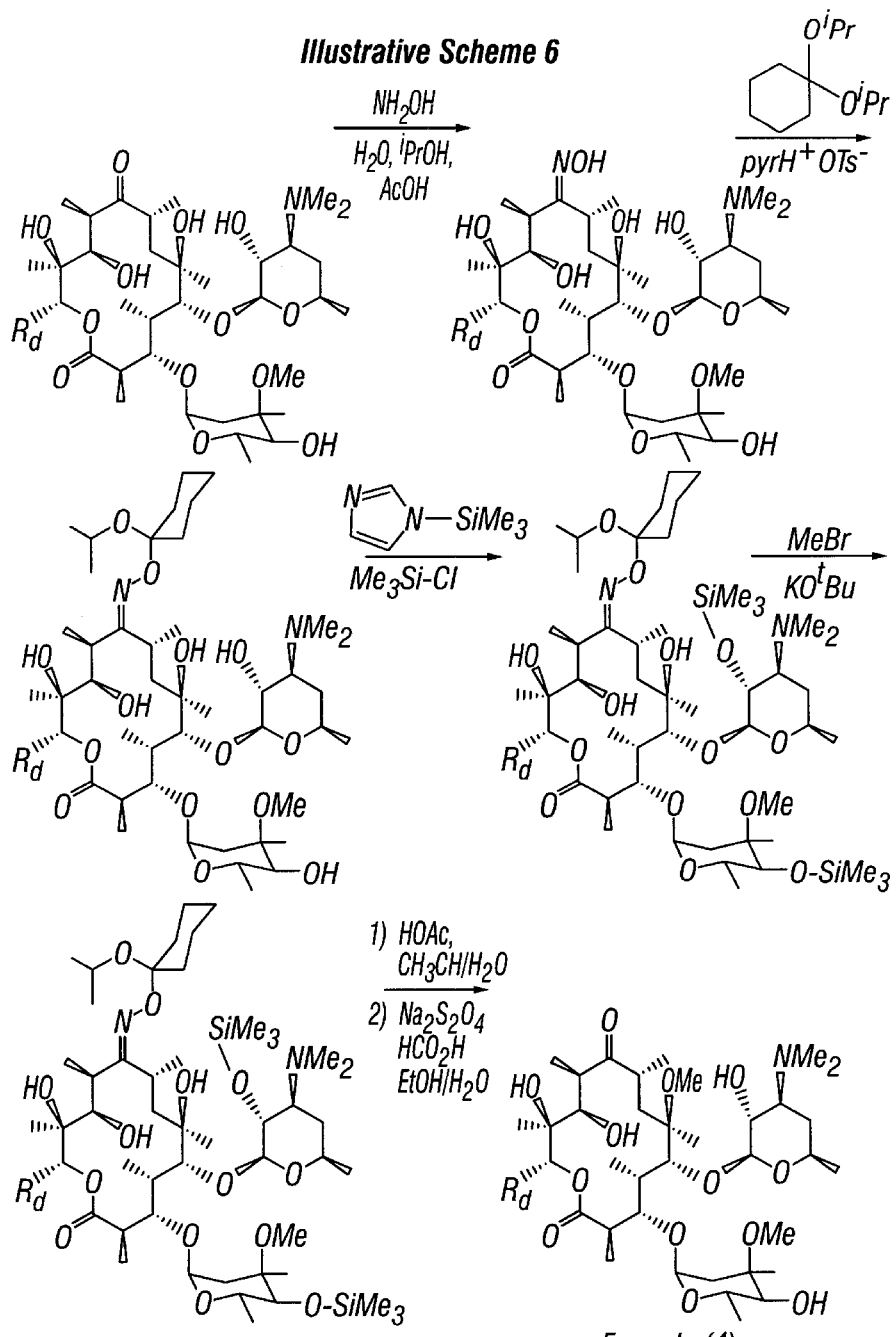
FIG. 7 shows the synthesis of intermediate compounds of formula (4) wherein $R_a$ is methyl.
Figure 8:
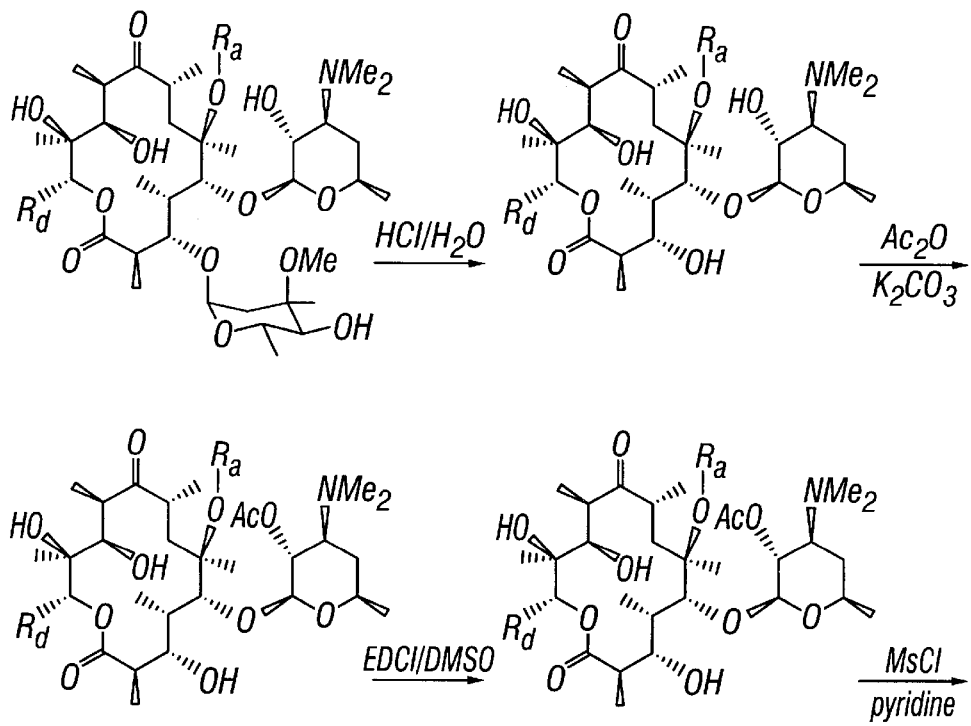
FIG. 8 shows the synthesis of intermediate compounds of formula (6) and their corresponding 10,11-anhydro forms.
Figure 8:
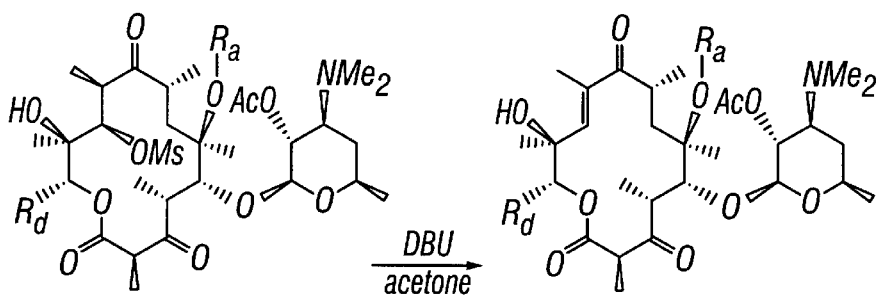
Figure 9:
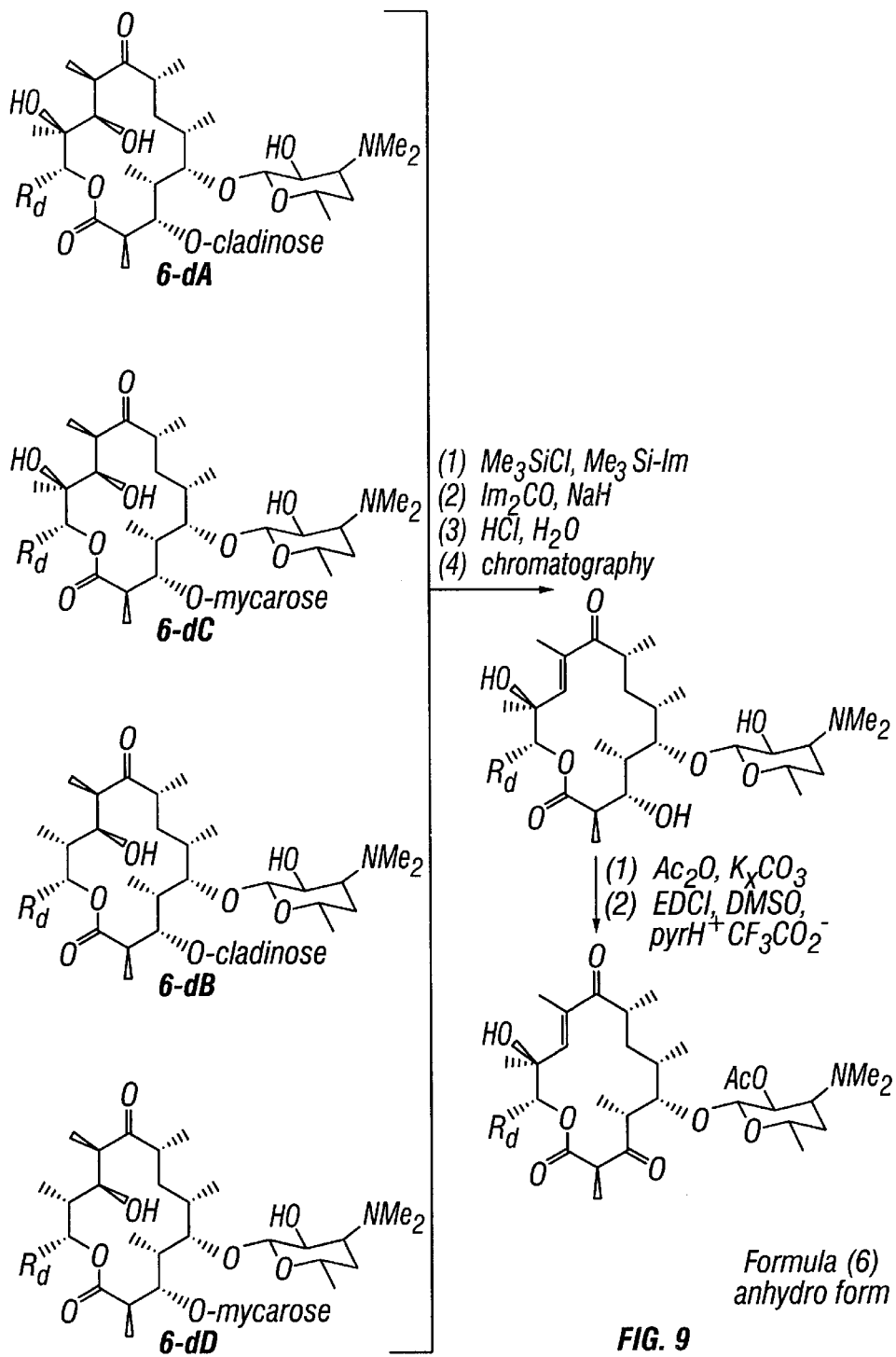
FIG. 9 shows the synthesis of intermediate compounds of formula (6) (anhydro form) wherein $OR_a$ is replaced by H.

The isolated products are then used as intermediates in the chemical synthesis of other intermediate compounds of the invention. For erythromycin A derivative intermediates that comprise a 6-hydroxyl, Examples 4–6 describe the process for alkylating the compounds to make the 6—O-alkyl intermediates of the invention. The schematic for these reactions is shown in FIG. 7.

Example 1

Preparation of Diketide Thioesters

The processes used to prepare the N-acetylcysteaminethioesters (NAcS) used to feed the recombinant Streptomyces host cells to make the 15-methyl and 14,15-dehydro-6-deoxyerythronolide B intermediate compounds are described in this Example. The synthesis protocols described below are also described in U.S. provisional patent application Serial No. 60/117,384, filed Jan. 27, 1999, incorporated herein by reference.

Thus, (2S,3R)-2-methyl-3-hydroxyhexanoate NAcS (Preparation E), which is used to prepare the 15-methyl-6-deoxyerythronolide B intermediate, is prepared from reacting (4S)-N-[(2S,3R)-2-methyl-3-hydroxyhexanoyl]-4-benzyl-2-oxazolidinone (Preparation D) with N-acetylcysteamine (Preparation B). N-acetylcysteamine is, in turn, prepared from N,S-diacetylcysteamine (Preparation A). (4S)-N-[(2S,3R)-2-methyl-3-hydroxyhexanoyl]-4-benzyl-2-oxazolidinone (Preparation D) is prepared from (4S)-N-Propionyl-4-benzyl-2-oxazolidinone (Propionyl-NOx; Preparation C).

In similar fashion, (2S,3R)-2-methyl-3-hydroxy-4-pentenoate NAcS (Preparation G), which is used to prepare the 14,15-dehydro-6-deoxyerythronolide B intermediate, is prepared from reacting (4S)-N-[(2S,3R)-2-methyl-3-hydroxy-4-pentenoyl]-4-benzyl-2-oxazolidinone (Preparation F) with N-acetylcysteamine (Preparation B). (4S)-N-[(2S,3R)-2-methyl-3-hydroxy-4-pentenoyl]-4-benzyl-2-oxazolidinone (Preparation F) is prepared from (4S)-N-Propionyl-4-benzyl-2-oxazolidinone (Propionyl-NOx; Preparation C).

A. N,S-diacetylcysteamine:

Cysteamine hydrochloride (50.0 g) is added to a 1 L 3-neck round bottom flask fitted with a magnetic stir bar, 2 addition funnels, and a pH electrode. Water (300 mL) is added, and the stirred solution is cooled on ice. The pH is adjusted to 8.0 by addition of 8 N KOH. Acetic anhydride (125 mL) is placed in one addition funnel, and 8N KOH (350 mL) is placed in the other addition funnel. The acetic anhydride is added dropwise to the cysteamine solution, with 8 N KOH being added so as to keep the reaction pH at 8+/–1. After addition of acetic anhydride is complete, the pH was adjusted to 7.0 using 1 N HCl and the mixture is allowed to stir for 75 min. on ice. Solid NaCl is added to saturation, and the solution is extracted 4 times using 400 mL portions of $CH_2Cl_2$. The organic extracts are combined, dried over $MgSO_4$, filtered, and concentrated under reduced pressure to yield 68.9 g (97% yield) of a pale yellow oil, which crystallizes upon standing at 4° C.

B. N-acetylcysteamine:

N,S-diacetylcysteamine (42.64 g) is placed in a 2 L round bottom flask fitted with a magnetic stirrer, and dissolved in 1400 mL of water. The flask is purged with $N_2$, and the mixture is chilled in an ice bath. Potassium hydroxide (49.42 g) is added, and the mixture is stirred for 2 hr. on ice under inert atmosphere. The pH is adjusted to 7 using 6 N HCl, and solid NaCl is added to saturation. The mixture is extracted 7 times with 500 mL portions of $CH_2Cl_2$. The organic extracts are combined, dried over $MgSO_4$, filtered, and concentrated under reduced pressure to yield 30.2 g (96% yield) of product. This material is distilled immediately prior to use, bp 138–140° C./7 mmHg.

C. (4S)-N-propionyl-4-benzyl-2-oxazolidinone (Propionyl-NOx):

A dry, 1 L three-necked round bottomed flask equipped with a 500 mL addition funnel and a stir bar was charged with 20 g of (4S)-4-benzyl-2-oxazolidinone, capped with septa and flushed with nitrogen. Anhydrous THF (300 mL) was added by cannula and the resulting solution was cooled with a –78° C bath of dry ice/isopropanol. The addition funnel was charged with 78 mL of n-butyllithium (1.6 M in hexane) by cannula, which was added in a slow stream to the reaction. Distilled propionyl chloride (bp 77–79° C.), 8.0 mL, was added rapidly via syringe. The reaction was allowed to stir for 30 min. in the dry ice/isopropanol bath.

The reaction was removed from the cold bath, allowed to warm to >0° C., and quenched with 50 mL of saturated aqueous $NH_4Cl$. The mixture was concentrated to a slurry on a rotary evaporator. The slurry was extracted three times with 250 mL portions of ethyl ether. The organic extracts were combined and washed with 50 mL each of saturated aqueous $NaHCO_3$ and brine, dried with $MgSO_4$, filtered, and concentrated to give a yellow oil. The material crystallized upon sitting. The crystals were triturated once with cold (−20° C.) hexanes to give 21.0 g (80% yield) of white crystalline material, m.p. 41–43° C.

APCI-MS: m/z=234 (MH+), 178, 117. 1H-NMR (360 MHz, CDCl$_3$): δ7.2–7.4 (5H,m); 4.67 (1H,m,H4); 4.14–4.22 (2H,m,H5); 3.30 (1H,dd,J=3,13 Hz,benzylic); 2.89–3.03 (2H,m,H2'); 2.77 (1H,dd,J=9,13,benzylic); 1.20 (3H,t,J=7 Hz,H2').

D. (4S)-N-[(2S,3R)-2-methyl-3-hydroxyhexanoyl]-4-benzyl-2-oxazolidinone:

A dry, 2 L three-necked round bottomed flask equipped with a 500 mL addition funnel, a low-temperature thermometer, and a stir bar was charged with 19.84 g of N-propionyl-oxazolidinone, capped with septa and flushed with nitrogen. Anhydrous dichloromethane (100 mL) was added by cannula, and the resulting solution was cooled to −65° C. in a bath of dry ice/isopropanol. The addition funnel was charged by cannula with 100 mL of dibutylboron triflate (1.0 M in dichloromethane), which was added in a slow stream to the reaction. Triethylamine (15.6 mL) was added dropwise by syringe, keeping the reaction temperature below −10° C. The reaction was then transferred to an ice bath and allowed to stir at 0° C. for 30 min. After that period, the reaction was placed back into the dry ice/isopropanol bath and allowed to cool to −65° C. Butyraldehyde (8.6 mL) was added rapidly by syringe, and the reaction was allowed to stir for 30 min.

The reaction was transferred to an ice bath and the addition funnel was charged with 100 mL of a 1 M aqueous phosphate solution, pH 7.0 (the phosphate solution is comprised of equal molar amounts of mono- and dibasic potassium phosphate). The phosphate solution was added as quickly as possible while keeping the reaction temperature below 10° C. The addition funnel was then charged with 300 mL methanol which was added as quickly as possible while keeping the reaction temperature below 10° C. Finally, the addition funnel was charged with 300 mL of 2:1 methanol:30% hydrogen peroxide. This was added dropwise to ensure that the temperature was kept below 10° C. The reaction was stirred for one hr. after completion of addition. The solvent was then removed on a rotary evaporator until a slurry remained. The slurry was extracted 4 times with 500 mL portions of ethyl ether. The combined organic extracts were washed with 250 mL each of saturated aqueous sodium bicarbonate and brine. The extract was then dried with MgSO$_4$, filtered, and concentrated to give a slightly yellow oil. The material was then chromatographed on SiO$_2$ using 2:1 hexanes:ethyl acetate (product R$_f$=0.4) resulting in 22.0 g (85% yield) of title compound as a colorless oil.

APCI-MS: m/z 306 (MH+); 1H-NMR (360 MHz, CDCl$_3$): δ7.2–7.4 (5H,m,phenyl); 4.71 (1H,m,H4); 4.17–4.25 (2H,m,H5); 3.96 (1H,m,H3'); 3.77 (1H,dq,J=2.5,7 Hz, H2'); 3.26 (1H,dd,J=4,13 Hz,benzylic); 2.79 (1H,dd,J= 9,13 Hz,benzylic); 1.5–1.6 (2H,m,H4'); 1.3–1.5 (2H,m,H5'); 1.27 (3H,d,J=7 Hz,2'-Me); 0.94 (3H,t,J=7 Hz,H6').

E. (2S,3R)-2-methyl-3-hydroxyhexanoate N-acetylcysteamine Thioester:

N-acetylcysteamine was distilled at 130° C./7 mm Hg to give a colorless liquid at room temperature. A dry, 1 L three-necked round bottomed flask equipped with a 500 mL addition funnel and a stir bar was capped with septa and flushed with nitrogen. The flask was then charged with 10.7 mL of N-acetylcysteamine by syringe and with 400 mL of 15 anhydrous THF by cannula. The mixture was cooled with a MeOH/ice bath. Butyllithium (64 mL of 1.6 M in hexanes) was added dropwise by syringe, resulting in formation of a white precipitate. After stirring for 30 min., trimethylaluminum (51 mL of 2.0 M in hexanes) was added dropwise by syringe. The reaction became clear after addition of trimethylaluminum and was allowed to stir an additional 30 min. During this period, 20.5 g (0.068 mol) of (4S)-N-[(2S,3R)-2-methyl-3-hydroxylhexanoyl]-4-benzyl-2-oxazolidinone was put under a blanket of nitrogen and dissolved in 100 mL of anhydrous THF; this solution was then transferred in a slow stream by cannula into the reaction. The resulting reaction mixture turned a yellow-green color and was allowed to stir for 1 hr. The reaction was finished when the starting material could no longer be seen by thin-layer chromatographic analysis (ca. 1 hr.).

The reaction was treated with enough saturated oxalic acid to give a neutral reaction with pH paper (approximately 90 mL). The solvents were then removed on a rotary evaporator to give a white slurry. The slurry was extracted six times with 250 mL portions of ethyl ether. The organic extracts were combined and washed with brine, dried with MgSO$_4$, filtered, and concentrated to give a slightly yellow oil. The thioester product was purified by flash chromatography on SiO$_2$ using 1:1 hexanes:EtOAc until the elution of 4-benzyl-2-oxazolidinone. At that point, the solvent system was switched to 100% EtOAc to give pure fractions of diketide thioester. The product fractions were combined and concentrated to give 14.9 g (89% yield) of title compound. This compound is referred to as the propyl diketide thioester in Example 2.

APCI-MS: m/z 248 (MH+); 1H-NMR (360 MHz, CDCl$_3$): δ5.8 (br s,1H); 3.94 (dt,1H), 3.46 (m,2H), 3.03 (dt,2H), 2.71 (dq,1H), 1.97 (s,3H), 1.50 (m,2H), 1.37 (M,2H), 1.21 (d,3H), 0.94 (t,3H).

F. (4S)-N-[(2S,3R)-2-methyl-3-hydroxy-4-pentenoyl]-4-benzyl-2-oxazolidinone:

A dry, 2 L three-necked round bottomed flask equipped with a 500 mL addition funnel, a low-temperature thermometer, and a stir bar was charged with 20.0 g of propionyl oxazolidinone A, capped with septa and flushed with nitrogen. Anhydrous dichloromethane (100 ml) was added and the resulting solution was cooled to −15° C. in a bath of methanol/ice. Dibutylboron triflate (100 mL of 1.0 M in dichloromethane) was added in a slow stream via the addition funnel at such a rate as to keep the reaction temperature below 3° C. Diisopropylethylamine (17.9 mL) was added dropwise by syringe, again keeping the internal temperature below 3° C. The reaction was then cooled to −65° C. using a dry ice/isopropanol bath. Acrolein was added over 5 min. by syringe. The reaction was allowed to stir for 30 min. after completion of addition.

The reaction was then transferred to an ice bath and the addition funnel was charged with 120 mL (0.1 mol) of a 1 M aqueous phosphate solution, pH 7.0 (the phosphate solution is comprised of equal molar amounts of mono- and dibasic phosphate). The phosphate solution was added as quickly as possible while keeping the reaction temperature below 10° C. The addition funnel was then charged with 400 mL of methanol that were added as quickly as possible while keeping the reaction temperature below 10° C. Finally, the addition funnel was charged with 400 mL of 2:1 methanol:30% hydrogen peroxide by initial dropwise addition to keep the temperature below 10° C. The reaction was stirred for one hour. The solvent was removed using a rotary evaporator, leaving a slurry. The slurry was extracted 4 times with 500 mL portions of ethyl ether. The organic extracts were combined and washed with 250 mL each of saturated sodium bicarbonate and brine, then dried with MgSO$_4$, filtered, and concentrated to give a slightly yellow oil. Trituration with hexane induced crystallization. Recrystallization from ether by addition of hexane resulted in 13.67 g (55% yield) of product.

1H-NMR (360 MHz, CDCl$_3$): δ7.2–7.4 (m,5H); 5.86 (ddd,1H), 5.35 (dt,1H), 5.22 (dt,1H), 4.71 (m,1H), 4.51 (m,1H), 4.21 (m,2H), 3.89 (dq,1H), 3.26 (dd,1H), 2.80 (dd,1H), 1.25 (d,3H).

G. (2S,3R)-2-methyl-3-hydroxy-4-pentenoate N-acetylcysteamine Thioester:

N-acetylcysteamine was distilled at 130° C./7 mm Hg to give a colorless liquid at room temperature. A dry, 1 L three-necked round bottomed flask equipped with a 500 mL addition funnel and a stir bar was capped with septa and flushed with nitrogen. The flask was then charged with 7.5 mL of N-acetylcysteamine by syringe and with 500 mL of anhydrous THF by cannula. The reaction was then cooled with a MeOH/ice bath. Butyllithium (44 mL of 1.6 M in hexane) was added dropwise by syringe. A white precipitate formed as the n-BuLi was added. After stirring for 30 min., 35.5 mL (0.071 mol) of trimethylaluminum (2.0 M in hexane) were added drop-wise by syringe. The reaction became clear after addition of trimethylaluminum and was allowed to stir an additional 30 min. (4S)-N-[(2S,3R)-2-methyl-3-hydroxy-4-pentenoyl]-4-benzyl-2-oxazolidinone from Preparation F (13.6 g) was put under a blanket of nitrogen, dissolved in 50 mL of anhydrous THF, and this solution was then transferred in a slow stream by cannula into the reaction. The resulting reaction mixture turned a yellow-green color and was allowed to stir for 1 hr. The reaction was judged to be finished when starting material could no longer be seen by thin-layer chromatography (ca. 30 min.).

Enough saturated oxalic acid was added to give a neutral reaction with pH paper (approximately 60 mL). The solvents were then removed by rotary evaporator to give a white slurry. The slurry was extracted six times with 250 mL portions of ethyl ether. The organic extracts were combined, washed with brine, dried with MgSO$_4$, filtered, and concentrated to give a slightly yellow oil. The thioester was then purified by flash chromatography on SiO$_2$. The column was run with 1:1 hexanes:ethyl acetate until the elution of oxazolidinone. At that point, the eluent was switched to 100% ethyl acetate to give pure fractions of product. The fractions were combined and concentrated to give 7.7 g (71% yield) of title compound product. This product is referred to as the vinyl diketide thioester in Example 2.

1H-NMR (360 MHz, CDCl$_3$): δ5.82 (ddd,1H), 5.78 (br s, 1H), 5.32 (dt,1H), 5.21 (dt,1H), 4.47 (m,1H), 3.45 (m,2H), 3.04 (m,2H), 2.81 (dq,1H), 1.96 (s,3H), 1.22 (d,3H).

Example 2

Preparation of Erythronolide

A. 15-methyl-6-deoxyerythronolide B (Compound P, R$_d$=propyl):

*Streptomyces coelicolor* CH999/pJRJ2 is described in U.S. patent application Ser. Nos. 08/896,323, filed Jul. 17, 1997, and 08/675,817, filed Jul. 5, 1996, each of which is incorporated herein by reference. Plasmid pJRJ2 encodes a mutated form of DEBS in which the ketosynthase domain of module 1 (KS1) has been inactivated via mutagenesis (KS1°). *S. coelicolor* strains comprising this plasmid that are fed (2S, 3R)-2-methyl-3-hydroxyhexanoate-N-acetylcysteamine Preparation E, propyl diketide) of Example 1 produce 15-methyl-6-deoxyerythronolide B.

A 1 mL vial of the CH999/pJRJ2 working cell bank is thawed and the contents of the vial are added to 50 mL of Inoculum Medium 1 in a 250 mL baffled flask. The flask is placed in an incubator/shaker maintained at 30±1° C. and 175±25 RPM for 48±10 hours. The 50 mL culture is then added to a 2.8 L baffled flask containing 500 mL of Inoculum Medium 1. This flask is incubated in an incubator/shaker at 30±1° C. and 175±25 RPM for 48±10 hours. The 500 mL culture is divided equally among ten 2.8 L baffled flasks each containing 500 mL of Inoculum Medium 1. All flasks are then incubated as described previously.

A 150 L fermenter is prepared by sterilizing 100 L of Production Medium 1 at 121° C. for 45 minutes. After incubation, all 10 flasks are combined in a 5 L sterile inoculation bottle and aseptically added to a 150 L fermenter. The fermenter is controlled at 30° C., pH 6.5 by addition of 2.5 N H$_2$SO$_4$ and 2.5 N NaOH, dissolved oxygen ≧80% air saturation by agitation rate (500–700 RPM), air flow rate (10–50 LPM), and/or back pressure control (0.1–0.4 bar). Foam is controlled by the intermittent addition of a 50% solution of Antifoam B.

At 24±5 hours (2S, 3R)-2-methyl-3-hydroxyhexanoyl-N-acetylcysteamine (propyl diketide, Preparation E in Example 1) is added to a final concentration of 1 g/L. Propyl diketide is prepared by solubo017ing in dimethyl sulfoxide at a ratio of 1:4 (diketide to DMSO) and then filter sterilized (0.2 μm, nylon filter). Production of 15-methyl-6-deoxyerythonolide B (15-methyl-6dEB) ceases on day 7 and the fermenter is harvested. The fermentation broth is centrifuged at 20,500 g in an Alpha Laval AS-26 centrifuge. The product is predominantly in the centrate; the centrifuged cell mass is discarded.

This process has also been completed in a 1000 L fermenter (700 L working volume). The inoculum process is identical to the above process except that the 150 L fermenter is charged with Inoculum Medium 1 and the 1000 L fermenter is charged with Production Medium 1. The fermenter is controlled at 30° C., pH 6.5 by addition of 2.5–5 N H$_2$SO$_4$ and 2.5–5 N NaOH, dissolved oxygen ≧70% air saturation by agitation rate (140–205 RPM), air flow rate (100–200 LPM), and/or back pressure control (0.2–0.5 bar). Foam is controlled by the addition of a 50% solution of Antifoam B as needed. At 24±5 hours racemic 2-methyl-3-hydroxyhexanoyl-N-propionylcysteamine (300 grams) is added to the 1000 L fermenter. The fermenter is harvested at 4.6 days by centrifugation as described above.

Media used in this process include the following:

Inoculum Medium 1

| Component | Concentration |
| --- | --- |
| KNO$_3$ | 2 g/L |
| Yeast extract | 20 g/L |
| Hycase SF | 20 g/L |
| FeSO$_4$—7H$_2$O | 25 mg/L |
| NaCl$_4$ (12.5% stock) | 4 mL/L |
| MgSO$_4$ (12.5% stock) | 4 mL/L |
| MnSO$_4$—H$_2$O (0.5% stock) | 1 mL/L |
| ZnSO$_4$—7H$_2$O (1.0% stock) | 1 mL/L |
| CaCl$_2$—2H$_2$O 2.0% stock | 1 mL/L |

Sterilized by autoclaving for 60 minutes at 121° C.

Post-sterile additions:

1) 1 mL/L of 50 mg/ml Thiostrepton in 100% DMSO, sterile filtered.

2) 1 mL/L 100% Antifoam B silicon emulsion (J. T. Baker), autoclaved.

3) 40 mL of 500 g/L glucose, sterile filtered.

Production Medium 1

| Component | g/L |
| --- | --- |
| Corn Starch | 45 |
| Corn steep liquor | 10 |
| Dried, inactivated brewers yeast | 10 |
| CaCO$_3$ | 1 |

Sterilized in fermenter for 45 minutes at 121° C.
Post-sterile additions for Production Medium 1:
1) 1 mL of 50 mg/ml Thiostrepton in 100% DMSO, sterile filtered.
2) 1 mL/L of 100% Antifoam B (J. T. Baker), autoclaved.

After centrifugation, the centrate is filtered. The filtrate (approximately 700 L) are passed through an Amicon Moduline column (20×350 cm) containing 20 L of HP20 resin (Mitsubishi). The flow rate during loading is 4 L/minute with a pressure drop below 8 psi. After loading the resin is washed with 20 L of water and then 40 L of 30% methanol. 15-methyl-6dEB is eluted using 100% methanol. Four 12 L fractions were collected with fractions 2, 3 and 4 containing all of the detectable 15-methyl-6dEB. The 15-methyl-6dEB product pool is diluted with 36.7 L of water giving 75 L of a clear solution. This solution is loaded directly onto a 5 L Amicon Vantage Column containing HP20SS resin (Mitsubishi). Column loading is carried out at 1 L/minute. The column is eluted with 20 L of 65% methanol, 20 L of 70% methanol, 20 L of 80% methanol, and finally 20 L of 100% methanol. A total of 16×5 L fractions were collected. The 80% fractions along with the last 70% fraction were combined (25 L) and evaporated to dryness. The resulting residue is dissolved in 1 L of 100% methanol, filtered, evaporated, and dried in a vacuum oven at 40° C. This process resulted in 33 g of a solid product containing 93% 15-methyl-6dEB.

B. 14,15-dehydro-6-deoxyerythronolide B (Compound P, R$_d$=vinyl):

S. *coelicolor* strains comprising this plasmid that are fed (2S,3R)-2-methyl-3-hydroxy-4-pentenoate NAc Cysteamine thioester (Preparation G) of Example 1 produce 14,15-dehydro-6-deoxyerythronolide B when prepared in accordance with the process described in Preparation A above to produce 15-methyl-6-deoxyerythronolide B.

C. 14-nor-6-deoxyerythronolide B (Compound P, R$_d$=methyl):

Similarly, 14-nor-6-deoxyerythronolide B is produced using S. *coelicolor* CH999/pCK7 host, when prepared in accordance with the process described in Example 2A Example 3

Preparation of Erythromycins

The 6-dEB derivative compounds produced in Example 2, Preparations A—C are converted to erythromycin derivatives using a recombinant strain of *Saccharopolyspora erythraea*. For production of erythromycins having both the 6- and 12-hydroxyl groups, the *S. erythraes* strain used was K40-67 or K39-14V. This strain was created by transforming an *S. erythrae* strain capable of producing high levels of erythromycin A with a pWHM3-derived plasmid comprising a mutated eryAl sequence encoding an inactivated KS1 domain. By homologous recombination, the resulting transformants were rendered incapable of producing 6-deoxyerythronolide B. Thus the dEB analog fed is not subject to competition for hydroxylation at the 6-position.

For production of erythromycin derivatives having only the 12-hydroxyl group, the *S. erythrae* strain used was K39-07. This strain was constructed from strain K40-67 by disruption of the eryF hydroxylase gene; this destroys ability to hydroxylate the analog at the 6-position. Both strains were fermented under substantially similar conditions, as described below.

15-methyl-erythromycin A: 15-methyl-erythromycin A is produced according to the following protocol: A 1 mL vial of the K39-14V working cell bank is thawed and the contents of the vial are added to 50 mL of Inoculum Medium 2 in a 250 mL baffled flask. The flask is placed in an incubator/shaker maintained at 34±1° C. and 175±25 RPM for 48±10 hours. The 50 mL culture is then added to a 2.8 L baffled flask containing 500 mL of Inoculum Medium 2. The flask is incubated in an incubator/shaker at 34±1° C. and 175±25 RPM for 48±10 hours. The 500 mL culture is divided equally among ten 2.8 L baffled flasks each containing 500 mL of Inoculum Medium 2. All flasks are then incubated as described previously.

A 150 L fermenter is prepared by sterilizing 100 L of Production Medium 2 at 121° C. for 45 minutes. After incubation, all 10 flasks are combined in a 5 L sterile inoculation bottle and aseptically added to a 150 L fermenter. The fermenter is controlled at 34° C., pH 7.0 by addition of 2.5 N H$_2$SO$_4$ and 2.5 N NaOH, dissolved oxygen ≧80% air saturation by agitation rate (500–700 RPM), air flow rate (15–50 LPM), and/or back pressure control (0.1–0.4 bar). Foam is controlled by the addition of a 50% solution of Antifoam B.

At 24±5 hours a 58–60 mL/hour 15% dextrin (w/v) feed is initiated. The dextrin solution is continuously mixed during the feed period. At 24±5 hours 25 grams of 15-methyl-6dEB (Preparation A in Example 2) are added to the fermenter. The 15-methyl-6dEB is prepared by solubilizing 25 grams of 15-methyl-6dEB in 400–600 mL of 100% ethanol and filtering (0.2 µm, nylon filter). Conversion of 15-methyl-6dEB to 15-methyl-erythromycin A ceases after 60±10 hours and the fermenter is harvested. The fermentation broth is centrifuged at 20,500 g in an Alpha Laval AS-26 centrifuge. The product is predominantly in the centrate; the centrifuged cell mass is discarded.

Media used in this process include the following:

Inoculum Medium 2

| Component | g/L |
| --- | --- |
| Corn Starch | 16.0 |
| Corn dextrin | 10.0 |
| Soy Meal Flour | 15.0 |
| CaCO$_3$ | 4.0 |
| Corn steep liquor | 5.0 |
| Soy Bean Oil | 6.0 |
| NaCl | 2.5 |
| (NH$_4$)$_2$SO$_4$ | 1.0 |

Sterilized by autoclaving for 60 minutes at 121° C.
Post-sterile addition:
1 mL/L 100% Antifoam B (J. T. Baker), autoclaved.
Production Medium 2

| Component | g/L |
|---|---|
| Corn Starch | 17.5 |
| Corn Dextrin (Type 3) | 16.0 |
| Soy Meal Flour | 16.5 |
| $CaCO_3$ | 4.0 |
| Corn steep liquor | 6.0 |
| Soy Bean Oil | 3.0 |
| NaCl | 3.5 |
| $(NH_4)_2SO_4$ | 1.0 |

Sterilized in fermenter for 45 minutes at 121° C.

Centrifuged fermentation broth (127 L) containing 34 g of the target molecule is passed through 18.3 L of HP20 sorbent packed into an Amicon P350 Moduline 2 chromatography column. At 4 L/min loading, backpressure is found to be less than 5 psi. Following loading, the resin is washed with 20 L deionized water and then 40 L of 30% methanol. 15-Methyl-Erythromycin A is eluted using 54 L of 100% methanol. The product pool is evaporated using a Buchi rotary evaporator (R-152). The solids were dissolved in a minimal amount of 100% methanol, filtered and the filtrate evaporated to dryness. This resulted in 123 g of material containing 30% 15-Methyl-Erythromycin A by weight. 80 grams of the 30% material is extracted twice with 1 L of 40° C. acetone. The acetone extract is filtered, and the filtrate is dried on the inside surface of a 20 L rotary evaporation flask. The solids were extracted with 9:1 hexane to acetone three times at 40° C. The organic extracts were pooled and evaporated to dryness giving 32 g of solids enriched (68%) in 15-Methyl-Erythromycin A. The product pool from the acetone/hexane extraction is dissolved in 1 L of methanol to which an equal amount of water is added. The methanol solution is loaded onto a HP20SS chromatography column (Kontes) previously washed and equilibrated with 50% methanol. Column dimensions were 4.8×115 cm. Column loading with respect to 15-Methyl-Erythromycin A is 11 g/L. The column is washed with 50% (0.8 L) and 60% (8 L) methanol in water. Elution of the target molecule is carried out using 70% (8L), 80% (16 L) and 85% (8 L) methanol in water. 1 L fractions were collected. Fractions 11–29 were combined, evaporated and dried in a vacuum oven giving 23 g of product with 93% purity.

This material served as starting material for the chemical derivatization procedures described in the following examples. The following compounds are also produced by this methodology: (i) 14-norerythromycin A ($R_d$=Me); (ii) 14,15-dehydro-erythromycin A ($R_d$=—CH=CH$_2$); (iii) 14-nor-6-deoxy-etythromycin A; (iv) 14,15-dehydro-6-deoxy-erythromycin A; and (v) 15-methyl-6-deoxy-erythromycin A. When used to make 3-descladinose-3-oxo-derivatives, the erythromycin A derivatives were not separated from the erythromycin C derivatives; instead, mixtures of the erythromycin A and erythromycin C compounds were used as starting materials for chemical derivatization.

These products were extracted and purified as follows:

In general, fermentation broths are brought to pH 8.0 by addition of NaOH and ethanol is added (0.1 L/L broth). The broth is clarified by centrifugation and loaded onto an XAD-16 resin (Rohm and Haas) column (1 kg XAD/1 g erythromycin analogs) at a flow rate of 2–4 mL/cm$^2$·min. The loaded resin is washed with 2 column volumes of 20% (v/v) ethanol in water and the erythromycin analogs are eluted from the resin with acetone and collected in ½ column volume fractions. The fractions containing erythromycin analogs are identified by thin-layer chromatography (ethyl acetate:hexanes 1:1) and HPLC/NS.

The acetone fractions containing erythromycin analogs are pooled and the volatiles are removed under reduced pressure. The resulting aqueous mixture is extracted with ethyl acetate. The ethyl acetate extract is washed with saturated $NaH_2CO_3$ and brine solutions, dried over sodium or magnesium sulfate, filtered, and concentrated to dryness under reduced pressure. Crude material is dissolved in dichloromethane and loaded onto a pad of silica gel and washed with dichloromethane:methanol (96:4 v/v) until the eluent is no longer yellow. The desired material is with dichloromethane:methanol:triethylamine (94:4:2 v/v) and collected in fractions. Fractions containing erythromycin are identified by thin-layer chromatography, collected and concentrated under reduced pressure. This material is recrystallized from dichloromethane/hexanes.

This general procedure is illustrated as follows:

(i) 14-norerythromycins: 1 liter of ethanol was added to each of 10 liters of fermention broth. The broth was centrifuged and the supernatant was passed through 0.6 liters of XAD (column dimensions 17 cm×6.5) cm at a flow rate of 100 mL/min. After loading, the column was washed with 1.5 liters of 20% (v/v) ethanol in water. The desired material was then eluted with acetone. The fractions containing this material were concentrated under reduced pressure until the volatiles were removed and the aqueous remainder was extracted with ethyl acetate. The ethyl acetate layers were washed with saturated sodium bicarbonate solution, brine, dried with magnesium sulfate and concentrated under reduced pressure to give the crude extract.

Crude material (0.6 g) was dissolved in dichloromethane and gravity filtered through a 3 cm pad of silica gel in a 6 cm diameter flitted funnel. The material was eluted with 400 mL of dichloromethane followed by 400 mL dichloromethane:methanol:triethylamine (90:10:2 v/v) and collected in 40 mL fractions.

Fractions containing erythromycin were identified by thin-layer chromatography (ether:methanol:$NH_4OH$ 90:8:2 v/v, $R_f$~0.35 and dichloromethane:methanol 95:5 v/v, $R_f$~0) and concentrated under reduced pressure. This material was recrystallized from dichloromethane/hexanes.

(ii) 15-methyl-erythromycin A: 8 liters of ethanol was added to approximately 80 liters of fermentation broth. The broth was centrifuged and the supernatant was passed through 2.5 liters of XAD at a flow rate of 230 mL/min. After loading the column was washed with 1 liter of water and 5 liters of 20% (v/v) ethanol in water. The desired material was then eluted with acetone. The fractions containing this material were concentrated under reduced pressure until the volatiles were removed and the aqueous remainder was extracted with ethyl acetate. The ethyl acetate layers were washed with saturated sodium bicarbonate solution, brine, dried with magnesium sulfate and concentrated under reduced pressure to give the crude extract Crude material (8.3 g) was dissolved in dichloromethane and gravity filtered through a 3 cm pad of silica gel in a 9 cm diameter fritted funnel. The material was eluted with 200 mL of dichloromethane followed by 600 mL of dichloromethane:methanol (96:4 v/v) followed by 900 mL dichloromethane:methanol:triethylamine (89:9:2 v/v) and collected in 40 mL fractions. Fractions containing erythromycin were identified by thin-layer chromatography (ether:methanol:NH$_4$OH 90:8:2 v/v, R$_f$~0.4 and dichloromethane:methanol 95:5, R$_f$~0.05) and concentrated under reduced pressure.

This material was re-subjected to the above procedure before it was suitable for recrystallization.

(iii) 14-nor-6-deoxy-erythromycins: 1 liter of ethanol was added to each of 210 liter fermentions. The broths were centrifuged and the supernatants were combined for a total of approximately 22 liters. The combined broths were then passed through 1 liter of XAD (column dimensions 23.5 cm×6.5 cm (i.d.) at a flow rate of 170 mL/min. After loading the column was washed with 2 liters of 20% (v/v) ethanol in water. The desired material was then eluted with acetone. The fractions containing this material were concentrated under reduced pressure until the volitiles were removed and the aqueous remainder was extracted with ethyl acetate. The ethyl acetate layers were washed with saturated sodium bicarbonate solution, brine, dried with magnesium sulfate and concentrated under reduced pressure to give the crude extract.

(iv) 15-methyl-6-deoxy-erythromycins: 1 liter of ethanol was added to each of 3 fermentors containing 10 liters of broth. The broths were centrifuged and the supernatant was passed over 1.25 liters of XAD (column dimensions 40 cm×6.5 cm) at a flow rate of 130 mL/min. The column was then washed with 3 liters of 20% (v/v) ethanol in water. The desired material was then eluted with acetone. The fractions containing this material were concentrated under reduced pressure until the volitiles were removed and the aqueous remainder was extracted with ethyl acetate. The ethyl acetate layers were washed with saturated sodium bicarbonate solution, brine, dried with magnesium sulfate and concentrated under reduced pressure to give the crude extract.

Crude material (2.8 g) was dissolved in dichloromethane and gravity filtered through a 3 cm pad of silica gel in a 6 cm diameter fritted funnel. The material was eluted with 400 mL of dichloromethane:methanol (96:4 v/v) followed by 400 mL dichloromethane:methanol:triethylamine (89:9:2 v/v) and collected in 40 mL fractions. Fractions containing erythromycin were identified by thin-layer chromatography (ether:methanol:NH$_4$OH 90:8:2 v/v and dichloromethane:methanol 95:5) and concentrated under reduced pressure. This material required further purification by silica gel chromatography.

Example 4

Synthesis of 6-O-methyl-14-norerythromycin A i.e., Formula (4) where R$_d$=Me, R$_d$=Me, R$_c$=H, R$_e$=H A. 14-Norerythromycin A 9-Oxime:

A solution of 14-norerythromycin A (0.621 g, 80% pure), hydroxylamine (0.5 ml of 50% aqueous solution) and acetic acid (0.2 ml) in isopropanol (2 ml) was kept at 50° C. for 22 hours. It was extracted with chloroform/ethanol (3/2), washed with sodium bicarbonate, brine, and dried over MgSO$_4$. Filtration and evaporation in vacuo yielded a crude product (0.65 g) as a white solid which was used directly for next transformation.

B. 14-Norerythromycin A-9-[O-(1-isopropoxycyclohexyl)] oxime:

To a solution of above crude 14-norerythromycin A 9-oxime (0.65 g) and 1,1-diisopropoxy-cyclohexanone (0.95 ml) in methylene chloride (2 ml) was added pyridinium p-toluenesulfonate (PPTS) (0.333 g) in methylene chloride (2 ml). After stirring overnight, the mixture was extracted (chloroform/ethanol 3:2), washed (NaHCO$_3$—H$_2$O, brine), and dried (MgSO$_4$). After filtration and evaporation in vacuo, the crude product was repeatedly driven with toluene and isopropanol to yield 0.74 g of product, which was used directly for next reaction.

C. 2',4"-bis-O-trimethylsilyl-14-norerythromycin A-9-[O-(1-isopropoxycyclohexyl)]oxime:

To a solution of 14-norerythromycin A-9-[O-(1-isopropoxycyclohexyl)]oxime (0.74 g) in methylene chloride (6 ml) was added a solution of trimethylsilyl imidazole (0.33 ml) and trimethylsilyl chloride (0.18 ml) in methylene chloride (2 ml) at 0° C. After 5 minute stirring, ethyl acetate was added, washed (NaHCO$_3$—H$_2$O, brine), and dried (MgSO$_4$). Flash chromatography on silica gel (10:1 hexanes:acetone, 1% triethylamine) afforded pure product as a white solid (0.50 g). Mass spectrometry reveals [M+H]$^+$=1020.

D. 6-O-Methyl-2',4"-bis-O-trimethylsilyl-14-norerythromycin A-9-[O-(1-isopropoxycyclohexyl)]oxime:

A solution of 2',4"-bis-O-trimethylsilyl-14-norerythromycin A 9-[O-(1-isopropoxycyclohexyl)]oxime (0.3 g, 0.29 mmol) in 1:1 methylsuylfoxide/tetrahydrofuran (DMSO/THF) (1.4 ml) was treated with 0.3 ml of a 2 M solution of methyl bromide in ether and cooled to 10° C. A mixture of 1 M solution of potassium tert-butoxide in THF (0.6 ml) and DMSO (0.6 ml) was added over 6 hours using a syringe pump. The reaction was then diluted with ethyl acetate, washed with saturated NaHCO$_3$, brine, and dried over MgSO$_4$. Filtration and evaporation in vacuo yielded a crude product (0.29 g) as a white solid. Mass spectrometry reveals [M+H]$^+$=1034.

E. 6-O-Methyl-14-norerythromycin A 9-oxime:

A mixture of 6-O-methyl-2',4"-bis-O-trimethylsilyl-14-norerythromycin A 9-[O-(1-isopropoxycyclohexyl)]oxime (0.29 g), acetic acid (3.6 ml), acetonitrile (6 ml) and water (3 ml) was stirred at ambient temperature for 4.5 hours. The mixture was driven to dryness using toluene to give a crude product as white solid (0.24 g), which was used directly for next step without further purification.

F. 6-O-Methyl-14-norerythromycin A:

A mixture of 6-O-methyl-14-norerythromycin A 9-oxime (0.24 g), sodium hydrosulfite (0.45 g, 85% pure), water (3 ml), ethanol (3 ml) and formic acid (0.07 ml) was kept at 85° C. for 8 hours. The reaction was brought to pH 8 with 1 N NaOH and extracted with ethyl acetate. The organic extract was washed with brine, dried over MgSO$_4$, filtered, and concentrated to yield a crude product as a white solid (0.2 g). Mass spectrometry reveals [M+H]$^+$=735.

Example 5

Synthesis of 6-O-methyl-14,15-dehydroerythromycin A, i.e. Formula (4) where R$_d$=CH=CH$_2$, R$_a$=Me, R$_c$=H, R$_e$=H A. 14,15-dehydroerythromycin A 9-oxime A suspension of 14,15-dehydroerythromycin A (1.984 g, 47% purity, 1.2 mmol) in 6 mL of 2-propanol was treated with 1.97 mL of 50% aqueous hydroxylamine and stirred until dissolved. Acetic acid (0.62 mL) was added and the mixture was stirred for 25 hours at 50° C. Upon cooling to ambient temperature, saturated NaHCO$_3$ was added and the mixture was concentrated en vacuo to remove isopropanol. The resulting aqueous mixture was extracted three times with 250-mL portions of CHCl$_3$. The organic extracts were combined, washed with saturated NaHCO$_3$, water, and brine, then dried over MgSO$_4$, filtered, and concentrated to yield 0.92 g of product.

B. 14.15-dehydroerythromycin A 9-[O-(1-isopropoxycyclohexyl)oxime

The oxime from (A) (0.92 g) was dissolved in 6.2 mL of CH$_2$Cl$_2$ and treated with 1,1-diisopropoxycyclohexane (1.23 g) and pyridinium p-toluenesulfonate (0.464 gm) for 15 hours at ambient temperature. The mixture was diluted with 160 ML of $CH_2Cl_2$, then washed sequentially with saturated $NaHCO_3$, water, and brine. The organic phase was dried with $MgSO_4$, filtered, and evaporated to yield a brown syrup. Chromatography on silica gel (gradient from toluene to 1:1 toluene/acetone+1% $Et_3N$) yielded 0.998 g of product.

C. 2',4"-bis(O-trimethylsilyl)-14,15-dehydroerythromycin A 9-[O-(1-isopropoxycyclohexyl)]oxime A solution of 14,15-dehydroerythromycin A 9-[O-(1-isopropoxycyclohexyl)]oxime (998 mg, 9.96) in 11.25 mL of $CH_2Cl_2$ was cooled on ice under inert atmosphere and treated with a solution of chlorotrimethylsilane (0.24 mL) and 1-trimethylsilylimidazole (0.44 mL). After 30 minutes, the reaction was diluted with 250 mL of ethyl acetate and washed sequentially with saturated $NaHCO_3$, water, and brine. The organic phase was dried with $MgSO_4$, filtered, and evaporated to yield 1.002 g of product.

D. 2',4"-bis(O-trimethylsilyl)-6-O-methyl-14,15-dehydroerythromycin A 9-[O-(1-isopropoxycyclohexyl)]oxime A solution of 2',4"-bis-O-trimethylsilyl-14,15-dehydroerythromycin A 9-[O-(1-isopropoxycyclohexyl)]oxime (1.00 g, 20.7 mmol) in 9.69 mL of 1:1 tetrahydrofuran/methylsulfoxide was cooled to 10° C. and treated with 0.97 mL of 2.0 M methyl bromide in ether under inert atmosphere. A mixture of methylsulfoxide (1.94 mL) and 1.0 M potassium tert-butoxide in tetrahydrofuran (1.94 mL) was added slowly. The reaction was monitored by thin-layer chromatography (silica gel, 10:1 toluene/acetone), and was judged complete after addition of 1.6 molar equivalents of base. The reaction was diluted with 200 mL of ethyl acetate and 70 mL of saturated $NaHCO_3$. The mixture was transferred to a separatory funnel, diluted with 850 mL of ethyl acetate and 280 mL of saturated $NaHCO_3$, then washed sequentially with water and brine. The organic phase was dried with $MgSO_4$, filtered through Celite, and evaporated to yield 21.2 g of crude 6-O-methyl-2',4"-bis-O-trimethylsilyl-14,15-dehydroerythromycin A 9-[O-(1-isopropoxycyclohexyl)]oxime. This was carried on without further purification.

E. 6-O-methyl-14,15-dehydroerythromycin A 9-oxime

A solution of 6-O-methyl-2',4"-bis-O-trimethylsilyl-14,15-dehydroerythromycin A 9-[O-(1-isopropoxycyclohexyl)]oxime (1.0 g) in 9.8 mL of 2:1 acetonitrile/water was treated with 5.3 mL of acetic acid, and stirred for 8 hours at ambient temperature. The mixture was concentrated en vacuo, then repeatedly concentrated after addition of toluene to yield 0.797 g of crude 6-O-methyl-14,15-dehydroerythromycin A 9-oxime.

F. 6-O-methyl-14,15-dehydroerythromycin A

A solution of 6-O-methyl-14,15-dehydroerythromycin A 9-oxime (0.797 g) and sodium hydrosulfite (85%, 1.02 g) in 7.5 mL of 1:1 ethanol/water was placed under inert atmosphere. Formic acid (0.186 mL) was added dropwise, and the mixture was stirred at 80° C. for 3 hours. After cooling to ambient temperature, the reaction was adjusted to pH 10 with 6 N NaOH and extracted three times with 150-mL portions of ethyl acetate. The organic extracts were combined and washed sequentially with saturated $NaHCO_3$, water, and brine. The organic phase was dried with $MgSO_4$, filtered, and evaporated to yield 0.68 g of 6-O-methyl-14,15-dehydroerythromycin A suitable for further conversion.

Example 6

Synthesis of 6-O-methyl-15-methylerythromycin A, i.e. Formula (4) where $R_d$=propyl, $R_a$=Me, $R_c$=H, $R_e$=H A. 15-Methylerythromycin A 9-Oxime:

A suspension of 15-methylerythromycin A (20.0 g, 85% purity, 22.6 mmol) in 40 mL of 2-propanol was treated with 20.5 mL of 50% aqueous hydroxylamine and stirred until dissolved. Acetic acid (6.41 mL) was added and the mixture was stirred for 15 hours at 50° C. Upon cooling to ambient temperature, saturated $NaHCO_3$ was added and the mixture was concentrated en vacuo to remove isopropanol. The resulting aqueous mixture was extracted three times with 250-mL portions of $CHCl_3$. The organic extracts were combined, washed with saturated $NaHCO_3$, water, and brine, then dried over $MgSO_4$, filtered, and concentrated to yield 20.5 g of crude product. Analysis by LC/MS revealed a 94:6 mixture of E and Z oximes, $[M+H]^+$=764.

B. 15-Methylerythromycin A 9-[O-(1-isopropoxcyyclohexyl)]oxime:

The crude oxime from above (20.5 g) was dissolved in 55 mL of $CH_2Cl_2$ and treated with 1,1-diisopropoxycyclohexane (27.3 mL) and pyridinium p-toluenesulfonate (9.8 gm) for 15 hours at ambient temperature. The mixture was diluted with 160 mL of $CH_2Cl_2$, then washed sequentially with saturated $NaHCO_3$, water, and brine. The organic phase was dried with $MgSO_4$, filtered, and evaporated to yield a brown syrup. Chromatography on silica gel (gradient from 2:1 to 3:2 hexanes/acetone +1% $Et_3N$) yielded 18.0 g of product.

C. 2',4"-bis-O-trimethylsilyl-15-methylerythromycin A 9-[O-(1-isopropoxycyclohexyl)]oxime:

A solution of 15-Methylerythromycin A 9-[O-(1-isopropoxycyclohexyl)]oxime (9.00 g, 9.96 mmol) in 25 mL of $CH_2Cl_2$ was cooled on ice under inert atmosphere and treated with a solution of chlorotrimethylsilane (1.89 mL) and 1-trimethylsilylimidazole (3.65 mL) in 8 mL of $CH_2Cl_2$. After 30 minutes, the reaction was diluted with 250 mL of ethyl acetate and washed sequentially with saturated $NaHCO_3$, water, and brine. The organic phase was dried with $MgSO_4$, filtered, and evaporated. The crude product was purified by silica gel chromatography (gradient from hexanes to 10:1 hexanes/acetone +1% $Et_3N$), yielding 7.8 g of product.

D. 6-O-Methyl-2',4"-bis-O-trimethylsilyl-15-methylerythromycin A9-[O-(1-isopropoxycyclohexyl)]oxime:

A solution of 2',4"-bis-O-trimethylsilyl-15-methylerythromycin A 9-[O-(1-isopropoxycyclohexyl)]oxime (21.7 g, 20.7 mmol) in 41.4 mL of tetrahydrofuran was cooled to 10° C. and treated with 41.4 mL of methylsulfoxide and 20.7 mL of 2.0 M methyl bromide in ether under inert atmosphere. A mixture of methylsulfoxide (41.4 mL) and 1.0 M potassium tert-butoxide in tetrahydrofuran (41.4 mL) was added at a rate of ca. 20 mL per hour. The reaction was monitored by thin-layer chromatography (silica gel, 10:1 toluene/acetone), and was judged complete after addition of 1.6 molar equivalents of base. The reaction was diluted with 200 mL of ethyl acetate and 70 mL of saturated $NaHCO_3$. The mixture was transferred to a separatory funnel, diluted with 850 mL of ethyl acetate and 280 mL of saturated $NaHCO_3$, then washed sequentially with water and brine. The organic phase was dried with $MgSO_4$, filtered through Celite, and evaporated to yield 21.2 g of crude 6-O-methyl-2',4"-bis-O-trimethylsilyl-15-methylerythromycin A 9-[O-(1-isopropoxycyclohexyl)]oxime. This was carried on without further purification.

E. 6-O-Methyl-15-methylerythromycin A 9-oxime:

A solution of 6-O-methyl-2',4"-bis-O-trimethylsilyl-15-methylerythromycin A 9-[O-(1-isopropoxycyclohexyl)]oxime (21.2 g) in 110 mL of acetonitrile was treated with 55 mL of water and 67 mL of acetic acid, and stirred for 8 hours at ambient temperature. The mixture was concentrated en vacuo, then repeatedly concentrated after addition of toluene to yield 19.7 g of 6-O-methyl-15-methylerythromycin A 9-oxime.

F. 6-O-Methyl-15-methylerythromycin A:

A solution of 6-O-methyl-15-methylerythromycin A 9-oxime (19.7 g) and sodium hydrosulfite (85%, 23.1 g) in 280 mL of 1:1 ethanol/water was placed under inert atmosphere. Formic acid (3.75 mL) was added dropwise, and the mixture was stirred at 80° C. for 4.5 hours. After cooling to ambient temperature, the reaction was treated with saturated $NaHCO_3$ and extracted three times with 400-mL portions of ethyl acetate. The organic extracts were combined and washed sequentially with saturated $NaHCO_3$, water, and brine. The organic phase was dried with $MgSO_4$, filtered, and evaporated to yield 15.1 g of 6-O-methyl-15-methylerythromycin A suitable for further conversion.

Example 7

Synthesis of 5-O-(2'-acetyldesosaminyl)-10,11-anhydro-3-deoxy-3-oxo-6-O-methyl-14-norerythronolide A (Anhydro form of Formula (6), $R_a$=Me, $R_d$=Me, $R_c$=Ac, $R_b$=H)

A. 5-O-Desosaminyl-6-O-methyl-14-norerythronolide A:

A mixture of 6-O-methyl-14-norerythromycin A (77 mg), 0.073 ml of 12 N HCl and water (2 ml) was stirred at ambient temperature for 3 hours. The mixture was brought to pH 8 with 8 N KOH, and extracted with ethyl acetate. The organic extract was washed with brine, dried with $MgSO_4$, filtered, and evaporated. The residue was chromatographed on silica gel (3:1/hexanes:acetone, 1% triethylamine) to give pure product as a white solid (42 mg). Mass spectrometry reveals $[M+H]^+$=576.

B. 5-O-(2'-Acetyldesosaminyl)-6-O-methyl-14-norerythronolide A:

A mixture of 5-O-desosaminyl-6-O-methyl-14-norerythronolide A (73 mg), potassium carbonate (20 mg), acetic anhydride (14 µl) and acetone (1 ml) was stirred at ambient temperature for 18 hours. Ethyl acetate was added, washed with water and brine, dried over $MgSO_4$, filtered, and evaporated. The residue was chromatographed on silica gel (3:1/hexanes:acetone, 1% triethylamine) to yield the pure product (71 mg) as a white solid. Mass spectrometry reveals $[M+H]^+$=618.

C. 5-O-(2-Acetyldesosaminyl)-3-deoxy-3-oxo-6-O-methyl-14-norerythronolide A (Formula (1), $R_a$=OH, $R_d$=Me, $R_f$=Me, $R_b$=H $R_c$=Ac):

A solution of 5-O-(2'-acetyldesosaminyl)-6-O-methyl-14-norerythronolide A (99 mg) and 1-(3-dimethylaminopropyl)-3-ethylcarbodiimide (EDC) hydrochloride (206 mg) in dichloromethane (2 ml) was treated with DMSO (0.21 ml) and cooled to 5° C. A solution of pyridinium trifluoroacetate (208 mg) in dichloromethane (2 ml) was added via a syringe pump in 4 hours. Ethyl acetate was then added, washed with saturated $NaHCO_3$, water, brine, and dried over $MgSO_4$, filtered, and evaporated. The residue was chromatographed on silica gel (3:1/hexanes:acetone, 1% triethylamine) to yield the pure product (94 mg) as a white solid. Mass spectrometry reveals $[M+H]^+$=616.

D. 5-O-(2'-Acetyldesosaminyl)-3-deoxy-3-oxo-11-O-methanesulfonyl-6-O-methyl-14-norerythronolide A:

To a solution of 5-O-(2'-acetyldesosaminyl)-3-deoxy-3-oxo-6-O-methyl-14-norerythronolide A (93 mg) in dry pyridine (1 ml) was added methanesulfonyl chloride (0.057 ml) at 5° C. After 3 hours at 5° C., the reaction was warmed to ambient temperature and kept for an additional 15 hours. The mixture was diluted with ethyl acetate, washed with saturated $NaHCO_3$(2×), water (3×), brine, and dried over $MgSO_4$, filtered, and evaporated. The residue was chromatographed on silica gel (2:1 /hexanes:acetone, 1% triethylamine) to yield the pure product (72 mg) as a white solid. Mass spectrometry reveals $[M+H]^+$=695.

E. 5-O-(2'-Acetyldesosaminyl)-10,11-anhydro-3-deoxy-3-oxo-6-O-methyl-14-norerythronolide A:

A solution of 5-O-(2'-acetyldesosaminyl)-3-deoxy-3-oxo-11-O-methanesulfonyl-6-O-methyl-14-norerythronolide A (73 mg) in acetone (1 ml) was treated with diazabicycloundecene (32 µl) at ambient temperature for 18 hours. The mixture was diluted with ethyl acetate, washed with saturated $NaHCO_3$, water, brine, and dried over $MgSO_4$, filtered, and evaporated. The residue was chromatographed on silica gel (2:1/hexanes: acetone, 1% triethylamine) to yield the pure product (50 mg) as a white solid. Mass spectrometry reveals $[M+H]^+$=598. $^{13}$C-NMR ($CDCl_3$, 100 MHz): δ 207.02, 204.50, 169.63, 168.72, 142.52, 139.40, 101.87, 80.61, 80.02, 77.14, 72.66, 71.48, 69.09, 63.56, 51.35, 50.56, 47.12, 40.61, 39.73, 37.36, 30.36, 21.32, 21.06, 20.96, 20.67, 18.45, 14.34, 13.89, 13.55, 13.45.

Example 8

Synthesis of 2'-O-Benzoyl-6-O-methyl-3-descladinosyl-3-oxo-10,11-anhydro-14,15-dehydroerythromycin A (Anhydro form of Formula (6), $R_d$=—CH=$CH_2$, $R_a$=Me, $R_b$=H, $R_c$=Benzoyl)

A. 2'-O-Benzoyl-6-O-methyl-14,15-dehydroerythromycin A

A solution of 6-O-methyl-14,15-dehydroerythromycin A (668 mg), benzoic anhydride (385 mg), and triethylamine (0.25 mL) in 3.6 mL of $CH_2Cl_2$ was stirred for 2 days. After addition of saturated $NaHCO_3$, the mixture was extracted three times with $CH_2Cl_2$. The organic extracts were combined and evaporated to dryness, and the product 2.5 was purified by silica chromatography (90:9:1 toluene/acetone/$Et_3N$) to give 477 mg of product; LC-MS shows $[M+H]^+$=850.6.

B. 2'-O-Benzoyl-6-O-methyl-4",11-bis(O-methanesulfonyl)-14,15-dehydroerythromycin A A solution of 2'-O-benzoyl-6-O-methyl-14,15-dehydroerythromycin A (549 mg) and methanesulfonyl chloride (0.50 mL) in 2.39 mL of pyridine was stirred for 24 hours, then diluted with $CH_2Cl_2$ and saturated $NaHCO_3$. The mixture was extracted three times with $CH_2Cl_2$. The organic extracts were combined and evaporated to dryness, and the product was purified by silica chromatography (90:9:1 toluene/acetone/$Et_3N$) to give 530 mg of product; LC-MS shows $[M+H]^+$=1006.5.

C. 2'-O-Benzoyl-6-O-methyl-4"-O-methanesulfonyl-10,11-anhydro-14,15-dehydroerythromycin A A mixture of 2'-O-benzoyl-6-O-methyl-4",11-bis(O-methanesulfonyl)14,15-dehydroerythromycin A (59 mg) and diazabicycloundecene (0.018 mL) in 0.195 mL of acetone was stirred for 24 hours, then dried in vacuo. The product was purified by silica chromatography (90:9:1 toluene/acetone/$Et_3N$) to give 50 mg of product; LC-MS shows $[M+H]^+$=910.5.

D. 2'-O-Benzoyl-6-O-methyl-3-descladinosyl-10,11-anhydro-14,15-dehydroerythromycin A A mixture of 2'-O-benzoyl-6-O-methyl-4"-O-methanesulfonyl-10,11-anhydro-14,15-dehydroerythromycin A (337 mg), 1.5 mL of acetonitrile, and 6.9 mL of 3 N HCl was stirred for 22 hours. The acetonitrile was removed in vacuo, the pH of the aqueous residue was adjusted to 12 by addition of NaOH, and the product was extracted using 4 portions of $CH_2Cl_2$. The combined extracts were dried and evaporated. The product was purified by silica chromatography (gradient from 96:4 $CH_2Cl_2$/MeOH to 95:4:1 $CH_2Cl_2$/MeOH/$Et_3$N) to give 197 mg, $[M+H]^+$=674.4.

E. 2'-O-Benzoyl-6-O-methyl-3-descladinosyl-3-oxo-10,11-anhydro-14,15-dehydroerythromycin A A suspension of 2'-O-benzoyl-6-O-methyl-3-descladinosyl-10,11-anhydro-14,15-dehydroerythromycin A (226 mg) and the Dess-Martin periodinane (427 mg) in 14.6 mL of $CH_2Cl_2$ (14.6 mL) was stirred for 1 hour. The mixture was diluted with $CH_2Cl_2$ and saturated $NaHCO_3$. The product was extracted using 3 portions of $CH_2Cl_2$, and the extracts were combined, dried, and evaporated. Silica gel chromatography (90:9:1 toluene/acetone/$Et_3$N) yielded the product, 168 mg. $[M+H]^+$=672.4. $^{13}$C-NMR (CDCl$_3$, 100 MHz): δ 206.78, 203 (br), 168.19, 165.08, 141.36, 139.58, 132.74, 131.51, 130.46, 129.79, 128.25, 120.18, 102.09, 80.79, 80.40, 78.70, 72.52, 71.91, 69.19, 63.76, 51.10, 50.54, 47.08, 40.73, 39.87, 37.77, 31.23, 22.13, 20.98, 18.52, 14.28, 14,15, 13.55.

Example 9

Synthesis of 5-O-(2'-acetyldesosaminyl)-10,11-anhydro-3-deoxy-3-oxo-6-O-methyl-15-methylerythronolide A (Anhydro form of Formula (6); $R_a$=Me, $R_d$=propyl, $R_b$=H, $R_c$=Ac)

A. 6-O-methyl-3-descladinosyl-15-methylerythromycin A

A mixture of 6-O-methyl-15-methylerythromycin A (15.1 g) and 280 mL of 0.5 N HCl was stirred at ambient temperature for 3 hours. The pH was adjusted to 9 by addition of 6 N NaOH and the resulting precipitate was collected by vacuum filtration, washed with water, and dried. The filtrate was extracted three times with 400-mL portions of ethyl acetate. The organic extracts were combined, washed sequentially with saturated $NaHCO_3$, water, and brine, then dried over $MgSO_4$, filtered, and evaporated to provide further product. The combined crude products were chromatographed on silica gel to yield 9.35 g of pure 6-O-methyl-3-descladinosyl-15-methylerythromycin A. ES-LC/MS shows $[M+H]^+$=605.

B. 2'-O-Acetyl-6-O-methyl-3-descladinosyl-15-methylerythromycin A

A solution of acetic anhydride (2.92 mL) in 35 mL of ethyl acetate was added dropwise to a solution of 6-O-methyl-3-descladinosyl-15-methylerythromycin A (9.35 g) in 40 mL of ethyl acetate. The mixture was stirred for 30 minutes after completion of addition, then concentrated. Chromatography on silica gel (2:1 hexanes/acetone) gave 8.35 g of 2'-O-acetyl-6-O-methyl-3-descladinosyl-15-methylerythromycin A. ES-LC/MS shows $[M+H]^+$=647.

C. 2'-O-Acetyl-6-O-methyl-3-descladinosyl-3-oxo-15-methylerythromycin A

A solution of 2'-O-acetyl-6-O-methyl-3-descladinosyl-15-methylerythromycin A (8.3 g) and 1-ethyl-3-(dimethylaminopropyl)carbodiimide hydrochloride (16.51 g) in 64 mL of dichloromethane and 15.47 mL of methylsulfoxide was placed under inert atmosphere and cooled on ice. A solution of pyridinium trifluoroacetate (16.63 g) in 64 mL of dichloromethane was added at a rate such that addition would be complete in 4 hours, and the reaction was monitored by thin-layer chromatography. Complete reaction was observed after addition of 73% of the solution and so the reaction was then quenched by addition of 600 mL of ethyl acetate and 200 mL of saturated $NaHCO_3$. The organic layer was collected and washed sequentially with saturated $NaHCO_3$, water, and brine, then dried over $MgSO_4$, filtered, and evaporated to yield 8.4 g of crude product. Chromatography on silica gel (3:1 hexanes/acetone) gave 6.75 g of 2'-O-acetyl-6-O-methyl-3-descladinosyl-3-oxo-15-methylerythromycin A. ES-LC/MS shows $[M+H]^+$=645.

D. 2'-O-Acetyl-6-O-methyl-3-descladinosyl-3-oxo-11-O-methanesulfonyl-15-methylerythromycin A Methanesulfonylchloride (5.68 mL) was added dropwise to a solution of 2'-O-acetyl-6-O-methyl-3-descladinosyl-3-oxo-15-methylerythromycin A (6.73 g) in 35 mL of pyridine at 0° C. The mixture was brought to ambient temperature and quenched by addition of 700 mL of ethyl acetate and 200 mL of saturated $NaHCO_3$. The organic layer was collected and washed sequentially with saturated $NaHCO_3$, water, and brine, then dried over $MgSO_4$, filtered, and evaporated to yield 8.2 g of crude product. Chromatography on silica gel (5:2 hexanes/acetone) gave 5.04 g of 2'-O-acetyl-6-O-methyl-3-descladinosyl-3-oxo-11-O-methanesulfonyl-15-methylerythromycin A. ES-LC/MS shows $[M+H]^+$=723.

E. 2'-O-Acetyl-6-O-methyl-3-descladinosyl-3-oxo-10,11-anhydro-15-methylerythromycin A 1,8-Diazabicyclo[5.4.0]undec-7-ene (5.22 mL) was added dropwise to a solution of 2'-O-acetyl-6-O-methyl-3-descladinosyl-3-oxo-11-O-methanesulfonyl-15-methylerythromycin A (5.03 g) in 23 mL of acetone. The solution was concentrated after 4.5 hours, and the residue was chromatographed on silica gel (5:2 hexanes/acetone) to give 3.72 g of 2'-O-acetyl-6-O-methyl-3-descladinosyl-3-oxo-10,11-anhydro-15-methylerythromycin A. ES-LC/MS shows $[M+H]^+$=627.

Example 10

Synthesis of 5-O-(2'-acetyldesosaminyl)-10,11-anhydro-3,6-dideoxy-3-oxo-15-methylerythronolide A (Formula (6), anhydro form, $R_d$=propyl, $OR_a$ replaced by H, $R_b$=H, $R_c$=Ac)

To a solution of 6-deoxy-15-methyl erythromycin C (220mg, 0.307mmol) in dichloromethane (5 mL) were given potassium carbonate (50 mg) and acetic anhydride (100 L, 0.9 mmol), and the reaction was stirred at room temperature for 16 hours. The solution was filtered, sodium hydroxide (1N, 25 mL) and brine (25 mL) added and the aqueous layer was extracted with ethyl acetate 6 times. The combined organic layers were dried with sodium sulfate, filtered, and the solvent removed in vacuo. The crude product the 2' acetylated form of the starting material was carried on to the next step.

The crude product was dissolved in pyridine (5 mL) and mesyl chloride (70L, 0.9mmol) was added. The reaction was stirred at −20° C. for 2 days, poured on sodium hydroxide (1N, 25 mL) and brine (25 mL) and the aqueous layer was extracted with ethyl acetate 6 times. The combined organic layers were dried with sodium sulfate, filtered, and the solvent removed in vacuo. The residue was purified by chromatography on silica gel (toluene/acetone=3:1, 1% ammonium hydroxide) to yield 11,4" dimesylated form (190 mg, 68% over two steps).

The 11,4" dimesylated form (190 mg, 0.21 mmol) was dissolved in acetone (7 mL) and DBU (63L, 0.42 mmol) was added, and the reaction was stirred at room temperature overnight. The mixture was poured on sodium hydroxide (1N, 25 mL) and brine (25 mL) and the aqueous layer was extracted with ethyl acetate 6 times. The combined organic layers were dried with sodium sulfate, filtered, and the solvent removed in vacuo. The crude product, the 10,11-dehydro form of 6-deoxy-15-methyl erythromycin was carried on to the next step.

To the crude product from the above step was added hydrochloric acid (30 mL, 3N) and ethanol (2 mL) and the mixture was stirred vigorously for 6 hours. Sodium hydroxide (5 mL, 10N) was added and the aqueous layer was extracted with ethyl acetate 6 times. The combined organic layers were dried with sodium sulfate, filtered, and the solvent removed in vacuo. The crude product, the anhydro form of formula (6) (but with OH at position 3) where $R_d$=propyl, $OR_a$ is replaced by H, $R_b$=$R_c$=H, was carried on to the next step.

To the crude product from the above step in dichloromethane (5 mL) was added acetic anhydride (50L, 0.45 mmol) and potassium carbonate (100 mg) and the mixture was stirred vigorously for 9 hours. The reaction was filtered, sodium hydroxide (20 mL, 1N) and brine (25 mL) were added and the aqueous layer was extracted with ethyl acetate 6 times. The combined organic layers were dried with sodium sulfate, filtered, and the solvent removed in vacuo. The residue was purified by chromatography on silica gel (toluene/acetone=3:1, 1% ammonium hydroxide) to yield the 2' acetylated form of the starting material (110 mg, 89% over three steps).

The product of the above step (110 mg, 0.184 mmol) was dissolved in dichloromethane (10 mL) and Dess-Martin reagent (220 mg, 0.53 mmol) was added. The reaction was stirred at room temperature for 45 min. The reaction was quenched with Sodium hydroxide (20 mL, 1N) and brine (25 mL) and the aqueous layer was extracted with ethyl acetate 6 times. The combined organic layers were dried with sodium sulfate, filtered, and the solvent removed in vacuo. The residue was purified by chromatography on silica gel (toluene/acetone, gradient=6:1–3:1, 1% ammonium hydroxide) to yield the compound of formula (6), anhydro form, where $R_d$=propyl, $OR_a$ is replaced by H, $R_b$=H, $R_c$=Ac (94 mg, 86%).

Example 11

I. Compound of Formula Formula (4): $R_d$=propyl, $R_a$=allyl

Step 1. Allylation of Intermediate Antibiotic at 6-OH:

A solution of 2',4"-bis-O-trimethylsilyl-15-methylerythromycin A 9-[O-(1-isopropoxycyclohexyl)] oxime (formula (I) ($R_a$ is OH, $R_d$ is propyl, protected at 2' and 4" with trimethylsilyl and at C9=O by the isoproxycyclohexyl oxime)) (7.8 g, 7.44 mmol) in 30 mL of tetrahydrofuran was cooled on ice and treated with 30 mL of methylsulfoxide and 2.58 mL of freshly distilled allyl bromide under inert atmosphere. A mixture of methylsulfoxide (29.8 mL) and 1.0 M potassium tert-butoxide in tetrahydrofuran (29.8 mL) was added at a rate of 1.33 molar equivalents of base per hour. The reaction was monitored by thin-layer chromatography (silica gel, 10:1 toluene/acetone), and was judged complete after addition of 3.6 molar equivalents of base. The reaction was diluted with 700 mL of ethyl acetate and washed sequentially with saturated $NaHCO_3$, water, and brine. The organic phase was dried with $MgSO_4$, filtered, and evaporated to yield 8.08 g of crude 6-O-allyl-2',4"-bis-O-trimethylsilyl-15-methylerythromycin A 9-[O-(1-isopropoxycyclohexyl)]oxime. This was carried on without further purification.

Step 2: A solution of 6-O-allyl-2',4"-bis-O-trimethylsilyl-15-methylerythromycin A 9-[O-(1-isopropoxycyclohexyl)] oxime (8.08 g) in 42 mL of acetonitrile was treated with 21 mL of water and 24 mL of acetic acid, and stirred for 18 hours at ambient temperature. The mixture was concentrated after addition of 2-propanol, then repeatedly after addition of toluene to yield 7.7 g of crude product. Chromatography on silica gel (gradient from 2:1 to 1:1 hexanes/acetone +1% $Et_3N$) gave 3.75 g of 6-O-allyl-15-methylerythromycin A 9-oxime.

Step 3: A solution of 6-O-allyl-15-methylerythromycin A 9-oxime (3.75 g) and sodium hydrosulfite (85%, 5.37 g) in 66 mL of 1:1 ethanol/water was placed under inert atmosphere. Formic acid (0.845 mL) was added dropwise, and the mixture was stirred at 80° C. for 3.5 hours. After cooling to ambient temperature, the reaction was adjusted to pH 10 with 6 N NaOH and extracted three times with 150-mL portions of ethyl acetate. The organic extracts were combined and washed sequentially with saturated $NaHCO_3$, water, and brine. The organic phase was dried with $MgSO_4$, filtered, and evaporated to yield 3.42 g of 6-O-allyl-15-methylerythromycin A suitable for further conversion.

II. Compound of Formula (4): $R_d$=Me, $R_a$=allyl

Step 1: Allylation of Intermediate Antibiotic at 6-OH:

A solution of 2',4"-bis-O-trimethylsilyl-14-norerythromycin A 9-[O-(1-isopropoxycyclohexyl)]oxime, Formula (I), ($R_a$ is OH, $R_d$ is methyl, protected at 2' and 4" with trimethylsilyl and at C9=O by the isoproxycyclohexyl oxime) (202 mg) in tetrahydrofuran (0.4 mL), DMSO (0.4 mL), and ether (0.04 mL) was cooled to 10° C. and treated with 0.035 mL of freshly distilled allyl bromide under inert atmosphere. A mixture of methylsulfoxide (0.4 mL) and 1.0 M potassium tert-butoxide in tetrahydrofuran (0.4 mL) was added at a rate 0.22 mL/hour. The reaction was monitored by thin-layer chromatography (silica gel, 5:1 toluene/acetone. The reaction was diluted with ethyl acetate and washed sequentially with saturated $NaHCO_3$, water, and brine. The organic phase was dried with $MgSO_4$, filtered, and evaporated to yield 222 mg of crude 6-O-allyl-2',4"-bis-O-trimethylsilyl-14-norerythromycin A 9-[O-(1-isopropoxycyclohexyl)]oxime. This was carried on without further purification.

Step 2: A solution of 6-O-allyl-2',4"-bis-O-trimethylsilyl-14-norerythromycin A 9-[O-(1-isopropoxycyclohexyl)] oxime (222 mg) in 4 mL of acetonitrile was treated with 2 mL of water and 2.4 mL of acetic acid, and stirred for 18 hours at ambient temperature. The mixture was concentrated after addition of 2-propanol, then repeatedly after addition of toluene to yield 220 mg of crude 6-O-allyl-14-norerythromycin A 9-oxime.

Step 3: A solution of 6-O-allyl-14-norerythromycin A 9-oxime (220 mg) and sodium hydrosulfite (85%, 322 mg) in 4 mL of 1:1 ethanol/water was placed under inert atmosphere. Formic acid (0.050 mL) was added dropwise, and the mixture was stirred at 80° C. for 15 hours. After cooling to ambient temperature, the reaction was adjusted to pH 10 with 6 N NaOH and extracted three times with 150-mL portions of ethyl acetate. The organic extracts were combined and washed sequentially with saturated $NaHCO_3$, water, and brine. The organic phase was dried with $MgSO_4$, filtered, and evaporated to yield 156 mg of 6-O-allyl-14-norerythromycin A suitable for further conversion.

Other embodiments: In a similar manner, compounds of formula (4) wherein Y and Z are, together, =O, $R_a$ is allyl, is prepared from an intermediate where $R_d$ is butyl, benzyl, vinyl, or 3-hydroxybutyl.

Example 12

Conversion to Formula (4) to Formula (6)

Step 1. A mixture of the compound prepared in Example 11, II (77 mg, crude), 0.073 ml of 12 N HCl and water (2 ml) was stirred at ambient temperature for 3 hours. The mixture was brought to pH 8 with 8 N KOH, and extracted with ethyl acetate. The organic extract was washed with brine, dried with $MgSO_4$, filtered, and evaporated. The residue was chromatographed on silica gel (3:1/hexanes:acetone, 1% triethylamine) to give pure product as a white solid (42 mg).

Step 2. To protect the 2' OH, a mixture the above compound (73 mg), potassium carbonate (20 mg), acetic anhydride (14 $\mu$l) and acetone (1 ml) was stirred at ambient temperature for 18 hours. Ethyl acetate was added, washed with water and brine, dried over $MgSO_4$, filtered, and evaporated. The residue was chromatographed on silica gel (3:1/hexanes:acetone, 1% triethylamine) to yield the pure product (71 mg) as a white solid.

Step 3. A solution of the compound resulting from step 2 (99 mg) and 1-(3-dimethylaminopropyl)-3-ethylcarbodiidmide (EDC) hydrochloride (206 mg) in dichloromethane (2 ml) was treated with DMSO (0.21 ml) and cooled to 5° C. A solution of pyridinium trifluoroacetate (208 mg) in dichloromethane (2 ml) was added via a syringe pump in 4 hours. Ethyl acetate was then added, washed with saturated $NaHCO_3$, water, brine, and dried over $MgSO_4$, filtered, and evaporated. The residue was chromatographed on silica gel (3:1/hexanes:acetone, 1% triethylamine) to yield the pure compound of formula (6) (94 mg, $R_a$ is allyl, $R_c$ is acetate and $R_d$ is $CH_3$).

Step 4. To deprotect 2' OH, a solution of the compound resulting from step 3 (94 mg) in 5 mL methanol was stirred at room temperature for 24 hours. The solvent was removed in vacuo to give the desired compound of formula (6) ($R_a$ is allyl, $R_c$ is H, and $R_d$ is $CH_3$).

Other embodiments: In a similar manner, compounds of formula (4) wherein $R_a$ is allyl, $R_c$ is H, and $R_d$ is propyl, butyl, benzyl, vinyl, or 3-hydroxybutyl is prepared.

Example 13

Preparation of Compounds of Formula (5)

The compound of formula (4), prepared as the 6-allyl derivative in Example 11, is protected at the 2' position, treated with acid and dehydrated, then deprotected to obtain the compound of formula (5), as shown in FIG. 1, wherein $R_c$ is H, and $R_a$ is allyl. Similarly, compounds of formula (6) wherein $R_d$ is propyl, butyl, benzyl, vinyl, or 3-hydroxybutyl, are prepared as described above using as starting material the compounds of formula (I) wherein $R_d$ is as set forth above.

Example 14

Conversion of =O at Position 9 to =NOH

According to the procedure of Example 6A, the carbonyl at position 9 of erythromycins are converted to the corresponding oximes.

Example 15

Conversions at —$OR_a$

A. Ally→Propyl

A solution of any of the compounds prepared above (0.2 mmol) in ethanol is flushed with nitrogen and 10% palladium on carbon (20 mg) added. The mixture is then flushed with hydrogen and the reaction mixture stirred overnight under positive hydrogen pressure. The reaction mixture is filtered and concentrated in vacuo to give a glass. Chromatography on silica gel (95:5:0.5 dichloromethane-methanol-ammonia) gives the propyl compounds as white solids.

B. Allyl→—$CH_2CHO$

Ozone is passed through a −78° C. solution in dichloromethane (100 mL) of any of the compounds resulting above (4.0 mmol) for 45 minutes. The reaction mixture is then flushed with nitrogen for 10 minutes. Dimethyl sulfide (1.46 mL, 20 mmol) is added at −78° C. and the reaction mixture stirred for 30 minutes at 0° C. The reaction mixture is concentrated in vacuo to give a white foam which is used without further purification by heating a solution of the compound in THF (40 mL, 4.0 mmol) and triphenylphosphine (2.62 g, 10.0 mmol) at 55° C. for 2.5 hours. The reaction mixture is concentrated in vacuo to give a white foam. Chromatography on silica gel (1:1 acetone-hexane, then 75:25:0.5 acetone-hexane-triethylamine) gives the desired compound as a white solid.

C. Allyl→—$CH_2CH=NOH$

To a solution in methanol (5 mL) of the compound prepared in B wherein $R_a$ is —$CH_2CHO$, (0.08 mmol) is added triethylamine (31 $\mu$L, 0.225 mmol) and hydroxylamine hydrochloride (7.7 mg, 0.112 mmol) and the reaction mixture stirred for 6 hours at ambient temperature. The reaction mixture is taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gives the compound as a white solid.

D. —$CH_2CH=NOH$→—$CH_2CN$

To a solution under nitrogen of the compound prepared in C (0.267 mmol) in THF (5 mL) is added diisopropylcarbodiimide (83 $\mu$L, 0.534 mmol) and CuCl (2.7 mg, 0.027 mmol) and the reaction mixture is stirred overnight at ambient temperature. The reaction mixture is taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gives the desired compound as a white solid.

E. —$CH_2CHO$→—$CH_2CH_2NH_2$

To a solution in methanol (10 mL) of the compound prepared in B (0.276 mmol) is added ammonium acetate (212 mg, 2.76 mmol) and the mixture is cooled to 0° C. Sodium cyanoborohydride (34 mg, 0.553 mmol) is added and the reaction mixture stirred for 30 hours at 0° C. The reaction mixture is taken up in ethyl acetate and washed with aqueous 5% sodium carbonate, aqueous 2% tris (hydroxymethyl)aminomethane, and brine, dried over sodium sulfate, filtered, and concentrated in vacuo. Chromatography on silica gel (90:10:0.5 dichloromethane-methanol-ammonia) gives the desired compound as a white solid.

F. —$CH_2CHO$→—$CH_2CH_2NHCH_2$-Phenyl

To a 0° C. solution in methanol (10 mL) of the compound prepared in B (0.200 mmol) is added acetic acid (114 $\mu$L, 2.00 mmol) and benzylamine (218 $\mu$L, 2.00 mmol) and the mixture is stirred for 10 minutes. Sodium cyanoborohydride (24.8 mg, 0.400 mmol) is added and the reaction mixture stirred for 16 hours. Additional sodium cyanoborohydride (24.8 mg, 0.400 mmol) is then added and stirring continued for 5 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) followed by a second chromatography (50:50:0.5 acetone-hexanes-triethylamine) gives the desired compound as a white foam.

G. —$CH_2CHO$→—$CH_2CH_2NHCH_2CH_2$-Phenyl

To a 0° C. solution in methanol (10 mL) of the compound prepared in B (0.200 mmol) is added acetic acid (114 μL, 2.00 mmol) and phenethylamine (218 μL, 2.00 mmol) and the mixture stirred for 10 minutes. Sodium cyanoborohydride (24.8 mg, 0.400 mmol) is added and the reaction mixture stirred for 16 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gives the desired compound.

H. —$CH_2CHO$→—$CH_2CH_2NHCH(CO_2CH_3)CH_2$-Phenyl

To a 0° C. solution in methanol (10 mL) of the compound prepared in B (0.200 mmol) is added L-phenylalanine methyl ester hydrochloride (129 mg, 0.600 mmol) and the mixture stirred for 10 minutes. Sodium cyanoborohydride 924.8 mg, 0.400 mmol) is added and the reaction mixture stirred for 22 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) gives the desired compound.

I. —$CH_2CHO$→—$CH_2CH_2NHCH_2$-(4-pridyl)

The desired compound is prepared according to the method in G, except substituting 4-aminomethylpyridine for phenethylamine.

J. —$CH_2CH_2NH_2$→—$CH_2CH_2NHCH_2$-(4-quinolyl)

To a solution of the compound prepared in E (0.15 mmol) in methanol (2 mL) is added 4-quinolinecarboxaldehyde (23 mg, 0.15 mmol), acetic acid (8.6 μL, 0.15 mmol), and sodium cyanoborohydride (9.4 mg, 0.15 mmol) and the reaction mixture is stirred for 15 hours. The reaction mixture is taken up in ethyl acetate and washed with aqueous 5% sodium carbonate, aqueous 2% tris(hydroxymethyl) aminomethane, and brine, dried over sodium sulfate, filtered, and concentrated in vacuo. Chromatography on silica gel (95:10:0.5 dichloromethane-methanol-ammonia) gives the desired compound.

K. Allyl→—$CH_2CH$=$CH$-Phenyl

To a solution under nitrogen of the 2' protected compound prepared in Example 10 (1.00 mmol), palladium(II)acetate (22 mg, 0.100 mmol), and triphenylphosphine (52 mg, 0.200 mmol) in acetonitrile (5 mL) was added iodobenzene (220 μL, 2.00 mmol) and triethylamine (280 μL, 2.00 mmol) and the mixture is cooled to −78° C., degassed, and sealed. The reaction mixture is then warmed to 60° C. for 0.5 hours and stirred at 80° C. for 12 hours, taken up in ethyl acetate and washed twice with aqueous 5% sodium bicarbonate, once with aqueous 2% tris(hydroxymethyl)aminomethane, and once with brine, dried over sodium sulfate, filtered, and concentrated in vacuo. Chromatography on silica gel (95:5:0.5 dichloromethane-methanol-ammonia) gives the desired compound.

Deprotection is accomplished by heating in methanol.

Other embodiments of formulas (4)–(6) where $R_b$ is H, $R_c$ is H, and $R_d$ is propyl, butyl, benzyl, vinyl, or 3-hydroxybutyl are those wherein $R_a$ is:

| | |
|---|---|
| —$CH_2CH_2CH_2$-phenyl; | —$CH_2CH$=$CH$-(4-methoxyphenyl); |
| —$CH_2CH$=$CH$-(4-chlorophenyl); | —$CH_2CH$=$CH$-(3-quinolyl); |
| —$CH_2CH_2CH_2OH$; | —$CH_2C(O)OH$; |
| —$CH_2CH_2NHCH_3$; | —$CH_2CH_2NHCH_2OH$; |
| —$CH_2CH_2N(CH_3)_2$; | —$CH_2CH_2$(1-morpholinyl); |
| —$CH_2C(O)NH_2$; | —$CH_2NHC(O)NH_2$; |
| —$CH_2NHC(O)CH_3$; | —$CH_2F$; |
| —$CH_2CH_2OCH_3$; | —$CH_2CH_3$; |
| —$CH_2CH$=$CH(CH_3)_2$; | —$CH_2CH_2CH(CH_3)CH_3$; |
| —$CH_2CH_2OCH_2CH_2OCH_3$; | —$CH_2SCH_3$; |
| -cyclopropyl; | —$CH_2OCH_3$; |
| —$CH_2CH_2F$; | —$CH$-cyclopropyl; |
| —$CH_2CH_2CHO$; | —$C(O)CH_2CH_2CH_3$; |
| —$CH_2$-(4-nitrophenyl); | —$CH_2$-(4-chlorophenyl); |
| —$CH_2$-(4-methoxyphenyl); | —$CH_2$-(4-cyanophenyl); |
| —$CH_2CH$=$CHC(O)OCH_3$; | —$CH_2CH$=$CHC(O)OCH_2CH_3$; |
| —$CH_2CH$=$CHCH_3$; | —$CH_2CH$=$CHCH_2CH_3$; |
| —$CH_2CH$=$CHCH_2CH_2CH_3$; | —$CH_2CH$=$CHSO_2$-phenyl; |
| —$CH_2C$≡$CSi(CH_3)_3$ | —$CH_2C$≡$CCH_2CH_2CH_2CH_2CH_3$; |
| —$CH_2C$≡$CCH_3$; | —$CH_2$-(2-pyridyl); |
| —$CH_2$-(3-pyridyl); | —$CH_2$-(4-pyridyl); |
| —$CH_2$-(4-quinolyl); | —$CH_2NO_2$; |
| —$CH_2C(O)OCH_3$; | —$CH_2C(O)$-phenyl; |
| —$CH_2C(O)CH_2CH_3$; | —$CH_2Cl$; |
| —$CH_2S(O)_2$-phenyl; | —$CH_2CH$=$CHBr$; |
| —$CH_2CH$=$CH$-(4-quinolyl); | —$CH_2CH_2CH_2$-(4-quinolyl); |
| —$CH_2CH$=$CH$-(5-quinolyl); | —$CH_2CH_2CH_2$-(5-quinolyl); |
| —$CH_2CH$=$CH$-(4-benzoxazolyl); or | —$CH_2CH$=$CH$-(7-benzimidazolyl). |

Any of the foregoing compounds can be converted to the corresponding derivatives wherein Y and Z are together =NOH in the manner described in Example 14 above.

Example 16

Preparation of Compound of Formula (1): L is CO, T is O, $R_a$=—$CH_2CH$=$CH_2$, $R_c$ is H Step 1. Protection at 2'-OH to Form Intermediate Compound of Compound (6) Having Hydroxyl Group at C-3, $R_a$ is Allyl and $R_c$ is Benzoyl.

To a solution of the product of Example 12 or other embodiment thereof wherein $R_d$ is propyl, butyl, benzyl, vinyl or 3-hydroxybutyl (2.49 g, 4.05 mmol) in dichloromethane (20 mL) is added benzoic anhydride (98%, 1.46 g, 6.48 mmol) and triethylamine (0.90 mL, 6.48 mmol) and the white suspension is stirred for 26 hours at ambient temperature. Aqueous 5% sodium carbonate is added and the mixture is stirred for 20 minutes. The mixture is extracted with dichloromethane. The organic phase is washed with aqueous 5% sodium bicarbonate, and brine, dried over sodium sulfate and concentrated in vacuo to give a white foam. Chromatography on silica gel (30% acetone-hexanes) gives the protected compound.

Step 2. Oxidation to Form Compound (6), $R_a$ is allyl, $R_c$ is Benzoyl.

To a −10° C. solution under $N_2$ of N-chlorosuccinimide (0.68 g, 5.07 mmol) in dichloromethane (20 mL) is added dimethylsulfide (0.43 mL, 5.92 mmol) over 5 minutes. The resulting white slurry is stirred for 20 minutes at −10° C. and then a solution of the compound resulting from step 1 (2.43 g, 3.38 mmol) in dichloromethane (20 mL) is added and the reaction mixture is stirred for 30 minutes at −10 to −5° C. Triethylamine (0.47 mL, 3.38 mmol) is added dropwise over 5 minutes and the reaction mixture is stirred for 30 minutes at 0° C. The reaction mixture is extracted with dichloromethane. The organic phase is washed twice with aqueous 5% sodium bicarbonate and once with brine, dried over sodium sulfate, and concentrated in vacuo to give a white foam. Chromatography on silica gel (30% acetone-hexanes) gives the oxidized compound.

Step 3: Form Cyclic Carbonate of Compound of Formula (1) from Illustrative Scheme 5: $R_a$ is —$CH_2CH=CH_2$, $R_c$ is Benzoyl.

To a −35° C. solution under nitrogen in THF (60 mL) of the compound prepared in step 2 (3.58 g, 5.00 mmol) is added sodium hexamethyldisilazide (1.0 M in THF, 5.5 mL, 5.5 mmol) and the resulting white suspension is stirred for 30 minutes. A solution of carbonyldiimidazole (4.05 g, 25 mmol) in THF (40 mL) is added dropwise over 20 minutes at −35° C. and then the cold bath is removed and the reaction mixture is stirred for 30 minutes. The reaction mixture is taken up in ethyl acetate and washed with aqueous 5% sodium bicarbonate and brine, dried over sodium sulfate, filtered, and concentrated in vacuo. Chromatography on silica gel (30% acetone-hexane) gives the dehydrated compound (2.6 g) as a white foam. $(M+H)^+$ is 744.

Step 4. Deprotection to Form Compound of Formula (1): L is CO, T is O, $R_a$ is —$CH_2CH=CH_2$, $R_c$ is H.

A solution of the compound resulting from step 3 (719 mg, 1.0 mmol) in methanol (20 mL) is stirred at reflux for 6 hours. The reaction mixture is concentrated in vacuo and the residue is purified by chromatography on silica gel (95:5:0.5 dichloromethane-methanol-ammonia) to give the desired compound.

Example 17

Compound of Formula (1): L is CO, T is O, $R_a$ is —$CH_2CH=CH$-Phenyl

A. Form Cyclic Carbonate of Compound of Formula (1) from Ilustrative Scheme 5: $R_a$ is —$CH_2CH=CH$-Phenyl, $R_c$ is Benzoyl.

A solution of the compound prepared in Example 15, step K or other embodiments wherein $R_d$ is propyl, butyl, benzyl, vinyl, or 3-hydroxybutyl (150 mg, 0.20 mmol) in THF (5 mL) is cooled to −35° C. and flushed with nitrogen. Lithium hexamethyldisilazide (1.0 M in THF, 0.22 mL, 0.22 mmol) over 2 minutes at −35° C. The reaction mixture is stirred for 10 minutes at −35° C. and then a solution of carbonyldimidazole (162 mg, 1.00 mmol) in THF (3 mL) is added dropwise over 2 minutes. The cold bath is removed and the reaction mixture is stirred for 30 minutes. The reaction mixture is cooled to 0° C. and aqueous 0.5 M $KH_2PO_4$ is added. The mixture is extracted with ethyl acetate and the organic phase is washed with brine, dried over sodium sulfate, and concentrated in vacuo. Chromatography on silica gel (30% acetone-hexane) gives the dehydrated compound.

B. Deprotection to Form Compound of Formula (1): L is CO, T is O, $R_a$ is —$CH_2CH=CH$-Phenyl, $R_c$ is H Deprotection of the compound prepared in step A is accomplished by heating in methanol according to the procedure of Example 16, step 4.

Using the procedures described in the preceding examples and schemes and methods known in the synthetic organic chemistry art, the compounds of Formula (1) wherein L is CO and T is O can be prepared. These compounds include one of the $R_a$ substituents listed below:

| | |
|---|---|
| —$CH_2CH_2CH_3$ | —$CH_2CH_2NH_2$ |
| —$CH_2CH=NOH$ | —$CH_2CH_2CH_2OH$ |
| —$CH_2F$ | —$CH_2$-phenyl |
| —$CH_2CH_2$-(4-pyridyl) | —$CH_2CH_2$-(4-quinolyl) |

-continued

| | |
|---|---|
| —$CH_2CH(OH)CN$ | —$CH(C(O)OCH_3)CH_2$-phenyl |
| —$CH_2CN$ | —$CH_2CH=CH$-(4-methoxyphenyl) |
| —$CH_2CH=CH$-(4-fluorophenyl) | —$CH_2CH=CH$-(8-quinolyl) |
| —$CH_2CH_2NHCH_2$-phenyl | —$CH_2$-phenyl |
| —$CH_2$-(4-pyridyl) | —$CH_2$-(4-quinolyl) |
| —$CH_2CH=CH$-(4-pyridyl) | —$CH_2CH_2CH_2$-(4-pyridyl) |
| —$CH_2CH=CH$-(4-quinolyl) | —$CH_2CH_2CH_2$-(4-quinolyl) |
| —$CH_2CH=CH$-(5-quinolyl) | —$CH_2CH_2CH_2$-(5 quinolyl) |
| —$CH_2CH=CH$-(4-benzoxazolyl) | —$CH_2CH=CH$-(4-benzimidazolyl) |

Example 18

Preparation of Compound of Formula (1): L is CO, T is NH, $R_a$ is —$CH_2CH=CH_2$), $R_c$ is H Step 1: Preparation to Form 10, 11 Anhydro Form of Intermediate Compound (6): $R_a$ is —$CH_2CH=CH_2$, $R_c$ is Benzoyl.

A. 6-O-allyl-3-descladinosyl-15-methyl-erythromycin A

A mixture of 6-O-allyl-15-methylerythromycin A (6.58 g) and 125 mL of 0.5 N HCl was stirred at ambient temperature for 20 hours. The pH was adjusted to 10 by addition of 6 N NaOH, and the mixture was extracted three times with 225-mL portions of ethyl acetate. The organic extracts were combined, washed sequentially with saturated $NaHCO_3$, water, and brine, then dried over $MgSO_4$, filtered, and evaporated. The crude product was chromatographed on silica gel (3:2 toluene/acetone +1% $Et_3N$) to yield 3.04 g of pure 6-O-allyl-3-descladinosyl-15-methylerythromycin A. ES-LC/MS shows $[M+H]^+=617$.

B. 2'-O-Benzoyl-6-O-allyl-3-descladinosyl-15-methyl-erythromycin A

6-O-Allyl-3-descladinosyl-15-methylerythromycin A (2.43 g, 3.86 mmol, 1.00 eq) and benzoic anhydride (1.78 g, 7.72 mmol, 2.00 eq) were placed in a round-bottomed flask and flushed with $N_2$. Ethyl acetate (17.5 mL) was added. The solution was stirred for 3.5 h and then diluted with 400 mL of EtOAc and washed twice with 150 mL of saturated aqueous $NaHCO_3$ and once each with 150 mL of water and brine. The organic phase was dried over $MgSO_4$, filtered, and concentrated. Purification by flash chromatography over silica gel (3:1 hexanes:acetone +1% $Et_3N$) gave 1.94 g (68.1%) of the desired product as a white solid. ES-LC/MS shows $[M+H]^+=721$. $^{13}C$ NMR (100.6 MHz, $CDCl_3$) δ 219.4, 174.3, 165.4, 135.3, 132.6, 130.8, 129.7, 128.2, 117.2, 99.7, 80.7, 79.0, 77.9, 77.7, 75.1, 74.3, 72.3, 69.0, 64.7, 63.3, 45.6, 43.9, 40.7, 37.9, 37.7, 35.7, 32.1, 30.8, 21.1, 20.2, 19.3, 18.1, 16.3, 15.1, 14.0, 12.4, 7.7.

C. 2'-O-Benzoyl-6-O-allyl-3-descladinosyl-3-oxo-15-methyl-erythromycin A

N-Chlorosuccinimide (0.510 g, 3.82 mmol, 1.50 eq) was dissolved in 13 mL of anhydrous $CH_2Cl_2$ and cooled to −10° C. under $N_2$. Methyl sulfide (0.328 mL, 4.46 mmol, 1.75 eq) was added, and the reaction was stirred for 15 min. A solution of 2'-O-benzoyl-6-O-allyl-3-descladinosyl-15-methylerythromycin A (1.87 g, 2.55 mmol, 1.00 eq) in 13 mL of anhydrous $CH_2Cl_2$ was added dropwise. After 30 min, freshly distilled $Et_3N$ (0.355 mL, 2.55 mmol, 1.00 eq) was added; and the reaction was brought up to 0° C. over 30 min. The reaction mixture was diluted with 400 mL EtOAc and washed successively with 100 mL each of saturated aqueous $NaHCO_3$, water, and brine. The organic layer was dried over $MgSO_4$, filtered, concentrated, and purified by flash chromatography (9:1 hexanes:acetone +1% $Et_3N$) to give 0.931 g (49.9%) of the desired product as a white solid. ES-LC/MS shows $[M+H]^+=719$. $^{13}C$ NMR (100.6 MHz, $CDCl_3$) δ

219.1, 206.1, 169.5, 165.3, 135.3, 132.7, 129.0, 129.7, 128.3, 117.4, 100.7, 78.5, 76.6, 75.3, 74.2, 72.1, 69.2, 69.0, 64.5, 63.7, 50.6, 45.3, 44.8, 40.7, 38.3, 37.8, 31.7, 31.0, 21.1, 20.2, 19.5, 18.1, 16.5, 14.5, 14.0, 12.6, 12.2.

D. 2'-O-Benzoyl-6-O-allyl-3-descladinosyl-3-oxo-11-O-methanesulfonyl-15-methyl-erythromycin A 2'-O-Benzoyl-6-O-Allyl-3-descladinosyl-3-oxo-15-methylerythromycin A (904 mg, 1.24 mmol, 1.00 eq) was dissolved in freshly distilled pyridine (4 mL) and cooled to 0° C. Methanesulfonyl chloride (0.478 mL, 6.17 mmol, 5.00 eq) was added dropwise. The reaction was allowed to come to ambient temperature and stirred overnight. The mixture was diluted with 350 mL of EtOAc and quenched with 100 mL of saturated aqueous $NaHCO_3$. The layers were separated, and the organic phase was washed successively with 100 mL each of water and brine. The organic phase was dried over $MgSO_4$, filtered, and concentrated. Flash chromatography over silica gel (4:1 hexanes:acetone +1% $Et_3N$) gave 741 mg (74.1%) of the desired compound as a white solid. $^{13}C$ NMR (100.6 MHz, $CDCl_3$) δ 203.0, 168.9, 165.0, 137.6, 133.1, 130.3, 129.8, 128.5, 114.4, 108.8, 102.2, 91.1, 84.4, 81.6, 78.8, 72.2, 69.2, 64.3, 63.9, 52.1, 46.6, 45.8, 40.7, 38.8, 38.2, 35.9, 31.8, 30.9, 29.7, 24.8, 21.0, 19.6, 18.2, 15.5, 15.4, 13.8, 13.5.

E. 2'-O-Benzoyl-6-O-allyl-3-descladinosyl-3-oxo-10,11-anhydro-15-methyl-erythromycin A 2'-O-Benzoyl-6-O-allyl-3-descladinosyl-3-oxo-11-methanesulfonyl-15-methyl-erythromycin A (705 mg, 0.870 mmol, 1.00 eq) was dissolved in acetone (3 mL), and 1,8-diazabicyclo[5.4.0]undec-7-ene (0.651 mL, 4.35 mmol, 5.00 eq) was added dropwise. The reaction was stirred at ambient temperature for 6 h and then concentrated. Flash chromatography over silica gel (4:1 hexanes:acetone +1% $Et_3N$) gave 486 mg (78.0%) of the desired compound as a white solid. $^{13}C$ NMR (100.6 MHz, $CDCl_3$) δ 210.1, 208.4, 170.2, 165.2, 141.0, 140.2, 136.3, 132.7, 130.4, 129.8, 128.2, 115.5, 100.6, 81.0, 78.7, 77.2, 73.8, 72.0, 69.1, 64.6, 63.3, 51.0, 47.4, 40.8, 39.4, 36.2, 31.9, 31.3, 23.6, 21.2, 21.1, 21.0, 19.4, 14.1, 13.9, 13.7, 13.1.

Step 2: Formation of Imidazolide Intermediate (7) from Illustrative Scheme 3 and Cyclization to Form Cyclic Carbamate of Compound (1)/(10): $R_a$ is —$CH_2CH=CH_2$, $R_c$ is benzoyl.

2'-O-Benzoyl-6-O-allyl-10,11-anhydro-3-descladinosyl-3-oxo-15-methyl-erythromycin A (227 mg, 0.317 mmol, 1.00 eq) was dissolved in 1.3 mL of freshly distilled THF and cooled to −15° C. under $N_2$. Sodium hydride (25 mg of a 60% dispersion in mineral oil, 0.634 mmol, 2.00 eq) was added, and the reaction was stirred for 15 min. A solution of 1,1-carbonyldiimidazole (140 mg, 0.866 mmol, 3.00 eq) in 1.3 mL of freshly distilled THF was added dropwise. After stirring for 30 min, the reaction was allowed to warm to ambient temperature over 1.5 h. The mixture was diluted with 100 mL of EtOAc and washed successively with 30 mL each of saturated aqueous $NaHCO_3$, water, and brine. The organic phase was dried over $MgSO_4$, filtered, and concentrated to give 275 mg of crude product (100%) which was dissolved in 2 mL of ACN and 0.2 mL of anhydrous THF. Saturated aqueous ammonium hydroxide (2 mL) was added. The reaction was sealed and stirred for 2 d. Volatiles were removed under reduced pressure, and the residue was re-dissolved in 100 mL of EtOAc. The solution was washed successively with 30 mL each of saturated aqueous $NaHCO_3$, water, and brine. The organic phase was dried over $MgSO_4$, filtered, and concentrated. Flash chromatography of the crude product (4:1 hexanes:acetone +1% $Et_3N$) yielded 184 mg (76.5%) of the desired product.

Example 19

Preparation of Compound of Formula (3): L is CO, T is NH, $R_a$ is —$CH_2$-(2-naphthyl)

Step 1: Alkylation of 6-OH to Form Compound (4) from Illustrative Scheme 2: $R_a$ is —$CH_2$-(2-naphthyl), $R_c$ and $R_e$ are H.

Following the procedures of Example 11, steps 1–3, except substituting (2-naphthyl)methyl bromide for the allyl bromide of step 1, the compound is prepared.

Step 2: Protection of 2',4" Hydroxyls to Form Intermediate Compound (4) from Ilustrative Scheme 2: $R_a$ is —$CH_2$-(2-naphthyl), $R_c$ and $R_e$ are Acetyl.

The compound from step 1 (2.0 g) is treated according to the procedure of Example 16, step 1, except substituting acetic anhydride for the benzoic anhydride of that example.

Step 3: Formation of Intermediate Compound (9) from Illustrative Scheme 2 and Formation of Cyclic Carbamate of Compound (3) from Illustrative Scheme 2:

The compound of step 2 (500 mg) is treated with NaH and carbonyldiimidazole and is treated with ammonia in acetonitrile according to the procedure of Example 18, step 2 to afford the compound.

Example 20

Preparation of Compound of Formula (1): $R_c$ is acetyl, is CO, T is NH, $R_a$ is —$CH_2CH=CH_2$ Step 1. Preparation of Intermediate Compound (4) from Illustrative Scheme 2: $R_a$ is —$CH_2CH=CH_2$, $R_c$ and $R_e$ are acetyl.

To a sample of the compound from Example 11, step 3 or an embodiment thereof wherein $R_d$ is propyl, butyl, benzyl, vinyl or 3-hydroxybutyl (405.2 g, 528 mmol) in dichloromethane (20 mL) is added dimethylaminopyridine (0.488 g, 4 mmol) and acetic anhydride (3.39 mL, 36 mmol), and the mixture is stirred at room temperature for 3 hours. The mixture is diluted with methylene chloride, then washed with 5% aqueous sodium bicarbonate and brine and dried over $Na_2SO_4$. The residue is dried and recrystallized from acetonitrile to give the compound.

Step 2: Dehydration at C-10, 11 and Derivation of C-12 to Form Intermediate Compound (9) from Illustrative Scheme 2: $R_a$ is —$CH_2CH=CH_2$, $R_c$ and $R_e$ are Acetyl.

To a sample of the compound from step 1 (85.8 g, 100 mmol) in dry THF (500 mL) cooled to −40° C. and flushed with nitrogen is added sodium bis(trimethylsilyl)amide (125 mL, 125 mmol) over 20 minutes, and the mixture is stirred at −40° C. for 40 minutes. To this mixture is added a solution of carbonyldiimidazole (3.65 g, 22.56 mmol) in 5:3 THF/DMF (800 mL) under nitrogen at −40° C. over 30 minutes, and the mixture is stirred at −20° C. for 30 minutes. The mixture is stirred at room temperature for 27 hours, then diluted with ethyl acetate. The mixture is washed with 5% sodium bicarbonate and brine, dried over $Na_2SO_4$, and concentrated to give the compound (9), which is taken directly to the next step.

Step 3: Formation of Cyclic Carbamate of Compound (3) from Illustrative Scheme 2: $R_a$ is —$CH_2CH=CH_2$, $R_c$ and $R_e$ are Acetyl.

The compound from step 2 (124 g) is dissolved in 9:1 acetonitrile/THF (1100 mL), ammonium hydroxide (28%, 200 mL) is added, and the mixture is stirred at room temperature under nitrogen for 8 days. The solvent is removed, and the residue is dissolved in ethyl acetate. This solution is washed with 5% sodium bicarbonate and brine, dried over $Na_2SO_4$, and concentrated to give compound (3).

Step 4: Preparation of 3-OH Form of Compound (1): $R_a$ is —$CH_2CH=CH_2$, $R_c$ and $R_e$ are Acetyl.

To a sample of the compound from step 3 (69.0 g, 78.2 mmol) suspended in ethanol (200 mL) and diluted with water (400 mL) is added HCl (0.972 N, 400 mL) dropwise over 20 minutes. The mixture is stirred for 4 hours, and additional HCl is added (4 N, 100 mL) over 20 minutes. The mixture is stirred for 18 hours, cooled to 0° C., then NaOH (4 N, 200 mL) is added over 30 minutes to approximately pH 9. The intermediate compound is isolated by filtration.

Step 5: Preparation of compound (1): $R_a$ is —$CH_2CH=CH_2$, $R_c$ and $R_e$ are acetyl, L is CO, T is NH.

To a −10° C. solution under nitrogen of N-chlorosuccinimide (2.37 g, 17.8 mmol) in dichloromethane (80 mL) is added dimethylsulfide (1.52 mL, 20.8 mmol) over 5 minutes. The resulting white slurry is stirred for 10 minutes at −10° C., a solution of the compound from step 4 (8.10 g, 11.9 mmol) in dichloromethane (60 mL) is added and the reaction mixture is stirred for 30 minutes at −10 to −5° C. Triethylamine (1.99 mL, 14.3 mmol) is added dropwise over 10 minutes and the reaction mixture is stirred for 1 hour at 0° C. The reaction mixture is extracted with dichloromethane. The organic phase is washed with aqueous 5% sodium bicarbonate and brine, dried over sodium sulfate, and concentrated in vacuo to give a white foam. Chromatography on silica gel (eluting with 50:50:0.5 acetone/hexanes/ammonium hydroxide) gives the compound.

Example 21

Alternate preparation of compound of Formula (1): L is CO, T is NH, $R_a$ is —$CH_2CH=CH$-(3-quinolyl)

Step 1: Preparation of Compound of formula (1): $R_b$ is H, $R_d$ is propyl, L is CO, T is NH, $R_a$ is —$CH_2CH=CH$-(3-quinolyl)

Preparation A: Formula (1): $R_b$=H, $R_a$ is —$CH_2$—CH=CH-(3-quinolyl)

2'-O-Benzoyl-6-O-allyl-11-amino-3-descladinosyl-11-deoxy-3-oxo-15-methylerythromycin A 11,12-cyclic carbamate (40 mg, 0.0528 mmol, 1.0 eq), tris(dibenzylideneacetone) dipalladium(O)-chloroform adduct (14 mg, 0.014 mmol, 0.5 eq), tri-o-tolylphosphine (17 mg, 0.055 mmol, 1.0 eq), and 3-bromoquinoline (72 mL, 0.53 mmol, 10 eq) were placed in a round-bottom flask which was flushed with $N_2$. Degassed acetonitrile (1 mL) and freshly distilled $Et_3N$ (0.015 ml, 0.11 mmol, 2.0 eq) were added.

The reaction was refluxed for 63 h. The mixture was returned to ambient temperature and diluted with 40 mL of EtOAc. The solution was washed successively with 10 mL each of saturated aqueous $NaHCO_3$, water, and brine. The organic phase was dried over $MgSO_4$, filtered, and concentrated. Flash chromatography of the crude product (gradient from 5:1 to 2:1 hexanes:acetone+1% $Et_3N$) yielded 34 mg of the desired product.

Step 2: The above product (34 mg) was dissolved in 1 mL of methanol, sealed, and refluxed at 80° C. for 16 h. Volatiles were removed under reduced pressure. Flash chromatography (1:1 hexanes:acetone+1% $Et_3N$) gave the desired product as a light yellow solid (25 mg, 61% over two steps). ES-LC/MS: [M+H]$^+$=780.5. $^{13}$C-NMR (CDCl$_3$, 100 MHz): δ217.44, 205.37, 169.48, 157.69, 149.71, 147.61, 132.51, 129.96, 129.56, 129.15, 129.05, 128.49, 128.05, 126.70, 102.90, 83.42, 78.71, 76.42, 75.91, 70.22, 69.53, 65.83, 64.31, 58.12, 50.81, 46.29, 46.12, 45.05, 40.18 (2C), 39.05, 37.31, 31.64, 28.19, 21.15, 20.18, 19.43, 18.05, 14.38, 14.11, 13.76, 13.63 (2 C).

Preparation B: Formula (1): $R_b$=H, $R_a$ is —$CH_2$—CH=CH-(3-(6-fluoroquinolyl)

This was prepared according to the method of Preparation A using 3-bromo-6-fluoroquinoline in place of 3-bromoquinoline. ES-LC/MS: [M+H]$^+$=798.5. $^{13}$C-NMR (CDCl$_3$, 100 MHz): δ 217.49, 205.36, 169.54, 160.6 ($J_{CF}$=248 Hz), 157.68, 149.05, 144.69, 131.84, 131.64 ($J_{CF}$=9 Hz), 130.28, 129.63, 129.31, 128.7 ($J_{CF}$=10 Hz), 119.20 ($J_{CF}$=27 Hz), 110.87 ($J_{CF}$=22 Hz), 102.94, 83.42, 78.77, 76.44, 75.91, 70.22, 69.55, 65.84, 64.24, 58.09, 50.83, 46.36, 46.06, 45.05, 40.18 (2 C) 39.04, 37.32, 31.63, 28.19, 21.16, 20.19, 19.46, 18.04, 14.37, 14.18, 13.76, 13.62 (2 C).

Preparation C: Formula (1): $R_b$=H, $R_a$ is —$CH_2$—CH=CH-(3-(6-chloroquinolyl)

This is prepared according to the method of Preparation A using 3-bromo-6-chloroquinoline in place of 3-bromoquinoline. ES-LC/MS: [M+H]$^+$=814.5. $^{13}$C-NMR (CDCl$_3$, 100 MHz): δ 217.48, 205.35, 169.55, 157.67, 149.90, 145.92, 132.42, 131.49, 130.80, 130.44, 129.92, 129.49, 129.46, 128.71, 126.57, 102.94, 83.41, 78.78, 76.45, 75.91, 70.22, 69.54, 65.83, 64.23, 58.07, 50.83, 46.39, 45.99, 45.04, 40.17 (2 C), 39.03, 37.32, 31.62, 31.53, 28.18, 21.16, 20.17, 19.49, 18.04, 14.36, 14.21, 13.76, 13.61 (2 C).

Preparation D: Formula (1): $R_b$=H, $R_a$ is —$CH_2$—CH=CH-(4-isoquinolyl)

This was prepared according to the method of Preparation A using 4-bromoisoquinoline in place of 3-bromoquinoline. ES-LC/MS: [M+H]$^+$=781. $^{13}$C-NMR (CDCl$_3$, 100 MHz): δ 217.19, 205.43, 169.75, 157.39, 152.07, 140.74, 133.61, 130.65, 130.44, 128.07, 127.72, 127.05, 126.89, 122.77, 102.85, 83.28, 78.74, 75.72, 70.22, 69.51, 65.88, 64.45, 58.10, 50.91, 46.07, 45.09, 40.18 (2 C) 38.99, 37.34, 31.48, 29.66, 28.28, 21.18, 20.39, 19.33, 14.53, 14.01, 13.86, 13.66, 13.62.

Preparation E: Formula (1): $R_b$=H, $R_a$ is —$CH_2$—CH=CH-(3-pyridyl)

This was prepared according to the method of Preparation A using 3-bromopyridine in place of 3-bromoquinoline. LC/MS: [M+H]$^+$=731. $^{13}$C-NMR (CDCl$_3$, 100 MHz): δ 217.39, 205.27, 169.50, 157.61, 148.81, 148.68, 132.63, 132.16, 129.65, 128.18, 123.46, 102.91, 83.36, 78.63, 76.35, 75.79, 70.20, 69.52, 65.83, 64.17, 58.06, 50.78, 46.28, 45.03, 40.16 (2 C), 38.96, 37.29, 31.64, 31.52, 28.19, 22.58, 21.14, 20.21, 19.42, 18.04, 1.35, 14.12, 14.05, 13.79, 13.61 (2 C).

Preparation F: Formula (1): $R_b$=H, $R_a$ is —$CH_2$—CH=CH-(3-(6-methylquinolyl)

This was prepared according to the method of Preparation A using 3-bromo-6-methylquinoline in place of 3-bromoquinoline. ES-LC/MS: [M+H]$^+$=795. $^{13}$C-NMR (CDCl$_3$, 100 MHz): δ 217.37, 205.35, 169.47, 157.65, 148.82, 146.23, 136.45, 131.87, 131.37, 130.09, 129.51, 128.78, 128.22, 128.06, 126.86, 102.87, 83.40, 78.68, 75.91, 70.20, 69.47, 65.83, 64.33, 58.11, 50.81, 46.28, 45.04, 40.15 (2 C), 39.05, 37.31, 31.64, 28.24, 21.52, 21.14, 20.18, 19.45, 18.05, 14.38, 14.11, 13.77, 13.63 (2 C).

Preparation G: Formula (1): $R_b$=H, $R_a$ is —$CH_2$—CH=CH-(3-(6-aminoquinolyl)

This was prepared according to the method of Preparation A using 3-bromo-6-aminoquinoline in place of 3-bromoquinoline. ES-LC/MS: [M+H]$^+$=796.

Preparation H: Formula (1): $R_b$=H, $R_a$ is —CH$_2$—CH=CH-(3-(5-isoxazol-3-yl)thienyl)

This is prepared according to the method of Preparation A, using 5-(isoxazol-3-yl)-2-bromothiophene in place of 3-bromoquinoline.

Preparation I: Formula (1): $R_b$=H, $R_a$ is —CH$_2$—CH=CH-(6-quinolyl)

This is prepared according to the method of Preparation A, using 6-bromoquinoline in place of 3-bromoquinoline.

Preparation J: Formula (1): $R_b$=H, $R_a$ is —CH$_2$—CH=CH-(3-quinoxal-6-yl)

This is prepared according to the method of Preparation A using 6-bromoquinoxaline in place of 3-bromoquinoline.

Preparation K: Formula (1): $R_b$=H, $R_a$ is —CH$_2$—CH=CH-(5-(N-(2-pyridyl)-2-furamidyl)

This is prepared according to the method of Preparation A, using N-(2-pyridyl) 5-bromo-2-furamide in place of 3-bromoquinoline.

Preparation AA: Formula (1): $R_b$=F, $R_a$ is —CH$_2$—CH=CH-(3-quinolyl)

This was prepared according to the method of Preparation A using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate. LC/MS: [M+H]$^+$=798.6. $^{19}$F-NMR (CDCl$_3$, 376 MHz): δ −163.93. $^{13}$C-NMR (CDCl$_3$, 100 MHz): δ 217.97, 204.28 ($J_{CF}$=27 Hz), 165.62 ($J_{CF}$=23 Hz), 157.18, 149.71, 147.70, 132.65, 130.25, 129.53, 129.22, 129.12, 129.06, 128.15, 128.08, 126.78, 104.10, 98.02 ($J_{CF}$=206 Hz), 83.40, 79.59, 79.37, 77.57, 70.41, 69.74, 65.85, 64.36, 58.11, 44.23, 40.83 ($J_{CF}$=1.5 Hz), 40.25 (2 C), 39.04, 37.45, 31.37, 28.16, 25.30 ($J_{CF}$=22 Hz), 21.19, 20.86, 19.54, 17.67, 15.46 ($J_{CF}$=1.7 Hz), 13.82, 13.80, 13.29.

Preparation BB: Formula (1): $R_b$=F, $R_a$ is —CH$_2$—CH=CH-(3-(6-fluoroquinolyl)

This is prepared according to the method of Preparation B using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation CC: Formula (1): $R_b$=F, $R_a$ is —CH$_2$—CH=CH-(3-(6-chloroquinolyl)

This is prepared according to the method of Preparation C using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation DD: Formula (1): $R_b$=F, $R_a$ is —CH$_2$—CH=CH-(4-isoquinolyl)

This is prepared according to the method of Preparation D using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation EE: Formula (1): $R_b$=F, $R_a$ is —CH$_2$—CH=CH-(3-pyridyl)

This is prepared according to the method of Preparation E using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation FF: Formula (1): $R_b$=F, $R_a$ is —CH$_2$—CH=CH-(3-(6-methylquinolyl)

This is prepared according to the method of Preparation F using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation GG: Formula (1): $R_b$=F $R_a$ is —CH$_2$—CH=CH-(3-(6-aminoquinolyl)

This is prepared according to the method of Preparation G using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation HH: Formula (1): $R_b$=F, $R_a$ is —CH$_2$—CH=CH-(3-(5-isoxazol-3-yl)thienyl)

This is prepared according to the method of Preparation H using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation II: Formula (1): $R_b$=F, $R_a$ is —CH$_2$CH=CH-(6-quinolyl)

This is prepared according to the method of Preparation I using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation JJ: Formula (1): $R_b$=F, $R_a$ is —CH$_2$—CH=CH-(3-quinoxal-6-yl)

This is prepared according to the method of Preparation J using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation KK: Formula (1): $R_b$=F, $R_a$ is —CH$_2$—CH=CH-(5-(N-(2-pyridyl)-2-furamidyl)

This is prepared according to the method of Preparation K using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11- amino-3-descladinosyl-11-deoxy-3-oxo-15-methylerythromycin A 11,12-cyclic carbamate.

Using the procedures described in the preceding examples and schemes and methods known in the synthetic organic chemistry art, the cyclic carbamate compounds of Formula (1) wherein L is CO and T is NH can be prepared. These compounds having the $R_a$ substituent are described below:

—$CH_2CH=CH$-phenyl
—$CH_2CH=CH_2$
—$CH_2CH_2NH_2$,
—$CH_2CH_2CH_2OH$
—$CH_2CH_2NHCH_2$-phenyl
—$CH_2CH_2NHCH_2$-(4-quinolyl)
—$CH(C(O)OCH_3)CH_2$-phenyl
—$CH_2CH=CH$-(4-chlorophenyl)
—$CH_2CH=CH$-(4-methoxyphenyl)
—$CH_2CH=CH$-(3-quinolyl)
—$CH_2$-phenyl
—$CH_2$-(4-quinolyl)
—$CH_2CH_2CH_2$-(4-pyridyl)
—$CH_2CH_2CH_2$-(4-quinolyl)
—$CH_2CH_2CH_2$-(5-quinolyl)
—$CH_2CH=CH$-(4-benzimidazolyl)
—$CH_2$—$CH=CH$-(5-(3-isoxazolyl)-2-thiophenyl)
—$CH_2$-$CH=CH$-(5-(2-pyridyl)aminocarbonyl-2-furanyl)
—$CH_2CH=CH$-(3-quinolyl)
—$CH_2CH_2CH_3$
—$CH_2CH=NOH$.
—$CH_2F$
—$CH_2CH_2NHCH_2$-(4-pyridyl)
—$CH_2CH(OH)CN$
—$CH_2CN$
—$CH_2CH=CH$-(4-fluorophenyl)
—$CH_2CH_2CH_2$-(4-ethoxyphenyl)
—$CH_2CH_2NHCH_2CH_2$-(2-chlorophenyl)
—$CH_2$-(4-pyridyl)
—$CH_2CH=CH$-(4-pyridyl)
—$CH_2CH=CH$-(4-quinolyl)
—$CH_2CH=CH$-(5-quinolyl)
—$CH_2CH=CH$-(4-benzoxazolyl)
—$CH_2CH=CH$-(8-quinolyl)
—$CH_2$—$CH=CH$-(1,3-dimethyl-2,4-dioxo-5-pyrimidinyl)

Example 22

Preparation of compound of formula (1): L is CO, T is N($CH_3$), $R_a$ is —$CH_2CH=CH_2$, $R_c$ is H Step 1: Preparation of Compound (10) from Illustrative Scheme 3: $R_f$ is methyl, $R_a$ is —$CH_2CH=CH_2$, $R_c$ is benzoyl.

Replacing the ammonium hydroxide of Example 18 with methylamine, the above compound is formed.

Other Embodiments: Using the above procedures, compounds of formulas (1)–(3) can be formed wherein L is CO, T is: —N($CH_3$); —N$CH_2CH_2N(CH_3)_2$; —N($CH_2CH=CH_2$); —N($CH_2CH=CH$-(3-quinolyl)); or —N($NH_2$); and $R_a$ is: —$CH_2CH=CH$-(3-quinolyl); —$CH_2CH=CH_2$; —$CH_2CH_2CH_2$-(3-quinolyl); —$CH_2CH=CH$-naphthyl; —$CH_2CH=CH$-(8-chloro-3-quinolyl); —$CH_2CH=CH$-(4-chloro-2-trifluoromethyl-6-quinolyl); —$CH_2CH=CH$-(2-fluorenyl); —$CH_2CH=CH$-(3-(2-furanyl)-6-quinolyl); —$CH_2CH=CH$-(9-fluorenone-2-yl); —$CH_2CH=CH$-(6-benzoyl-2-naphthyl); —$CH_2CH=CH$-(7-methoxy-2-naphthyl); —$CH_2CH=CH$-(3-phenyl-6-quinolyl); —$CH_2CH=CH$-(3-(2-pyridyl)-6-quinolyl); —$CH_2CH=CH$-(3-(2-thiophenyl)-6-quinolyl); —$CH_2CH=CH$-(4-methylnaphthyl); —$CH_2CH=CH$-(6-β-D-galactopyranosyl-2-naphthyl); —$CH_2CH=CH$-(7-quinolyl); —$CH_2CH=CH$-(4-fluoronaphthyl); —$CH_2CH=CH$-(3-biphenyl); —$CH_2CH=CH$-(5-nitronaphthyl); —$CH_2CH=CH$-(4-pyrrolylphenyl); —$CH_2CH=CH$-(6-methoxy-2-naphthyl); —$CH_2CH=CH$-(3,5-dichlorophenyl); —$CH_2$-(3-iodophenyl); —$CH_2$-(3-(2-furanyl)phenyl); —$CH_2CH=CH$-(6-hydroxy-2-naphthyl); —$CH_2CH=CH$-(6-(2-bromoethoxy)-2-naphthyl); —$CH_2CH=CH$-(6-(2-(tetrazolyl)ethoxy-2-naphthyl); —$CH_2CH=CH$-naphthyl; —$CH_2CH=CH$-(5-(3-isoxazolyl)-2-thiophenyl); —$CH_2CH=CH$-(1,3-dimethyl-2,4-dioxo-5-pyrimidinyl); and —$CH_2CH=CH$-(5-(2-pyridyl)aminocarbonyl-2-furanyl).

Further, following the procedures of Example 21, except substituting the reagent below for the 3-bromoquinoline of Example 21, additional compounds are prepared. These are compounds of Formula (1) wherein L is CO and T is O having the $R_a$ substituent as described below:

| Reagent | $R_a$ Substituent |
| --- | --- |
| 2-bromonaphthalene | —$CH_2CH=CH$-(2-naphthyl) |
| 4-bromo-1,2-methylenedioxy-benzene | —$CH_2CH=CH$-(3,4-methylenedioxyphenyl) |
| 8-bromoquinoline | —$CH_2CH=CH$-(8-quinolyl) |
| 5-bromoindole | —$CH_2CH=CH$-(5-indolyl) |
| 3,4-ethylenedioxy-benzene | —$CH_2CH=CH$-(3,4-ethylenedioxyphenyl) |
| 1-iodo-3-nitrobenzene | —$CH_2CH=CH$-(3-nitrophenyl) |
| 3-bromo-6-nitroquinoline | —$CH_2CH=CH$-(6-nitroquinolyl) |
| 5-bromoquinoline | —$CH_2CH=CH$-(5-quinolyl) |
| 2-methyl-6-bromoquinoline | —$CH_2CH=CH$-(2-methyl-(6-quinolyl) |
| 3-bromoquinoline | *Compound of Formula (1): L is CO, T is NH, $R_c$ is acetyl; $R_a$ is —$CH_2CH=CH$-(3-quinolyl) |
| 5-bromoisoquinoline | —$CH_2CH=CH$-(5-isoquinolyl) |
| 6-bromo-7-nitro-quinoxaline | —$CH_2CH=CH$-(7-nitro-6-quinoxalinyl) |
| 3-bromo-1,8-naphthyridine | —$CH_2CH=CH$-(1,8-naphthyridin-3-yl) |
| 6-(acetylamino)-3-bromoquinoline | —$CH_2CH=CH$-(6-(acetylamino)-3-quinolyl) |
| 3-bromocarbazole | —$CH_2CH=CH$-(3-carbazolyl) |
| 5-bromobenzimidazole | —$CH_2CH=CH$-(5-benzimidazolyl) |
| 7-bromo-3-hydroxy-N-(2-methoxyphenyl)-2-napthylamide | —$CH_2CH=CH$-(-3-hydroxy-2-(N-(2-methoxyphenyl)amido)-7-naphthyl) |
| 6-bromoquinoxaline | —$CH_2CH=CH$-(6-quinoxalinyl) |
| 3-bromo-6-hydroxylquinoline | —$CH_2CH=CH$-(6-hydroxy-3-quinolyl) |
| 3-bromo-6-methoxyquinoline | —$CH_2CH=CH$-(6-methoxy-3-quinolyl) |
| 3-bromo-5-nitroquinoline | —$CH_2CH=CH$-(5-nitro-3-quinolyl) |
| 3-bromo-8-nitroquinoline | —$CH_2CH=CH$-(8-nitro-3-quinolyl) |
| 2-chloroquinoline | —$CH_2CH=CH$-(2-quinolyl) |
| 4-chloroquinoline | —$CH_2CH=CH$-(4-quinolyl) |
| 3-bromoquinoline-6-carboxylic acid | —$CH_2CH=CH$-(4-carboxyl-3-quinolyl) |
| 3-bromoquinoline-6-carboxylic acid methyl ester | —$CH_2CH=CH$-(6-methoxycarbonyl-3-quinolyl) |
| 3-bromoquinoline-6-carboxamide | —$CH_2CH=CH$-(6-aminocarbonyl-3-quinolyl) |
| 3-bromo-6-cyanoquinoline | —$CH_2CH=CH$-(6-cyano-3-quinolyl) |
| 3-bromo-6-iodoquinoline | —$CH_2CH=CH$-(3-bromo-6-quinolyl) |

*without deprotection step

Example 23

Conversion at —$OR_a$

A. Allyl→—$CH_2CHO$

The compound from Example 18 (14.0 g) is dissolved in $CH_2Cl_2$ (200 mL) and the solution is cooled to −78° C. under a nitrogen atmosphere. Ozone is then bubbled through the solution until a blue color persisted. The reaction is then purged with $N_2$ until colorless and dimethylsulfide (14 mL) is added, and the reaction mixture is warmed to 0° C. After stirring for 90 min, the reaction mixture is concentrated under reduced pressure to give a light-yellow foam. This material is dissolved in THF (300 mL) and treated with triphenylphosphine (8 g) at reflux for 6 hours, then the reaction mixture is concentrated under reduced pressure. Chromatography (1:1 acetone/hexanes to 3:1 acetone/hexanes with 0.5% TEA) gave the product.

B. —CH$_2$CHO→—CH$_2$CH$_2$NHCH$_2$Phenyl

The compound from Example 23A (120 mg, 0.187 mmol) and benzylamine (40 μL, 0.366 mmol, 2 equiv) are dissolved in 3 mL of dry dichloromethane. Molecular sieves (4 Å) are added and the reaction is stirred overnight. The reaction is then filtered and concentrated under reduced pressure. The resulting imine is dissolved in MeOH (5 mL), a catalytic amount of 10% Pd on carbon is added, and the reaction is stirred rapidly under 1 atm of H$_2$ pressure for 20 hours. The mixture is then filtered through a Celite pad, and the solution concentrated under reduced pressure. Chromatography (SiO$_2$, 5% MeOH/dichloromethane with 0.2% NH$_4$OH) gives the desired material (84 mg) as a white solid.

C. —CH$_2$CHO→—CH$_2$CH$_2$NHCH$_2$CH$_2$Phenyl

This compound is prepared from the compound of Example 23A (108 mg, 0.169 mmol) and phenethylamine (42 μL, 0.334 mmol, 2 equiv) using the procedure described for Example 23B. Chromatography (SiO$_2$, 5% MeOH/dichloromethane with 0.5% NH$_4$OH) gives the desired material.

D. —CH$_2$CHO→—CH$_2$CH$_2$NHCH$_2$CH$_2$CH$_2$Phenyl

This compound is prepared from the compound of Example 23A (100 mg, 0.156 mmol) and 3-phenyl-1-propylamine (40 μL, 0.282 mmol, 1.8 equiv) using the procedure described for Example 23B. Chromatography (SiO$_2$, 5% MeOH/dichloromethane with 0.5% NH$_4$OH) gives the desired material.

E. —CH$_2$CHO→—CH$_2$CH$_2$NHCH$_2$CH$_2$CH$_2$Phenyl

This compound is prepared from the compound of Example 23A (170 mg, 0.266 mmol) and 4-phenyl-1-butylamine (68 μL, 0.431 mmol, 1.6 equiv) using the procedure described for Example 23B. Chromatography (SiO$_2$, 5% MeOH/dichloromethane with 0.2% NH$_4$OH) gives the desired material.

F. —CH$_2$CHO→—CH$_2$CH$_2$NHCH$_2$CH$_2$-(3-quinolyl)

The compound from Example 23A (135 mg, 0.211 mmol) and 3-(3-quinolyl)-1-propylamine (70 mg, 0.376 mmol, 1.8 equiv) are dissolved in 4 mL of dry dichloromethane. Molecular sieves (4A) are added and the reaction is stirred overnight. The reaction is then filtered and concentrated under reduced pressure. The resulting imine is dissolved in MeOH (5 mL) and treated with NaCNBH$_3$ (about 100 mg) and enough AcOH to turn bromocresol green indicator from blue to yellow. After stirring for 4 hours, the reaction mixture is poured into saturated NaHCO$_3$ solution and extracted into dichloromethane. The organic portion is washed with saturated NaHCO$_3$, H$_2$O and brine, dried (Na$_2$SO$_4$) and concentrated under reduced pressure. Chromatography (SiO$_2$, 5% MeOH/dichloromethane with 0.5% NH$_{40}$H to 10% MeOH/dichloromethane with 1% NH$_4$OH) gives the desired material.

G. —CH$_2$CHO→—CH$_2$CH$_2$NHCH$_2$(3-quinolyl)

The title compound is prepared from the compound of Example 23A (150 mg, 0.234 mmol) and 3-(aminomethyl)quinoline (100 mg, 0.633 mmol, 2.7 equiv) using the procedure described for Example 23F. Chromatography (SiO$_2$, 5% MeOH/dichloromethane with 0.5% NH$_4$OH) gives the desired material The 3-(aminomethyl)quinoline reagent is prepared by methods known in the art.

Other embodiments of the formulas (1)–(3) wherein R$_b$ is H, R$_c$ is H, L is —CO—, T is —NH—, and R$_d$ is propyl, butyl, benzyl, vinyl, or 3-hydroxy butyl are those wherein R$_a$ is converted from —CH$_2$CHO to: —CH$_2$CH$_2$NHCH$_2$(6-quinolyl); —CH$_2$CH=NO(phenyl); —CH$_2$CH=NOCH$_2$(phenyl); —CH$_2$CH=NOCH$_2$(4-NO$_2$-phenyl); —CH$_2$CH=NOCH$_2$(4-quinolyl); —CH$_2$CH=NOCH$_2$(2-quinolyl); —CH$_2$CH=NOCH$_2$(3-quinolyl); —CH$_2$CH=NOCH$_2$(6-quinolyl); —CH$_2$CH=NOCH$_2$(1-naphthyl); —CH$_2$CH=NOCH$_2$(2-naphthyl); —CH$_2$CH$_2$NHOCH$_2$(phenyl); —CH$_2$CH$_2$NHOCH$_2$(4-NO$_2$-phenyl); —CH$_2$C(O)-phenyl; —CH$_2$C(O)-(4-F-phenyl); —CH$_2$CH=NNHC(O)phenyl; or —CH$_2$CH(OH)-phenyl.

H. —CH$_2$CH=CH-(3-quinolyl) —CH$_2$CH$_2$CH$_2$(3-quinolyl)

A mixture of the compound from Example 18 where R$_a$ is —CH$_2$CH=CH-(3-quinolyl) (230 mg) and 10% Pd/C (50 mg) in 30 mL of methanol and 15 mL of ethyl acetate is flushed with nitrogen and stirred under 1 atm of hydrogen at room temperature for 22 hours. The mixture is filtered, and the filtrate is concentrated under reduced pressure. Chromatography on silica gel (5% MeOH/dichloromethane with 0.5% NH$_4$OH) gives the desired material.

I. —CH$_2$CH=CH-(3-quinolyl)→—CH$_2$(2-(3-quinolyl) cyclopropyl)

To a solution of diazomethane (0.64 M, 3.12 mL, 2.00 mmol) in ether is added a solution of the compound from Example 18 wherein R$_a$ is —CH$_2$CH=CH-(3-quinolyl) (153 mg, 0.200 mmol) in dichloromethane (5.0 mL) at 0° C. under nitrogen. A small amount (2 mg) of palladium acetate is added, and the mixture is stirred for 20 minutes. Another portion of diazomethane (3 mL) is added, and the mixture is stirred for another hour. The solvents are evaporated, and the residue is purified by chromatography on silica gel (5% MeOH/dichloromethane with 0.5% NH$_4$OH) to give the title compound as a white solid.

Example 24

Conversions at R$_c$

A. —H→propanoyl (R$_a$ is —CH$_2$CH=CH-(3-quinolyl))

To a solution of the compound from Example 18 converted at R$_a$, wherein R$_a$ is —CH$_2$CH=CH(3-quinolyl), (152 mg) in dichloromethane is added propionic anhydride (52 μL) and triethylamine (56 μL), and the mixture is stirred for 24 hours at room temperature. The mixture is diluted with ethyl acetate, and this is washed with 5% NaHCO$_3$ solution and brine, dried (Na$_2$SO$_4$) and concentrated under reduced pressure. The residue is chromatographed on silica gel (1:1 acetone/hexanes) to give the title compound as a white foam.

B. —H→ethylsuccinoyl (R$_a$ is —CH$_2$CH=CH-(3-quinolyl))

To a solution of the compound from Example 18 converted at R$_a$, wherein R$_a$ is —CH$_2$CH=CH-(3-quinolyl) (153 mg, 0.200 mmol) in dichloromethane (10 mL) at 0° C. is added ethyl succinyl chloride (29 μL) and triethylamine (56 μL), and the mixture is stirred for 24 hours at room temperature. The mixture is diluted with ethyl acetate, and this is washed with 5% NaHCO$_3$ solution and brine, dried (Na$_2$SO$_4$) and concentrated under reduced pressure. The residue is chromatographed on silica gel (1:1 acetone/hexanes) to give the title compound as a white foam.

Example 25

Preparation of Compound of Formula (1): L is CO, T is NH, R$_a$ is —CH$_2$C=C—H, R$_c$ and R$_e$ are H Step 1: Preparation of Intermediate of Compound (4): Position 9 is N—O—(1-isopropoxycyclohexyl), R$_a$ is —CH$_2$C≡C—H, R$_c$ and R$_e$ are trimethylsilyl.

To a solution under nitrogen of 2',4"-bis-O-trimethylsilylerythromycin A 9-[O-(1-isopropoxycyclohexyl)]oxime (100 g, 96.9 mmol, prepared according to the method of U.S. Pat. No. 4,990,602) in THF (200 mL) is added anhydrous DMSO (200 mL) and the mixture is cooled to 0° C. To this solution stirred under a $N_2$ atmosphere is added propargyl bromide (27 mL, 240 mmol, 80 wt. % in toluene), followed by a solution of dry KOH (13.6 g, 240 mmol) in anhydrous DMSO (300 mL) over 25 minutes, and the mixture is stirred vigorously for 1 hour at 0° C. Additional KOH (10.9 g, 190 mmol) and propargyl bromide (21 mL, 190 mmol) is added, and the mixture is stirred at 0° C. under $N_2$ for 1.5 hours. This addition of KOH and propargyl bromide is repeated 3 more times at 1.5 hour intervals. The mixture is then extracted with ethyl acetate, and the organic phases are washed with water and brine and dried ($MgSO_4$). Removal of the solvent under vacuum gives the crude product, which is taken directly to the next step.

Step 2: Conversion of —N—O- (1-isopropoxycyclohexyl) at Position 9 to —NOH in Intermediate of Compound (4): $R_a$ is, —$CH_2C\equiv C$—H.

To the compound from Step 1 (108 g) in $CH_3CN$ (300 mL) is added water (150 mL) and acetic acid (glacial, 200 mL), and the mixture is stirred at room temperature for about 20 hours. The solvent is then removed under vacuum at 40° C., and the residue is taken up in EtOAc and washed successively with 5% $Na_2CO_3$ and brine. The organic phase is then dried over $MgSO_4$, filtered and concentrated to give the compound as a brown foam, which is taken directly to the next step.

Step 3: Conversion of —NOH at Position 9 to =O to Form Intermediate Compound (4): $R_a$ is —$CH_2C\equiv C$—H.

The compound from Step 2 (74 g) is dissolved in ethanol (550 mL) and diluted with water (550 mL). To this solution is added sodium nitrite (33 g, 0.48 mol), and the reaction mixture is stirred at room temperature for 15 minutes. Next is added 4M HCl (125 mL, 0.48 mol) at ambient temperature over 15 minutes, the mixture is heated to 70° C. for two hours, then cooled to room temperature. The mixture is extracted with ethyl acetate, and the organic phase is washed with 5% $Na_2CO_3$ and brine, then dried over $MgSO_4$, filtered and concentrated. The crude product is purified by chromatography on silica gel, eluting with 1% methanol/dichloromethane containing 0.5% ammonium hydroxide. The compound is crystallized from acetonitrile to give the compound.

Step 4: Protection of 2' and 4" Hydroxyl Groups to Form Intermediate Compound (4) from Illustrative Scheme 2: $R_c$ and $R_e$ are Acetyl, $R_a$ is —$CH_2C\equiv C$—H.

To a solution of 19 grams (246 mmol) the compound from Step 3 in anhydrous dichloromethane (100 mL) is added 4-dimethylaminopyridine (105 mg) and triethylamine (7.16 mL, 52 mmol). The mixture is cooled to about 15° C. in a cold water bath, and acetic anhydride (5.5 mL, 59 mmol) is added over 5 minutes. After stirring at 15° C. for 5 minutes, the cold water bath is removed, and the reaction is stirred at ambient temperature for 4 hours. The mixture is diluted with ethyl acetate and washed successively with 5% aqueous sodium carbonate (twice), water (twice) and brine. The organic extracts are dried over magnesium sulfate, filtered and concentrated in vacuo. Drying to constant weight with high vacuum provided the compound.

Step 5: Dehydration at Position 10, 11 and Derivation at Position 12 to Form Intermediate Compound (9) from Illustrative Scheme 2: $R_c$ and $R_e$ are acetyl, $R_a$ is —$CH_2C\equiv C$—H.

To a 0° C. solution of the compound from Step 4 (21 g, 24.5 mmol) in THF (128 mL) and dimethyl sulfoxide (48 mL) is added 1,1'-carbonyldiimidazole (14.3 g, 88.3 mmol). After stirring for 5 minutes, sodium hydride (60% dispersion in mineral oil, 1.3 g, 32.5 mmol) is added portionwise over 1 hour under a nitrogen atmosphere. After complete addition, the cooling bath is removed, and the mixture is stirred at ambient temperature for 3.5 hours. The reaction is recooled to 0° C., diluted with ethyl acetate (400 mL), and quenched with 5% aqueous sodium bicarbonate (50 mL). The organic layers are washed successively with water and brine, then dried over magnesium sulfate. The solution is filtered and the filtrate is concentrated in vacuo and dried to constant weight to afford the compound which is taken directly to the next step.

Step 6: Form Cyclic Carbamate of Compound (3) from Illustrative Scheme 2: $R_c$ and $R_e$ are Acetyl, $R_a$ is —$CH_2C\equiv C$—H.

A pressure vessel containing the compound from Step 5 (23 g, 24 mmol) in acetonitrile (250 mL) is cooled to −78° C. An equal volume of liquid ammonia (250 mL) is condensed into the reaction vessel which is then sealed and allowed to warm to ambient temperature with stirring. After 20 hours the reaction is recooled to −78° C., the pressure vessel is opened and the reaction was allowed to warm to ambient temperature with stirring. When all the liquid ammonia had evaporated, the acetonitrile is removed in vacuo, and the residue is dried to constant weight to provide the compound.

Step 7: Remove Position 3 Cladinose Moiety to Form Compound (1) Having a Position 3 Hydroxyl Group: $R_c$ is acetyl, $R_a$ is —$CH_2C\equiv C$—H.

To a 0° C. suspension of the compound from Step 6 (21 g) in 1:1 ethanol/water (200 mL) is added 4 M hydrochloric acid (125 mL) over 10 minutes. After removing the cooling bath, the reaction solution is stirred at ambient temperature for 26 hours. The mixture is diluted with water, cooled to 0° C. and made basic to pH 10 with 2N sodium hydroxide. The mixture is then extracted with ethyl acetate (400 mL), and the organic layers are washed with brine. The organic extracts are dried over magnesium sulfate, filtered, and concentrated in vacuo. Drying to constant weight provided 18 g of the crude product which is crystallized from ethyl acetate/hexanes to give the pure compound.

Step 8: Oxidation of Position 3 Hydroxyl to Carbonyl of Compound (1): $R_c$ acetyl, $R_a$ is —$CH_2C\equiv C$—H.

To a −10° C. solution of N-chlorosuccinimide (2.3 g, 0.017 moles) in dichloromethane (100 mL) is added methyl sulfide (1.47 mL, 0.021 moles) over 5 minutes. The reaction is stirred at −10° C. for 10 minutes. A solution of the compound from Step 7 (8.3 g, 0.012 m) in dichloromethane (100 mL) is then added over 30 minutes, and the mixture is stirred for 25 minutes at −10° C. Triethylamine (1.6 mL, 0.021 mol) is added over 5 minutes, and the reaction is stirred at −10° C. for 50 minutes. The reaction is then quenched with 5% aqueous sodium bicarbonate (50 mL), and extracted with dichloromethane (300 mL). The organic layers are washed with 5% aqueous sodium bicarbonate followed by brine, dried over magnesium sulfate, filtered, and concentrated in vacuo. The crude product is purified on silica gel with column chromatography eluting sequentially with 30% acetone/hexanes followed by 50% acetone/hexanes to provide the compound.

Step 9: Deprotection to Form Compound of Formula (1): L is CO, T is NH, $R_a$ is —$CH_2C\equiv C$—H, $R_c$ is H.

A sample (72 mg) of the compound from Step 8 is dissolved in methanol (8 mL) and stirred at ambient temperature for 18 hours. After concentrating under vacuum and drying to constant weight under high vacuum 65 mg of the pure title compound is obtained.

Optional Step: Conversion of $R_a$ from —$CH_2C\equiv C$-(6-methoxy-2-naphthyl bromonaphthalene) to —$CH_2C\equiv C$—Br to form compound (1): $R_a$ is —$CH_2C\equiv C$—Br, $R_c$ is cetyl.

To a solution under nitrogen of the compound of Example 25, Step 8 (100 mg) in acetone (1 mL) is added acetic acid (8.4 μL) at ambient temperature. A second solution containing N-bromosuccinimide (39 mg) and silver nitrate (2.5 mg) in 1 mL of acetone is prepared and then stirred at room temperature under nitrogen for ten minutes and is cooled to 0° C. The first solution is then added to the second solution in one portion, the cooling bath is removed, and the resulting reaction mixture stirred at room temperature under nitrogen for 2 hours. The reaction is then diluted with ethyl acetate, saturated aqueous sodium bicarbonate is added, and the mixture is stirred at room temperature overnight. The organic phase is separated, washed with brine and dried ($MgSO_4$). The solvent is removed, and the residue is purified by chromatography on silica gel, eluting with 40% acetone/hexanes to give the compound. The $R_c$ group can be deprotected with methanol.

Example 26

Preparation of Compound of Formula (1): L is CO, T is NH, $R_a$ is specified below, $R_c$ is H, $R_b$ is H, $R_d$ is propyl I. Starting Material: Preparation of Compound of Formula (1): $R_b$=H, $R_a$ is —O-propargyl Step 1: A solution of 2',4"-bis-O-trimethylsilyl-15-methylerythromycin A 9-[O-(1-isopropoxycyclohexyl)] oxime (100 mg) in 0.1 mL of tetrahydrofuran, 0.1 mL of ether, and 0.1 mL of DMSO was cooled to 10° C. and treated with 0.028 mL of 3-bromo-1-(trimethylsilyl)-1-propyne under inert atmosphere. A mixture of methylsulfoxide (0.19 mL) and 1.0 M potassium tert-butoxide in tetrahydrofuran (0.38 mL) was added at a rate of 2.0 molar equivalents of base per hour. Additional equivalents (0.014 mL) of the TMS-propargyl bromide were added after 0.5 and 1 hours. The reaction was monitored by thin-layer chromatography (silica gel, 10:1 toluene/acetone), and was judged complete after addition of 2.3 molar equivalents of base. The reaction was diluted with 100 mL of ethyl acetate and 30 mL of saturated $NaHCO_3$, and washed sequentially with saturated $NaHCO_3$, water, and brine. The organic phase was dried with $MgSO_4$, filtered, and evaporated. The crude product was chromatographed on silica gel (40:1 hexanes/acetone +1% $Et_3N$) to yield partially purified 6-O-(3-trimethylsilyl) propargyl-2',4"-bis-O-trimethylsilyl-15-methylerythromycin A 9-[O-(1-isopropoxycyclohexyl)] oxime.

Step 2: A solution of the impure 6-O-(3-trimethylsilyl) propargyl-2',4"-bis-O-trimethylsilyl-15-methylerythromycin A 9-[O-(1-isopropoxycyclohexyl)] oxime from above (0.88 g) in 4.4 mL of acetonitrile is treated with 2.2 mL of water and 2.5 mL of acetic acid, and stirred for 24 hours at ambient temperature. The mixture is concentrated after addition of 2-propanol, then repeatedly after addition of toluene. This material is stirred with potassium carbonate and methanol (6 mL) for 2.5 hours. The mixture is diluted with ethyl acetate (200 mL), and washed sequentially with saturated $NaHCO_3$, water, and brine. The organic phase is dried with $MgSO_4$, filtered, and evaporated to yield the product.

Step 3: A solution of the product from (iii) and sodium hydrosulfite (0.59 g) in 7 mL of 1:1 ethanol/water is placed under inert atmosphere. Formic acid (0.096 mL) is added dropwise, and the mixture is stirred at 80° C. for 5 hours. After cooling to ambient temperature, the reaction is adjusted to pH 10 with 6 N NaOH and extracted three times with 150-mL portions of ethyl acetate. The organic extracts are combined and washed sequentially with saturated $NaHCO_3$, water, and brine. The organic phase is dried with $MgSO_4$, filtered, and evaporated to yield 6-O-propargyl-15-methylerythromycin A suitable for further conversion. Pure material can be prepared by chromatography on silica gel.

Step 4: A mixture of 6-O-propargyl-15-methylerythromycin A (0.40 g) and 6 mL of 0.6 N HCl is stirred at ambient temperature for 17 hours. The pH is adjusted to 9 by addition of 6 N NaOH, and 150 mL of ethyl acetate is added. The organic extracts are washed sequentially with saturated $NaHCO_3$, water, and brine, then dried over $MgSO_4$, filtered, and evaporated to provide further product. The crude product is chromatographed on silica gel to give pure 6-O-propargyl-3-descladinosyl-15-methylerythromycin A.

Step 5: A solution of 6-O-propargyl-3-descladinosyl-15-methylerythromycin A (0.16 g) and benzoic anhydride (0.12 g) in 1.3 mL of ethyl acetate is stirred for 17 h, then washed sequentially with saturated $NaHCO_3$, water, and brine. The solution is dried over $MgSO_4$, filtered, and evaporated. The crude product is chromatographed on silica gel to yield 2'-O-benzoyl-6-O-propargyl-3-descladinosyl-15-methylerythromycin A.

Step 6: N-Chlorosuccinimide (0.510 g, 3.82 mmol, 1.50 eq) is dissolved in 13 mL of anhydrous $CH_2Cl_2$ and cooled to −10° C. under N2. Methyl sulfide (0.328 mL, 4.46 mmol, 1.75 eq) is added, and the reaction is stirred for 15 min. A solution of 2'-O-benzoyl-6-O-propargyl-3-descladinosyl-15-methylerythromycin A (1.87 g, 2.55 mmol, 1.00 eq) in 13 mL of anhydrous $CH_2Cl_2$ is added dropwise. After 30 min, freshly distilled $Et_3N$ (0.355 mL, 2.55 mmol, 1.00 eq) is added, and the reaction is brought up to 0° C. over 30 min. The reaction mixture is diluted with 400 mL EtOAc and washed successively with 100 mL each of saturated aqueous $NaHCO_3$, water, and brine. The organic layer is dried over $MgSO_4$, filtered, concentrated, and purified by chromatography.

Step 7: 2'-O-Benzoyl-6-O-propargyl-3-descladinosyl-3-oxo-15-methylerythromycin A (904 mg) is dissolved in freshly distilled pyridine (4 mL) and cooled to 0° C. Methanesulfonyl chloride (0.478 mL, 6.17 mmol, 5.00 eq) is added dropwise. The reaction is allowed to come to ambient temperature and stirred overnight. The mixture is diluted with 350 mL of EtOAc and quenched with 100 mL of saturated aqueous $NaHCO_3$. The layers are separated, and the organic phase is washed successively with 100 mL each of water and brine. The organic phase is dried over $MgSO_4$, filtered, and concentrated. Flash chromatography over silica gel yields the product.

Step 8: 2'-O-Benzoyl-6-O-propargyl-3-descladinosyl-3-oxo-11-methanesulfonyl-15-methyl-erythromycin A (705 mg) is dissolved in acetone (3 mL), and 1,8-diazabicyclo[5.4.0]-undec-7-ene (0.651 mL, 4.35 mmol, 5.00 eq) is added dropwise. The reaction is stirred at ambient temperature for 6 h and then concentrated. Flash chromatography over silica gel yields the product.

Step 9: 2'-O-Benzoyl-6-O-propargyl-10,11-anhydro-3-descladinosyl-3-oxo-15-methylerythromycin A (227 mg) is dissolved in 1.3 mL of freshly distilled THF and cooled to −15° C. under $N_2$. Sodium hydride (25 mg of a 60% dispersion in mineral oil, 0.634 mmol, 2.00 eq) is added, and the reaction was stirred for 15 min. A solution of 1,1-carbonyldiimidazole (140 mg) in 1.3 mL of freshly distilled THF is added dropwise. After stirring for 30 min, the reaction is allowed to warm to ambient temperature over 1.5 h. The mixture is diluted with 100 mL of EtOAc and washed successively with 30 mL each of saturated aqueous NaHCO$_3$, water, and brine. The organic phase is dried over MgSO$_4$, filtered, and concentrated, then the residue is dissolved in 2 mL of ACN and 0.2 mL of anhydrous THF. Saturated aqueous ammonium hydroxide (2 mL) is added. The reaction is sealed and stirred for 2 days. Volatiles are removed under reduced pressure, and the residue is redissolved in 100 mL of EtOAc. The solution is washed successively with 30 mL each of saturated aqueous NaHCO$_3$, water, and brine. The organic phase is dried over MgSO$_4$, filtered, and concentrated. Flash chromatography yields the cyclic carbamate product.

II. Preparation of Compounds using Compounds of I

Preparation A: Formula (1): $R_b$=H, $R_a$ is —CH$_2$—CC-(3-quinolyl)

Step 1: 2'-O-Benzoyl-6-O-propargyl-11-amino-3-descladinosyl-11-deoxy-3-oxo-15-methylerythromycin A 11,12-cyclic carbamate (40 mg), tris(dibenzylideneacetone) dipalladium(0)-chloroform adduct (14 mg), tri-o-tolylphosphine (17 mg), copper iodide, and 3-bromoquinoline (72 µl, 0.53 mmol, 10 eq) are placed in a round-bottom flask which is flushed with N$_2$. Degassed acetonitrile (1 mL) and freshly distilled Et$_3$N (0.015 ml, 0.11 mmol, 2.0 eq) are added. The reaction is refluxed for 63 h. The mixture is returned to ambient temperature and diluted with 40 mL of EtOAc. The solution is washed successively with 10 mL each of saturated aqueous NaHCO$_3$, water, and brine. The organic phase is dried over MgSO$_4$, filtered, and concentrated. Flash chromatography yields the desired product.

Step 2: The above product is dissolved in 1 mL of methanol, sealed, and refluxed at 80° C. for 16 h. Volatiles are removed under reduced pressure. Flash chromatography yields the desired product.

Preparation B: Formula (1): $R_b$=H, $R_a$ is —CH$_2$—CC-(3-(6-fluoroquinolyl)

This is prepared according to the method of Preparation A, using 3-bromo-6-fluoroquinoline in place of 3-bromoquinoline.

Preparation C: Formula (1): $R_b$=H, $R_a$ is —CH$_2$—CC-(3-(6-chloroquinolyl)

This is prepared according to the method of Preparation A, using 3-bromo-6-chloroquinoline in place of 3-bromoquinoline.

Preparation D: Formula (1): $R_b$=H, $R_a$ is —CH$_2$—CC-(4-isoquinolyl)

This is prepared according to the method of Preparation A, using 4-bromoisoquinoline in place of 3-bromoquinoline.

Preparation E: Formula (1): $R_b$=H, $R_a$ is —CH$_2$—CC-(3-pyridyl)

This is prepared according to the method of Preparation A, using 3-pyridine in place of 3-bromoquinoline.

Preparation F: Formula (1): $R_b$=H, $R_a$ is —CH$_2$—CC-(3-(6-methylquinolyl)

This is prepared according to the method of Preparation A, using 3-bromo-6-methylquinoline in place of 3-bromoquinoline.

Preparation G: Formula (1): $R_b$=H, $R_a$ is —CH$_2$—CC-(3-(6-aminoquinolyl)

This is prepared according to the method of Preparation A, using 3-bromo-6-aminoquinoline in place of 3-bromoquinoline.

Preparation H: Formula (1): $R_b$=H, $R_a$ is —CH$_2$—CC-(3-(5-isoxazol-3-yl)thienyl)

This is prepared according to the method of Preparation A, using 5-(isoxazol-3-yl)-2-bromothiophene in place of 3-bromoquinoline.

Preparation I: Formula (1): $R_b$=H, $R_a$ is —CH$_2$—CC-(6-quinolyl)

This is prepared according to the method of Preparation A, using 6-bromoquinoline in place of 3-bromoquinoline.

Preparation J: Formula (1): $R_b$=H, $R_a$ is —CH$_2$—CC-(3-quinoxal-6-yl)

This is prepared according to the method of Preparation A using 6-bromoquinoxaline in place of 3-bromoquinoline.

Preparation K: Formula (1): $R_b$=H, $R_a$ is —CH$_2$—CC-(5-(N-(2-pyridyl)-2-furamidyl)

This is prepared according to the method of Preparation A, using N-(2-pyridyl) 5-bromo-2-furamide in place of 3-bromoquinoline.

Preparation AA: Formula (1): $R_b$=F, $R_a$ is —CH$_2$—CC-(3-quinolyl)

This was prepared according to the method of Preparation A using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation BB: Formula (1): $R_b$=F, $R_a$ is —CH$_2$—CC-(3-(6-fluoroquinolyl)

This is prepared according to the method of Preparation B using 2'-O-benzoyl-6-O-allyl-11-amino-3-descladinosyl-11-deoxy-3-oxo-2-fluoro-15-methyletythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation CC: Formula (1): $R_b$=F, $R_a$ is —CH$_2$—CC-(3-(6-chloroquinolyl)

This is prepared according to the method of Preparation C using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation DD: Formula (1): $R_b$=F, $R_a$ is —CH$_2$—CC-(4-isoquinolyl)

This is prepared according to the method of Preparation D using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation EE: Formula (1): $R_b$=F, $R_a$ is —CH$_2$—CC-(3-pyridyl)

This is prepared according to the method of Preparation E using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation FF: Formula (1): Rb=F, $R_a$ is —CH$_2$—CC-(3-(6-methylquinolyl)

This is prepared according to the method of Preparation F using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation GG: Formula (1): $R_b$=F, $R_a$ is —CH$_2$—CC-(3-(6-aminoquinolyl)

This is prepared according to the method of Preparation G using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11- amino-3-descladinosyl-11-deoxy-3-oxo-15-methylerythromycin A 11,12-cyclic carbamate.

Preparation HH: Formula (1): $R_b$=F, $R_a$ is —$CH_2$—CC-(3-(5-isoxazol-3-yl thienyl)

This is prepared according to the method of Preparation H using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation II: Formula (1): $R_b$=F, $R_a$ is —$CH_2$—CC-(6-quinolyl)

This is prepared according to the method of Preparation I using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation JJ: Formula (1): $R_b$=F, $R_a$ is —$CH_2$—CC-(3-quinoxal-6-yl)

This is prepared according to the method of Preparation J using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation KK: Formula (1): $R_b$=F, $R_a$ is —$CH_2$—CC-(5-(N-(2-pyridyl)-2-furamidyl)

This is prepared according to the method of Preparation K using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Example 27

Compound of Formula (1): L is CO, T is NH, $R_a$ is —$CH_2$-(2,2-dimethyl-1,3-dioxolan-4-yl), $R_c$ is H Step 1: Conversion of 3-OH Form of Compound (1) From $R_a$ is —$CH_2CH=CH_2$ to $R_a$ is —$CH_2CH(OH)CH_2OH$, $R_c$ is Acetyl.

To a sample of the compound from Example 20, Step 4 (5.0 g, 7.32 mmol, 3-OH form of compound (1), $R_a$ is —$CH_2CH=CH_2$, $R_c$ is acetyl) and N-methylmorpholine N oxide (1.7 g, 14.5 mmol) in THF (25 mL) at room temperature is added OsO (4% in $H_2O$, 0.090 mL, 0.0147 mmol), and the mixture is stirred for 24 hours. The reaction is quenched with sodium bisulfite (1.5 g) and water (10 mL), and the solvents are removed under vacuum. The residue is dissolved in ethyl acetate, which is washed with saturated aqueous sodium bicarbonate, water and brine, and dried ($Na_2SO_4$). The solvent is removed to give the compound.

Step 2: Conversion of 3-OH Form of Compound (1) From $R_a$ is —$CH_2CH(OH)CH_2OH$ to $R_a$ is —$CH_2$-(2,2-dimethyl-1,3-dioxolan-4-yl), $R_c$ is Acetyl.

To a sample of the compound from Step 1 (500 mg, 0.70 mmol) and 2,2-dimethoxypropane (0.26 mL, 2.1 mmol) in toluene (7 mL) is added p-toluenesulfonic acid (160 mg, 0.84 mmol), and the mixture is stirred at 55° C. for 3 days. The mixture is diluted with ethyl acetate, and this solution is washed with 10% sodium carbonate solution, water and brine. The organic phase is dried ($Na_2SO_4$), and the solvent is removed to give the crude product, which is purified by chromatography on silica gel, eluting with 2:97:1 methanol/chloroform/ammonium hydroxide to give the compound.

Step 3: Oxidation of 3-OH to Carbonyl to Form Compound (1): $R_a$ is —$CH_2$-(2,2-dimethyl-1,3-dioxolan-4-yl), $R_c$ is Acetyl.

A sample of the compound from Step 2 (356 mg, 0.47 mmol) is oxidized with N-chlorosuccinimide and dimethylsulfide according to the procedure of Example 16, Step 2, to afford the compound.

Step 4: Deprotection to Form Compound of Formula (1): L is CO, T is NH, $R_a$ is —$CH_2$(2,2-dimethyl-1,3-dioxolan-4-yl), $R_c$ is H.

A sample of the compound from Step 3 (100 mg, 0.13 mmol) is stirred in methanol (4 mL) overnight at room temperature. The solvent is removed, and the residue is purified by chromatography on silica gel, eluting with 0.9:98:1 methanol/chloroform/ammonium hydroxide to give the compound.

Optional Step: Conversion of $R_a$ is —$CH_2$-(2,2-dimethyl-1,3-dioxolan-4-yl) in compound (1) to —$CH_2CH(OH)CH_2OH$.

A sample of the compound from Step 4 (100 mg, 0.13 mmol) is stirred at reflux with p-toluenesulfonic acid (35 mg, 0.18 mmol) in 4:1 THF/water (2.5 mL) for 3 hours. The mixture is diluted with ethyl acetate, and this solution is washed with 10% sodium carbonate solution, water and brine. The organic phase is dried ($Na_2SO_4$), and the solvent is removed to give the crude product, which is purified by chromatography on silica gel, eluting with 2:97:1 methanol/chloroform/ammonium hydroxide to give the compound.

Example 28

Fluorination of C2 Position before 11,12 Cyclic Ring Formed Synthesis of 2'-O-benzoyl-6-O-propargyl-3-descladinosyl-3-oxo-10,11-anhydro-2-fluoro-15-methylerythromycin A A solution of 2'-O-benzoyl-6-O-propargyl-3-descladinosyl-3-oxo-10,11-anhydro-15-methyl-erythromycin A in tetrahydrofuran under inert atmosphere is cooled to −78° C. and treated with 1.0 M potassium tert-butoxide in tetrahydrofuran. The mixture is stirred for 5 minutes, and a solution of N-fluorobenzenesulfonimide in tetrahydrofuran is added in three portions over 2 hours. After addition, the reaction is allowed to warm to ambient temperature and kept for an additional 5 hours. Aqueous $K_2CO_3$ is added, and the mixture is extracted with $CH_2Cl_2$. The organic extracts are combined, dried over $MgSO_4$, filtered, and evaporated. Chromatography on silica gel gives the product.

Example 29

Fluorination of C2 Position after Cyclic Carbamate Formed Synthesis of 2'-O-benzoyl-6-O-allyl-3-descladinosyl-3-oxo-11-deoxy-11-amino-2-fluoro-15-methylerythromycin A 11,12 cyclic carbamate To a THF solution (0.5 ml) of 2'-O-benzoyl-6-O-allyl-3-descladinosyl-3-oxo-11-deoxy-11-amino-15-methylerythromycin A 11,12-cyclic carbamate (100 mg, 0.132 mmol, 1.0 eq) was added a THF solution of potassium tert-butoxide (0.3 ml, 1M, 2.3 eq.) at −78° C. The reaction mixture was then kept at −60° C. to −40° C. for 20 min., followed by introduction of N-Fluorobenzenesulfonimide (46 mg, 0.146 mmol, 1.1 eq.) in THF (0.2 ml) at −78° C. The reaction mixture was kept at −70° C. to −40° C. for 1 h before it was allowed to warm to 0° C. from −70° C. in 1.5 h. It was then diluted with EtOAc, washed with saturated aqueous $NaHCO_3$, water, and brine. The organic phase was dried over $MgSO_4$, filtered, and concentrated. Flash chromatography of the crude product (4:1 hexanes:acetone +1% $Et_3N$) yielded 76 mg (74%) of the desired product. $^{13}$C-

NMR (100.6 MHz, CDCl$_3$) δ 217.5, 203 (d, J=27.6 Hz), 165.5 (d, J=23.8 Hz), 165.2, 157.5, 135.4, 132.9, 130.4, 129.8, 128.3, 118.0, 101.7, 98 (d, J=207 Hz), 83.5, 79.1, 78.6, 72.1, 69.4, 64.6, 63.5, 57.5, 44.2, 40.7, 40.4, 38.5, 37.3, 31.4, 31.3, 24.9 (d, J=24.3 Hz), 21.0, 20.7, 19.4, 17.7, 15.0, 13.9, 13.7, 13.3.

Example 30

Derivatization of C-13 Position Starting Material: 15-Aminoerythromycin A diacetate salt

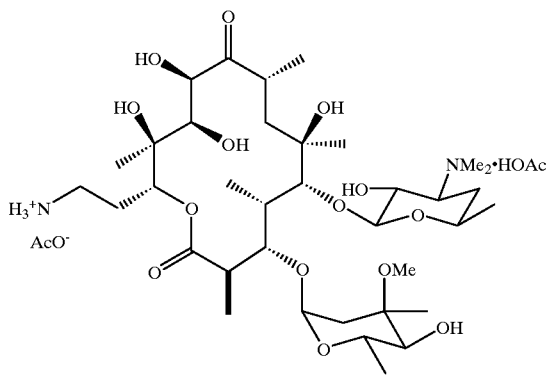

A solution of 15-azidoerythromycin A (7.75 g, 10 mmol) in 50 mL of methanol is treated with acetic acid (2.0 mL) and 10% palladium on carbon (0.1 g) and stirred under 1 atm of hydrogen gas until thin-layer chromatographic analysis reveals complete reduction of the starting material. The suspension is filtered through Celite to remove the catalyst, then evaporated to dryness to yield the product, which is used as a starting material for the following derivatizations.

A. Synthesis of 15-(quinol-4-ylacetamido)erythromcin A

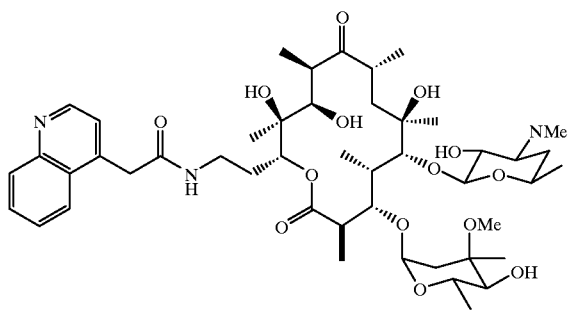

A solution of 15-aminoerythromycin A diacetate salt (1.0 g) in 10 mL of dichloromethane is treated sequentially with quinol-4-ylacetyl chloride (350 mg) and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

B. Synthesis of 15-(3-(quinol-4-yl)propionamido)erythromycin A

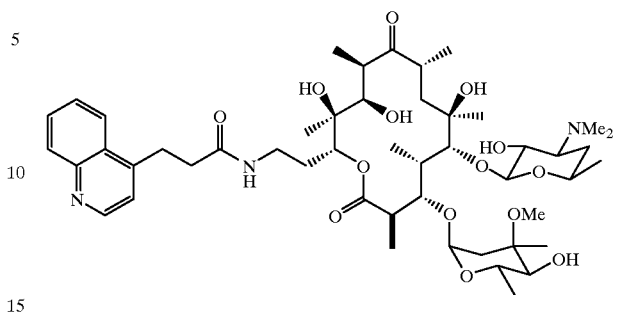

A solution of 15-aminoerythromycin A diacetate salt (1.0 g) in 10 mL of dichloromethane is treated sequentially with 3-(quinol-4-yl)propionyl chloride (400 mg) and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

C. Synthesis of 15-(isoquinol-4-ylacetamido)erythromycin A

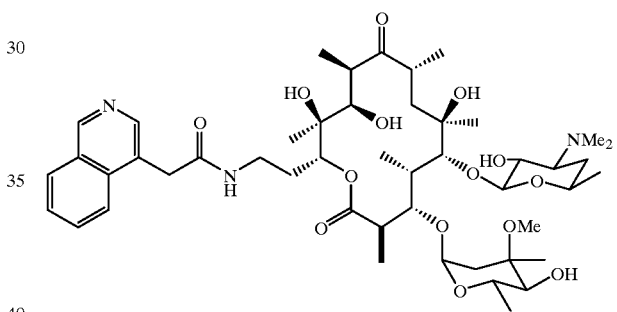

A solution of 15-aminoerythromycin A diacetate salt (1.0 g) in 10 mL of dichloromethane is treated sequentially with isoquinol-4-ylacetyl chloride (350 mg) and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

D. Synthesis of 15-(3-(isoquinol-4-yl)propionamido)erythromycin A

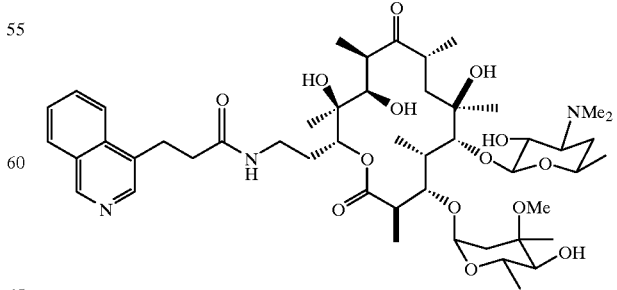

A solution of 15-aminoerythromycin A diacetate salt (1.0 g) in 10 mL of dichloromethane is treated sequentially with 3-(isoquinol-4-yl)propionyl chloride (400 mg) and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

E. Synthesis of 15-((quinol-5-ylamino)acetamido) erythromycin A

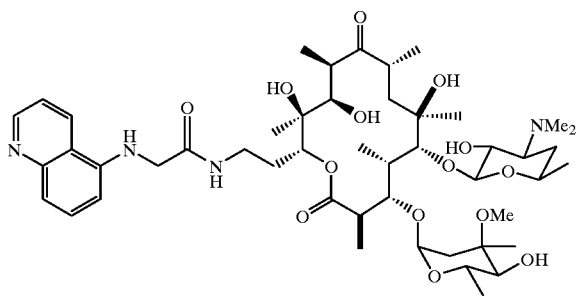

A solution of 15-aminoerythromycin A diacetate salt (1.0 g) in 10 mL of dichloromethane is treated sequentially with (quinol-5-ylamino)acetic acid (0.30 g), dicyclohexylcarbodiimide (0.4 g), 1-hydroxybenzotriazole (0.25 g), and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

F. Synthesis of 15-((quinol-6-ylamino)acetamido) erythromycin A

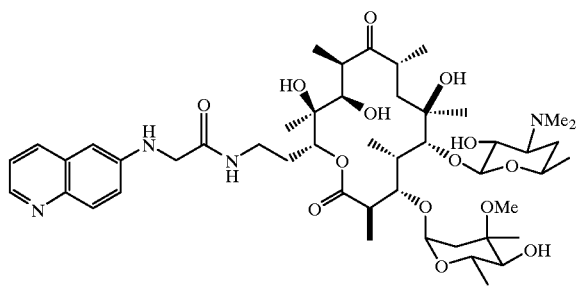

A solution of 15-aminoerythromycin A diacetate salt (1.0 g) in 10 mL of dichloromethane is treated sequentially with (quinol-6-ylamino)acetic acid (0.30 g), dicyclohexylcarbodiimide (0.4 g), 1-hydroxybenzotriazole (0.25 g), and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

G. Synthesis of 15-((quinol-4-ylmethyl)carbamoylamino) erythromycin A

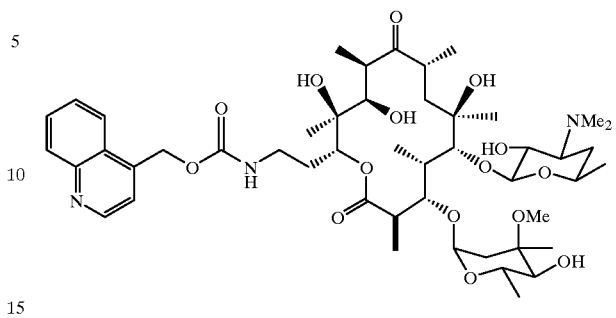

A solution of 15-aminoerythromycin A diacetate salt (1.0 g) in 10 mL of dichloromethane is treated sequentially with quinoline-4-methoxycarbonyl chloride (400 mg) and triethylamine (0.5 mL) at 0° C. After 3 hours, the reaction is diluted with dichloromethane and washed three times with saturated aqueous NaHCO$_3$. The organic phase is dried over MgSO$_4$, filtered, and evaporated to yield the crude product. Purification by silica gel chromatography yields the pure product.

Example 31

6-O-Methyl-3-descladinosyl-3-oxo-11-deoxy-11-amino-15-(3-(quinol-4-yl)propionamido) erythromycin A 11,12-cyclic carbamate

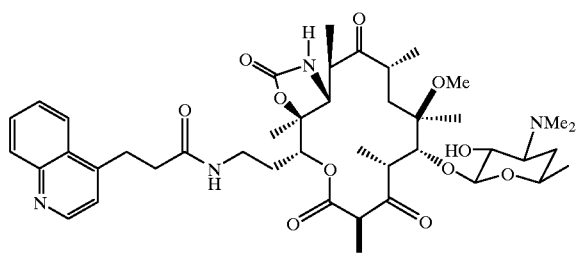

This is prepared according to the procedures described in Example 30, starting with 15-(3-(quinol-4-yl)propionamido) erythromycin A.

Example 32

6-O-Methyl-3-descladinosyl-3-oxo-11-deoxy-11-amino-2-fluoro-15-(3-(quinol-4-yl)propionamido) erythromycin A 11,12-cyclic carbamate

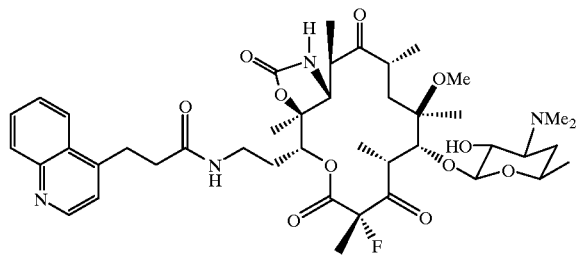

Step 1. To a solution of 2'-O-benzoyl-6-O-methyl-3-descladinosyl-3-oxo-11-deoxy-11-amino-15-(3-(quinol-4- yl)propionamido)erythromycin A 11,12-cyclic carbamate in THF is added a TBE solution of potassium tert-butoxide (2.3 eq.) at −78° C. The reaction mixture is then kept at −60° C. to −40° C. for 20 min., followed by introduction of N-Fluorobenzenesulfonimide (1.1 eq.) in THF (0.2 ml) at −78° C. The reaction mixture is kept at −70° C. to −40° C. for 1 h before it is allowed to warm to 0° C. from −70° C. in 1.5 h. It is then diluted with EtOAc, washed with saturated aqueous NaHCO$_3$, water, and brine. The organic phase is dried over MgSO$_4$, filtered, and concentrated. Flash chromatography yields the desired product as the 2'-O-benzoate.

Step 2. The product of Step 1 is dissolved in 1 mL of methanol, sealed, and refluxed at 80° C. for 16 h. Volatiles are removed under reduced pressure. Flash chromatography yields the desired product.

Example 33

2'-O-Benzoyl-6-O-methyl-3-descladinosyl-3-oxo-11-deoxy-11-amino-15-ethenylerythromycin A 11,12-cyclic carbamate

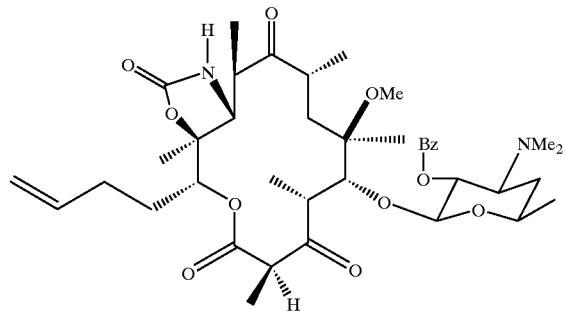

This is prepared according to the procedures described previously, starting with 15-ethenylerythromycin A.

Example 34

6-O-methyl-3-descladinosyl-3-oxo-11-deoxy-11-amino-15-ethenylerythromycin A 11,12-cyclic carbamate

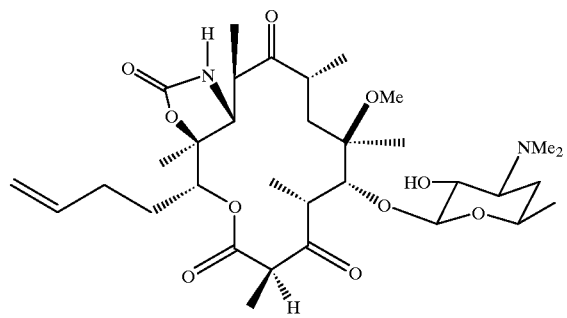

2'-O-Benzoyl-6-O-methyl-3-descladinosyl-3-oxo-11-deoxy-11-amino-15-ethenylerythromycin A 11,12-cyclic carbamate from Example 33 is dissolved in 1 mL of methanol, sealed, and refluxed at 80° C. for 16 h. Volatiles are removed under reduced pressure. Flash chromatography yields the desired product.

Example 35

6-O-Methyl-3-descladinosyl-3-oxo-11-deoxy-11-amino-2-fluoro-15-ethenylerythromycin A 11,12-cyclic carbamate

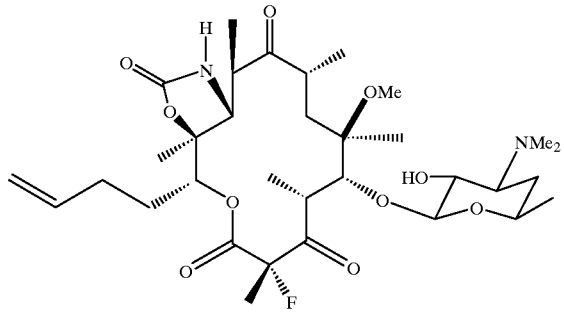

Step 1. To a solution of 2'-O-benzoyl-6-O-methyl-3-descladinosyl-3-oxo-11-deoxy-11-amino-15-ethenylerythromycin A 11,12-cyclic carbamate in THF is added a THF solution of potassium tert-butoxide (2.3 eq.) at −78° C. The reaction mixture is then kept at −60° C. to 40° C. for 20 min., followed by introduction of N-Fluorobenzenesulfonimide (1.1 eq.) in THF (0.2 ml) at −78° C. The reaction mixture is kept at −70° C. to −40° C. for 1 h before it is allowed to warm to 0° C. from −70° C. in 1.5 h.

It is then diluted with EtOAc, washed with saturated aqueous NaHCO$_3$, water, and brine. The organic phase is dried over MgSO$_4$, filtered, and concentrated. Flash chromatography yields the desired product as the 2'-O-benzoate.

Step 2. The product of Step 1 is dissolved in 1 mL of methanol, sealed, and refluxed at 80° C. for 16 h. Volatiles are removed under reduced pressure. Flash chromatography yields the desired product.

Example 36

6-O-Methyl-3-descladinosyl-3-oxo-11-deoxy-11-amino-15-(2-(3-quinolyl ethenyl erythromycin A 11,12-cyclic carbamate

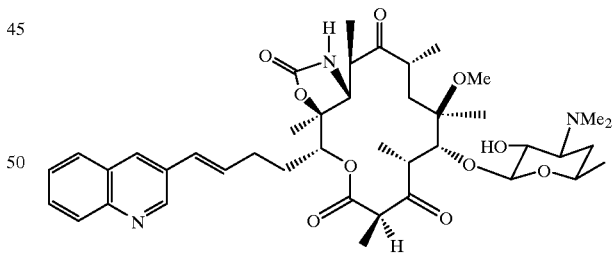

Step 1: 2'-O-Benzoyl-6-O-methyl-11-amino-3-descladinosyl-11-deoxy-3-oxo-15-ethenylerythromycin A 11,12-cyclic carbamate (40 mg), tris(dibenzylideneacetone)dipalladium(0)-chloroform adduct (14 mg), tri-o-tolylphosphine (17 mg), and 3-bromoquinoline (72 µl) are placed in a round-bottom flask which is flushed with N$_2$. Degassed acetonitrile (1 mL) and freshly distilled Et$_3$N (0.015 ml) are added. The reaction is refluxed for 63 h. The mixture is returned to ambient temperature and diluted with 40 mL of EtOAc. The solution is washed successively with 10 mL each of saturated aqueous NaHCO$_3$, water, and brine. The organic phase is dried over MgSO$_4$, filtered, and concentrated. Flash chromatography of the crude product yields the desired product.

Step 2: The product of Step 1 is dissolved in 1 mL of methanol, sealed, and refluxed at 80° C. for 16 h. Volatiles are removed under reduced pressure. Flash chromatography yields the desired product.

Example 37

6-O-Methyl-3-descladinosyl-3-oxo-11-deoxy-11-amino-2-fluoro-15-(2-(3-quinolyl)ethenyl) erythromycin A 11,12-cyclic carbamate

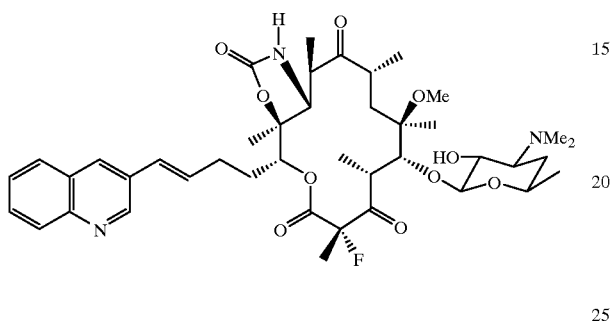

Step 1: 2'-O-Benzoyl-6-O-methyl-11-amino-3-descladinosyl-11-deoxy-3-oxo-2-fluoro-15-ethenylerythromycin A 11,12-cyclic carbamate (40 mg), tris(dibenzylideneacetone) dipalladium(0)-chloroform adduct (14 mg), tri-o-tolylphosphine (17 mg), and 3-bromoquinoline (72 μl) are placed in a round-bottom flask which is flushed with $N_2$. Degassed acetonitrile (1 mL) and freshly distilled $Et_3N$ (0.015 ml) are added. The reaction is refluxed for 63 h. The mixture is returned to ambient temperature and diluted with 40 mL of EtOAc. The solution is washed successively with 10 mL each of saturated aqueous $NaHCO_3$, water, and brine. The organic phase is dried over $MgSO_4$, filtered, and concentrated. Flash chromatography of the crude product yields the desired product.

Step 2: The product of Step 1 is dissolved in 1 mL of methanol, sealed, and refluxed at 80° C. for 16 h. Volatiles are removed under reduced pressure. Flash chromatography yields the desired product.

Example 38

6-O-Methyl-3-descladinosyl-3-oxo-11-deoxy-11-amino-2-fluoro-15-(2-(3-quinolylmethyl ethenyl erythromycin A 11,12-cyclic carbamate

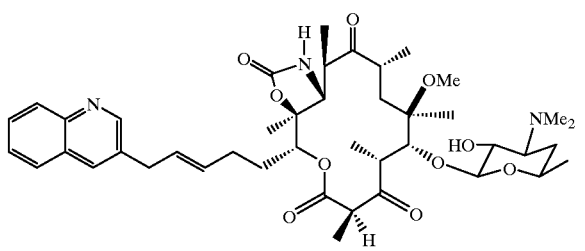

Step 1: A mixture of 2'-O-benzoyl-6-O-methyl-11-amino-3-descladinosyl-11-deoxy-3-oxo-2-fluoro-15-ethenylerythromycin A 11,12-cyclic carbamate, 3-allylquinoline, and bis(triphenylphosphine) benzylidenerhodium chloride is heated in refluxing benzene for 8 hours. The mixture is returned to ambient temperature and diluted with 40 mL of EtOAc. The solution is washed successively with 10 mL each of saturated aqueous $NaHCO_3$, water, and brine. The organic phase is dried over $MgSO_4$, filtered, and concentrated. Flash chromatography of the crude product yields the desired product.

Step 2: The product of Step 1 is dissolved in 1 mL of methanol, sealed, and refluxed at 80° C. for 16 h. Volatiles are removed under reduced pressure. Flash chromatography yields the desired product.

What is claimed is:

1. A compound of the formula

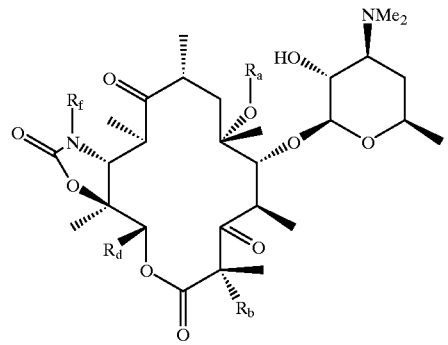

or a pharmaceutically acceptable salt thereof or a stereoisomeric form thereof or a mixture of stereoisomeric forms thereof wherein $R_a$ is substituted or unsubstituted aryl (4–14C); substituted or unsubstituted arylalkyl (5–20C); substituted or unsubstituted arylalkenyl (5–20C); substituted or unsubstituted arylalkynyl (5–20C);

$R_b$ is H or halogen;

$R_d$ is fluoroethyl; and $R_f$ is H or C1–C3 alkyl.

2. The compound of claim 1 wherein $R_b$ is H.
3. The compound of claim 1 wherein $R_b$ is halogen.
4. The compound of claim 1 wherein $R_b$ is fluoro.
5. The compound of claim 1 wherein $R_f$ is H.
6. The compound of claim 1 wherein $R_f$ is C1–C3 alkyl.
7. The compound of claim 1 wherein $R_f$ is methyl.
8. The compound of claim 1 wherein $R_a$ is substituted or unsubstituted aryl (4–14C).
9. The compound of claim 1 wherein $R_a$ is substituted or unsubstituted arylalkyl (5–20C).
10. The compound of claim 1 wherein $R_a$ is substituted or unsubstituted arylalkenyl (5–20C).
11. The compound of claim 1 wherein $R_a$ is substituted or unsubstituted arylalkynyl (5–20C).
12. The compound of claim 1 wherein $R_a$ is 3-aryl-prop-2-enyl or 3-aryl-prop-2-ynyl.
13. The compound of claim 12 wherein said aryl is 3-quinolyl, 4-quinolyl, 5-quinolyl, phenyl, 4-fluorophenyl, 4-chlorophenyl, 4-methoxyphenyl, 6-quinolyl, 6-quinoxalyl, 6-amino-3-quinolyl, or 4-isoquinolyl.
14. The compound of claim 1 wherein $R_a$ is 3-aryl-prop-2-ynyl.
15. The compound of claim 14 wherein said aryl is 3-quinolyl, 4-quinolyl, 5-quinolyl, phenyl, 4-fluorophenyl, 4-chlorophenyl, 4-methoxyphenyl, 6-quinolyl, 6-quinoxalyl, 6-amino-3-quinolyl, or 4-isoquinolyl.
16. A pharmaceutical composition comprising an effective amount of the compound of claim 1 in admixture with a pharmaceutical acceptable excipient.
17. A method to control infection in a subject which method comprises administering to a subject in need of such control an effective amount of the compound of claim 1 or a pharmaceutical composition thereof.

18. A method to preserve material from microbial decay which method comprises providing said material with an effective amount of the compound of claim 1.

19. A compound of the formula

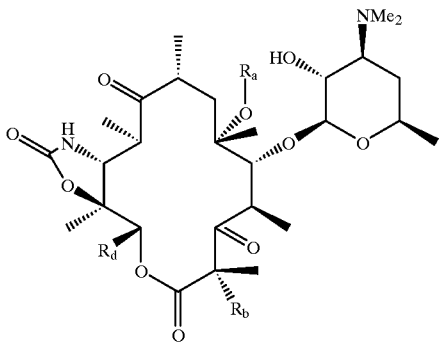

wherein $R_a$ is substituted or unsubstituted arylalkyl (5–20C); substituted or unsubstituted arylalkenyl (5–20C); or substituted or unsubstituted arylalkynyl (5–20C).

$R_b$ is H or F; and, $R_d$ is fluoroethyl.

20. The compound of claim 19 wherein $R_a$ is substituted or unsubstituted arylalkynyl.

21. The compound of claim 19 wherein $R_a$ is substituted or unsubstituted arylalkenyl.

22. The compound of claim 19 wherein $R_a$ is 3-aryl-prop-2-ynyl.

23. The compound of claim 19 wherein $R_a$ is 3-aryl-prop-2-enyl.

24. The compound of claim 23 wherein the aryl is 3-quinolyl, 4-quinolyl, 5-quinolyl, phenyl, 4-fluorophenyl, 4-chlorophenyl, 4-methoxyphenyl, 6-quinolyl, 6-quinoxalyl, 6-amino-3-quinolyl, or 4-isoquinolyl.

25. The compound of claim 23 wherein $R_a$ is 3-(6-quinoxalyl)-prop-2-enyl; and $R_b$ is H.

26. The compound of claim 23 wherein $R_a$ is 3-(3-quinolyl)-prop-2-enyl; and $R_b$ is H.

27. The compound of claim 23 wherein $R_a$ is 3-(6-quinoxalyl)-prop-2-enyl; and $R_b$ is F.

28. The compound of claim 23 wherein $R_a$ is 3-(3-quinolyl)-prop-2-enyl; and $R_b$ is F.

29. A compound of the formula

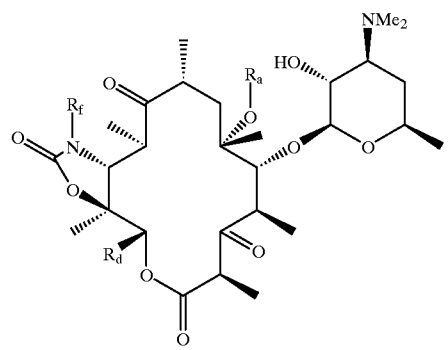

wherein $R_a$ is C1–C3 alkyl;

$R_d$ is fluoroethyl; and $R_f$ is substituted or unsubstituted aryl (4–14C); substituted or unsubstituted arylalkyl (5–20C).

30. The compound of claim 29 wherein $R_a$ is methyl.

31. The compound of claim 30 wherein $R_f$ is substituted or unsubstituted arylalkyl (5–20C).

32. A compound of the formula

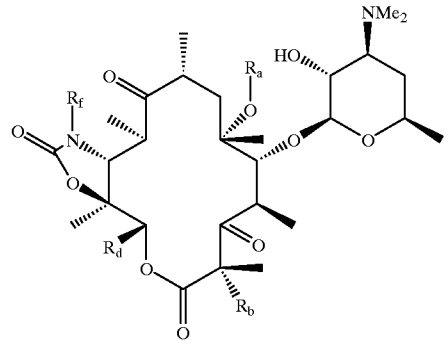

wherein $R_a$ is C1–C3 alkyl;

$R_b$ is halogen;

$R_d$ is fluoroethyl; and $R_f$ is substituted or unsubstituted aryl (4–14C); or substituted or unsubstituted arylalkyl (5–20C).

33. The compound of claim 32 wherein $R_b$ is fluoro.

34. The compound of claim 33 wherein $R_a$ is methyl.

35. The compound of claim 34 wherein $R_f$ is substituted or unsubstituted arylalkyl (5–20C).

* * * * *